United States Patent
Duncton et al.

(10) Patent No.: US 12,297,171 B2
(45) Date of Patent: May 13, 2025

(54) EP2 ANTAGONIST COMPOUNDS

(71) Applicant: Reservoir Neuroscience, Inc., Emeryville, CA (US)

(72) Inventors: Matthew Alexander James Duncton, San Bruno, CA (US); Vladimir V. Senatorov, Jr., Oakland, CA (US); Aaron R. Friedman, Berkeley, CA (US); Steven Howard Olson, San Diego, CA (US)

(73) Assignee: Reservoir Neuroscience, Inc., San Francisco, CA (US)

( * ) Notice: Subject to any disclaimer, the term of this patent is extended or adjusted under 35 U.S.C. 154(b) by 0 days.

(21) Appl. No.: 18/395,348

(22) Filed: Dec. 22, 2023

(65) Prior Publication Data

US 2024/0182411 A1   Jun. 6, 2024

Related U.S. Application Data

(63) Continuation of application No. PCT/US2022/034903, filed on Jun. 24, 2022.

(60) Provisional application No. 63/214,635, filed on Jun. 24, 2021.

(51) Int. Cl.
| | |
|---|---|
| C07D 205/04 | (2006.01) |
| C07D 207/09 | (2006.01) |
| C07D 401/04 | (2006.01) |
| C07D 403/04 | (2006.01) |

(52) U.S. Cl.
CPC ......... *C07D 205/04* (2013.01); *C07D 207/09* (2013.01); *C07D 401/04* (2013.01); *C07D 403/04* (2013.01)

(58) Field of Classification Search
CPC .. C07D 205/04; C07D 207/09; C07D 401/04; C07D 403/04
See application file for complete search history.

(56) References Cited

U.S. PATENT DOCUMENTS

| | | | |
|---|---|---|---|
| 8,278,343 B2 * | 10/2012 | Dack ..................... | A61P 13/12 548/536 |
| 11,241,431 B2 | 2/2022 | Fretz et al. | |
| 11,325,899 B2 | 5/2022 | Boss et al. | |
| 11,446,298 B2 | 9/2022 | Boss et al. | |
| 11,712,438 B2 | 8/2023 | Boss et al. | |
| 11,839,613 B2 | 12/2023 | Boss et al. | |
| 12,011,444 B2 | 6/2024 | Fretz et al. | |
| 2010/0120793 A1 | 5/2010 | Dack et al. | |
| 2012/0316147 A1 | 12/2012 | Bissantz et al. | |
| 2018/0079756 A1 | 3/2018 | Ikeda et al. | |
| 2022/0048987 A1 | 2/2022 | Andreasson et al. | |
| 2022/0175775 A1 | 6/2022 | Fretz et al. | |
| 2022/0388955 A1 | 12/2022 | Watanabe et al. | |

FOREIGN PATENT DOCUMENTS

| | | |
|---|---|---|
| WO | WO2008012635 A2 | 1/2008 |
| WO | WO2008/139287 A1 | 11/2008 |
| WO | WO2010052625 | 5/2010 |
| WO | WO2018169818 A1 | 9/2018 |

OTHER PUBLICATIONS

Af Forselles KJ, Root J, Clarke T, Davey D, Aughton K, Dack K, Pullen N. 2011. In vitro and in vivo characterization of PF-04418948, a novel, potent and selective prostaglandin EP$_2$ receptor antagonist. British Journal of Pharmacology 164:1847-1856. doi:10.1111/j.1476-5381.2011.01495.x.

Alhallak K, Nagai J, Zaleski K, et al. Mast cells control lung type 2 inflammation via prostaglandin E2-driven soluble ST2. Immunity. 2024;57(6):1274-1288.e6. doi:10.1016/j.immuni.2024.05.003.

Amaradhi R, Banik A, Mohammed S, Patro V, Rojas A, Wang W, Motati DR, Dingledine R, Ganesh T. 2020. Potent, Selective, Water Soluble, Brain-Permeable EP2 Receptor Antagonist for Use in Central Nervous System Disease Models. J Med Chem 63:1032-1050. doi:10.1021/acs.jmedchem.9b01218.

Amaradhi R, Mohammed S, Banik A, Franklin R, Dingledine R, Ganesh T. 2022. Second-Generation Prostaglandin Receptor EP2 Antagonist, TG8-260, with High Potency, Selectivity, Oral Bioavailability, and Anti-Inflammatory Properties. ACS Pharmacol Transl Sci 5:118-133. doi:10.1021/acsptsci.1c00255.

Aoki T, Frösen J, Fukuda M, Bando K, Shioi G, Tsuji K, Ollikainen E, Nozaki K, Laakkonen J, Narumiya S. 2017. Prostaglandin E2-EP2-NF-κB signaling in macrophages as a potential therapeutic target for intracranial aneurysms. Sci Signal 10:eaah6037. doi:10.1126/scisignal.aah6037.

Arosh JA, Lee J, Balasubbramanian D, Stanley JA, Long CR, Meagher MW, Osteen KG, Bruner-Tran KL, Burghardt RC, Starzinski-Powitz A, Banu SK. 2015. Molecular and preclinical basis to inhibit PGE2 receptors EP2 and EP4 as a novel nonsteroidal therapy for endometriosis. Proc Natl Acad Sci U S A 112:9716-9721. doi:10.1073/pnas.1507931112.

Banik A, Amaradhi R, Lee D, Sau M, Wang W, Dingledine R, Ganesh T. 2021. Prostaglandin EP2 receptor antagonist ameliorates neuroinflammation in a two-hit mouse model of Alzheimer's disease. J Neuroinflammation 18:273. doi:10.1186/s12974-021-02297-7.

Birrell MA, Maher SA, Buckley J, Dale N, Bonvini S, Raemdonck K, Pullen N, Giembycz MA, Belvisi MG. 2013. Selectivity profiling of the novel EP2 receptor antagonist, PF-04418948, in functional bioassay systems: atypical affinity at the guinea pig EP2 receptor. Br J Pharmacol 168:129-138. doi: 10.1111/j.1476-5381.2012.02088.x.

(Continued)

*Primary Examiner* — Rebecca L Anderson
(74) *Attorney, Agent, or Firm* — Travis Young; Bozicevic Field & Francis LLP

(57) ABSTRACT

Described herein are compounds that are EP2 antagonists, methods of making such compounds, pharmaceutical compositions and medicaments comprising such compounds, and methods of using such compounds in the treatment of diseases or conditions associated with EP2 activity.

17 Claims, No Drawings

(56) References Cited

OTHER PUBLICATIONS

Birrell MA, Nials AT. 2011. At last, a truly selective EP2 receptor antagonist. Br J Pharmacol 164:1845-1846. doi:10.1111/j.1476-5381.2011.01494.x.
Bonfill-Teixidor E, Otxoa-de-Amezaga A, Font-Nieves M, Sans-Fons MG, Planas AM. 2017. Differential expression of E-type prostanoid receptors 2 and 4 in microglia stimulated with lipopolysaccharide. J Neuroinflammation 14:3. doi:10.1186/s12974-016-0780-7.
Chen J, Deng JC, Zemans RL, et al. Age-induced prostaglandin E2 impairs mitochondrial fitness and increases mortality to influenza infection. Nat Commun. 2022;13(1):6759. Published Nov. 9, 2022. doi:10.1038/s41467-022-34593-y.
Fang LZ, Linehan V, Licursi M, et al. Prostaglandin E2 activates melanin-concentrating hormone neurons to drive diet-induced obesity. Proc Natl Acad Sci U S A. 2023;120(31):e2302809120. doi:10.1073/pnas.2302809120.
Fox BM, Beck HP, Roveto PM, Kayser F, Cheng Q, Dou H, Williamson T, Treanor J, Liu H, Jin L, Xu G, Ma J, Wang S, Olson SH. 2015. A selective prostaglandin E2 receptor subtype 2 (EP2) antagonist increases the macrophage-mediated clearance of amyloid-beta plaques. J Med Chem 58:5256-5273. doi:10.1021/acs.jmedchem.5b00567.
Francica BJ, Holtz A, Lopez J, Freund D, Chen A, Wang D, Powell D, Kipper F, Panigrahy D, Dubois RN, Whiting CC, Prasit P, Dubensky TW. 2023. Dual Blockade of EP2 and EP4 Signaling is Required for Optimal Immune Activation and Antitumor Activity Against Prostaglandin-Expressing Tumors. Cancer Res Commun 3:1486-1500. doi:10.1158/2767-9764.CRC-23-0249.
Ganesh T, Banik A, Dingledine R, Wang W, Amaradhi R. 2018. Peripherally Restricted, Highly Potent, Selective, Aqueous-Soluble EP2 Antagonist with Anti-Inflammatory Properties. Mol Pharm 15:5809-5817. doi:10.1021/acs.molpharmaceut.8b00764.
Ganesh T, Jiang J, Dingledine R. 2014a. Development of second generation EP2 antagonists with high selectivity. Eur J Med Chem 82:521-535. doi:10.1016/j.ejmech.2014.05.076.
Ganesh T, Jiang J, Shashidharamurthy R, Dingledine R. 2013. Discovery and characterization of carbamothioylacrylamides as EP2 selective antagonists. ACS Med Chem Lett 4:616-621. doi:10.1021/ml400112h.
Ganesh T, Jiang J, Yang M-S, Dingledine R. 2014b. Lead optimization studies of cinnamic amide EP2 antagonists. J Med Chem 57:4173-4184. doi:10.1021/jm5000672.
Ganesh T. 2014. Prostanoid receptor EP2 as a therapeutic target. J Med Chem 57:4454-4465. doi:10.1021/jm401431x.
Ganesh T. 2023. Targeting EP2 Receptor for Drug Discovery: Strengths, Weaknesses, Opportunities, and Threats (SWOT) Analysis. J Med Chem 66:9313-9324. doi:10.1021/acs.jmedchem.3c00655.
Gill SK, Yao Y, Kay LJ, Bewley MA, Marriott HM, Peachell PT. 2016. The anti-inflammatory effects of PGE2 on human lung macrophages are mediated by the EP4 receptor. Br J Pharmacol 173:3099-3109. doi:10.1111/bph.13565.
Golden J, Illingworth L, Kavarian P, et al. EP2 Receptor Blockade Attenuates COX-2 Upregulation During Intestinal Inflammation. Shock. 2020;54(3):394-401. doi:10.1097/SHK.0000000000001444.
Jiang C, Amaradhi R, Ganesh T, Dingledine R. 2020. An Agonist Dependent Allosteric Antagonist of Prostaglandin EP2 Receptors. ACS Chem Neurosci 11:1436-1446. doi:10.1021/acschemneuro.0c00078.
Jiang J, Dingledine R. 2013. Prostaglandin receptor EP2 in the crosshairs of anti-inflammation, anti-cancer, and neuroprotection. Trends Pharmacol Sci 34:413-423. doi:10.1016/j.tips.2013.05.003.
Jiang J, Ganesh T, Du Y, Quan Y, Serrano G, Qui M, Speigel I, Rojas A, Lelutiu N, Dingledine R. 2012. Small molecule antagonist reveals seizure-induced mediation of neuronal injury by prostaglandin E2 receptor subtype EP2. Proc Natl Acad Sci U S A 109:3149-3154. doi:10.1073/pnas.1120195109.
Jiang J, Quan Y, Ganesh T, Pouliot WA, Dudek FE, Dingledine R. 2013. Inhibition of the prostaglandin receptor EP2 following status epilepticus reduces delayed mortality and brain inflammation. Proc Natl Acad Sci U S A 110:3591-3596. doi:10.1073/pnas.1218498110.
Jones VC, Birrell MA, Maher SA, Griffiths M, Grace M, O'Donnell VB, Clark SR, Belvisi MG. 2016. Role of EP2 and EP4 receptors in airway microvascular leak induced by prostaglandin E2. Br J Pharmacol 173:992-1004. doi:10.1111/bph.13400.
Kameyama H, Dondapati P, Simmons R, et al. Needle biopsy accelerates pro-metastatic changes and systemic dissemination in breast cancer: Implications for mortality by surgery delay. Cell Rep Med. 2023;4(12):101330. doi:10.1016/j.xcrm.2023.101330.
Kawahara K, Hohjoh H, Inazumi T, Tsuchiya S, Sugimoto Y. 2015. Prostaglandin E2-induced inflammation: Relevance of prostaglandin E receptors. Biochim Biophys Acta 1851:414-421. doi:10.1016/j.bbalip.2014.07.008.
Kay LJ, Gilbert M, Pullen N, Skerratt S, Farrington J, Seward EP, Peachell PT. 2013. Characterization of the EP receptor subtype that mediates the inhibitory effects of prostaglandin E2 on IgE-dependent secretion from human lung mast cells. Clin Exp Allergy 43:741-751. doi:10.1111/cea.12142.
Keery RJ, Lumley P. 1988. AH6809, a prostaglandin DP-receptor blocking drug on human platelets. Br J Pharmacol 94:745-754. doi:10.1111/j.1476-5381.1988.tb11584.x.
Li L, Yu Y, Hou R, Hao J, Jiang J. 2020. Inhibiting the PGE2 Receptor EP2 Mitigates Excitotoxicity and Ischemic Injury. ACS Pharmacol Transl Sci 3:635-643. doi:10.1021/acsptsci.0c00040.
Li P, Jiang H, Wu H, Wu D, Li H, Yu J, Lai J. 2018. AH6809 decreases production of inflammatory mediators by PGE2—EP2—CAMP signaling pathway in an experimentally induced pure cerebral concussion in rats. Brain Res 1698:11-28. doi:10.1016/j.brainres.2018.05.030.
Liu Q, Liang X, Wang Q, Wilson EN, Lam R, Wang J, Kong W, Tsai C, Pan T, Larkin PB, Shamloo M, Andreasson KI. 2019. PGE2 signaling via the neuronal EP2 receptor increases injury in a model of cerebral ischemia. Proc Natl Acad Sci U S A 116:10019-10024. doi:10.1073/pnas.1818544116.
Makabe T, Koga K, Nagabukuro H, et al. Use of selective PGE2 receptor antagonists on human endometriotic stromal cells and peritoneal macrophages. Mol Hum Reprod. 2021;27(1):gaaa077. doi:10.1093/molehr/gaaa077.
Markovič T, Jakopin Ž, Dolenc MS, Mlinarič-Raščan I. 2017. Structural features of subtype-selective EP receptor modulators. Drug Discov Today 22:57-71. doi:10.1016/j.drudis.2016.08.003.
Minhas PS, Latif-Hernandez A, McReynolds MR, Durairaj AS, Wang Q, Rubin A, Joshi AU, He JQ, Gauba E, Liu L, Wang C, Linde M, Sugiura Y, Moon PK, Majeti R, Suematsu M, Mochly-Rosen D, Weissman IL, Longo FM, Rabinowitz JD, Andreasson KI. 2021. Restoring metabolism of myeloid cells reverses cognitive decline in ageing. Nature. doi:10.1038/s41586-020-03160-0.
Nakamura N, Honjo M, Yamagishi R, Sakata R, Watanabe S, Aihara M. Synergic effects of EP2 and FP receptors co-activation on Blood-Retinal Barrier and Microglia. Exp Eye Res. 2023;237:109691. doi:10.1016/j.exer.2023.109691.
Morotti M, Grimm AJ, Hope HC, Arnaud M, Desbuisson M, Rayroux N, Barras D, Masid M, Murgues B, Chap BS, Ongaro M, Rota IA, Ronet C, Minasyan A, Chiffelle J, Lacher SB, Bobisse S, Murgues C, Ghisoni E, Ouchen K, Bou Mjahed R, Benedetti F, Abdellaoui N, Turrini R, Gannon PO, Zaman K, Mathevet P, Lelievre L, Crespo I, Conrad M, Verdeil G, Kandalaft LE, Dagher J, Corria-Osorio J, Doucey M-A, Ho P-C, Harari A, Vannini N, Böttcher JP, Dangaj Laniti D, Coukos G. 2024. PGE2 inhibits TIL expansion by disrupting IL-2 signalling and mitochondrial function. Nature 629:426-434. doi:10.1038/s41586-024-07352-w.
Perrot CY, Herrera JL, Fournier-Goss AE, Komatsu M. 2020. Prostaglandin E2 breaks down pericyte-endothelial cell interaction via EP1 and EP4-dependent downregulation of pericyte N-cadherin, connexin-43, and R-Ras. Sci Rep 10:11186. doi:10.1038/s41598-020-68019-w.
Rawat V, Banik A, Amaradhi R, Rojas A, Taval S, Nagy T, Dingledine R, Ganesh T. 2022. Pharmacological antagonism of EP2 receptor does not modify basal cardiovascular and respiratory

(56) References Cited

OTHER PUBLICATIONS function, blood cell counts, and bone morphology in animal models. Biomed Pharmacother 147:112646. doi:10.1016/j.biopha.2022.112646.

Rojas A, Amaradhi R, Banik A, Jiang C, Abreu-Melon J, Wang S, Dingledine R, Ganesh T. 2021. A Novel Second-Generation EP2 Receptor Antagonist Reduces Neuroinflammation and Gliosis After Status Epilepticus in Rats. Neurotherapeutics 18:1207-1225. doi:10.1007/s13311-020-00969-5.

Rojas A, Ganesh T, Lelutiu N, Gueorguieva P, Dingledine R. 2015. Inhibition of the prostaglandin EP2 receptor is neuroprotective and accelerates functional recovery in a rat model of organophosphorus induced status epilepticus. Neuropharmacology 93:15-27. doi: 10.1016/j.neuropharm.2015.01.017.

Rojas A, Ganesh T, Manji Z, O'neill T, Dingledine R. 2016. Inhibition of the prostaglandin E2 receptor EP2 prevents status epilepticus-induced deficits in the novel object recognition task in rats. Neuropharmacology 110:419-430. doi:10.1016/j.neuropharm.2016.07.028.

Rojas A, Ganesh T, Wang W, Wang J, Dingledine R. 2020. A rat model of organophosphate-induced status epilepticus and the beneficial effects of EP2 receptor inhibition. Neurobiol Dis 133:104399. doi:10.1016/j.nbd.2019.02.010.

Säfholm J, Manson ML, Bood J, et al. Prostaglandin E2 inhibits mast cell-dependent bronchoconstriction in human small airways through the E prostanoid subtype 2 receptor. J Allergy Clin Immunol. 2015;136(5):1232-9.e1. doi:10.1016/j.jaci.2015.04.002.

Sluter MN, Hou R, Li L, Yasmen N, Yu Y, Liu J, Jiang J. 2021. EP2 Antagonists (2011-2021): A Decade's Journey from Discovery to Therapeutics. J Med Chem 64:11816-11836. doi:10.1021/acs.jmedchem.1c00816.

Thumkeo D, Punyawatthananukool S, Prasongtanakij S, Matsuura R, Arima K, Nie H, Yamamoto R, Aoyama N, Hamaguchi H, Sugahara S, Takeda S, Charoensawan V, Tanaka A, Sakaguchi S, Narumiya S. 2022. PGE2-EP2/EP4 signaling elicits immunosuppression by driving the mregDC-Treg axis in inflammatory tumor microenvironment. Cell Rep 39:110914. doi:10.1016/j.celrep.2022.110914.

Varvel NH, Amaradhi R, Espinosa-Garcia C, Duddy S, Franklin R, Banik A, Alemán-Ruiz C, Blackmar-Raynolds L, Wang W, Honore T, Ganesh T, Dingledine R. 2022. Preclinical development of an EP2 antagonist for post-seizure cognitive deficits. Neuropharmacology 224:109356. doi:10.1016/j.neuropharm.2022.109356.

Wang J, Zhi Z, Ding J, et al. Suppression of PGE2/EP2 signaling alleviates Hirschsprung disease by upregulating p38 mitogen-activated protein kinase activity. J Mol Med (Berl). 2023;101(9):1125-1139. doi:10.1007/s00109-023-02353-0.

Woodward DF, Pepperl DJ, Burkey TH, Regan JW. 1995. 6-Isopropoxy-9-oxoxanthene-2-carboxylic acid (AH 6809), a human EP2 receptor antagonist. Biochem Pharmacol 50:1731-1733. doi:10.1016/0006-2952(95)02035-7.

Zasłona Z, Pålsson-McDermott EM, Menon D, et al. The Induction of Pro-IL-1β by Lipopolysaccharide Requires Endogenous Prostaglandin E2 Production. J Immunol. 2017;198(9):3558-3564. doi:10.4049/jimmunol.1602072.

* cited by examiner

EP2 ANTAGONIST COMPOUNDS

CROSS-REFERENCE

This application is a continuation of PCT Application No. US2022/034903, filed Jun. 24, 2022, which claims the benefit of the earlier filing date of U.S. Provisional Patent Application No. 63/214,635 filed on Jun. 24, 2021. Both prior applications are incorporated herein by reference in their entireties.

FIELD OF THE INVENTION

Described herein are compounds that are inhibitors of prostaglandin E2 receptor 2, also known as EP2, methods of making such compounds, pharmaceutical compositions and medicaments comprising such compounds, and methods of using such compounds in the treatment of diseases or conditions associated with EP2 activity.

BACKGROUND OF THE INVENTION

EP2 is a prostaglandin receptor that functions, for example, as a mediator of inflammation. EP2 signaling is implicated in, for example, inflammatory conditions, allergic diseases, ocular diseases, nervous system diseases, bone diseases, fibrotic conditions, cardiovascular diseases, and certain forms of cancer.

SUMMARY OF THE INVENTION

Compounds described herein are antagonists of EP2. In some embodiments, the compounds described herein are used in the treatment or prevention of diseases or conditions in which EP2 activity contributes to the symptomology or progression of the disease or condition, such as, for example, inflammatory diseases or conditions.

In one embodiment is a compound having the structure of Formula (I):

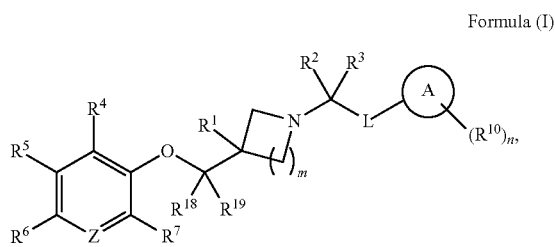

Formula (I)

or a pharmaceutically acceptable salt, or solvate thereof; wherein:

$R^1$ is

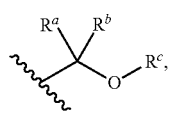

—C(O)NR$^d$R$^e$, —N(R$^f$)$_2$, substituted or unsubstituted monocyclic heterocycle, or substituted or unsubstituted monocyclic carbocycle, wherein if $R^1$ is a substituted monocyclic heterocycle, then it is substituted with one or more instances of $R^9$;

$R^a$ is hydrogen, deuterium, $C_1$-$C_6$ alkyl, $C_1$-$C_6$ deuteroalkyl, or $C_1$-$C_6$ fluoroalkyl;

$R^b$ is hydrogen, deuterium, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$ heterocycloalkyl;

or $R^a$ and $R^b$ are taken together with the carbon atom to which they are attached to form a ring C that is a substituted or unsubstituted $C_3$-$C_6$cycloalkyl, or substituted or unsubstituted $C_2$-$C_6$ heterocycloalkyl, wherein if the ring C is substituted then it is substituted with one or more $R^{11}$; and $R^c$ is hydrogen, $C_1$-$C_6$ alkyl, or $R^g$;

or $R^a$ and $R^b$ are taken together with the carbon atom to which they are attached to form a carbonyl (C=O); and $R^c$ is $C_3$-$C_6$ alkyl or $R^g$;

$R^d$ is —CN, $C_1$-$C_6$ alkyl, $C_1$-$C_6$ deuteroalkyl, $C_1$-$C_6$ fluoroalkyl, $C_{1-6}$ alkoxy, substituted or unsubstituted $C_3$-$C_6$ cycloalkyl, substituted or unsubstituted $C_2$-$C_6$ heterocycloalkyl, —OH, OR$^{1d}$, —SOR$^{1d}$, or —SO$_2$R$^{1d}$; wherein R$^{1d}$ is substituted or unsubstituted $C_1$-$C_6$ alkyl, substituted or unsubstituted $C_3$-$C_6$ cycloalkyl, substituted or unsubstituted 3- to 6-membered heterocycloalkyl, substituted or unsubstituted phenyl, or substituted or unsubstituted 5- to 6-membered heteroaryl; wherein if R$^{1d}$ is substituted then it is substituted with one or more R$^{14}$;

$R^e$ is hydrogen, $C_1$-$C_6$ alkyl, $C_1$-$C_6$ deuteroalkyl, $C_1$-$C_6$ fluoroalkyl, $C_{1-6}$ alkoxy, substituted or unsubstituted $C_3$-$C_6$ cycloalkyl, or substituted or unsubstituted $C_2$-$C_6$ heterocycloalkyl;

or $R^d$ and $R^e$ are taken together with the N atom to which they are attached to form a substituted or unsubstituted $C_2$-$C_6$ heterocycloalkyl;

each $R^f$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$heterocycloalkyl;

or both $R^f$ are taken together with the N atom to which they are attached to form a substituted or unsubstituted $C_2$-$C_6$heterocycloalkyl;

$R^g$ is $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$ cycloalkyl), -alkyl-(substituted or unsubstituted $C_2$-$C_6$ heterocycloalkyl), —C(=O)R$^{16}$, —C(=O)—OR$^{16}$, —C(=O)N(R$^{16}$)$_2$, —(C(R$^{17}$)$_2$O)$_p$—R$^{15}$, —(CH$_2$CH$_2$O)$_q$—R$^{15}$, or —(C(R$^{17}$)$_2$)$_p$—OR$^{15}$;

p is 1, 2, 3, 4, or 5;
q is 1, 2, 3, 4, or 5;
each R$^{17}$ is independently hydrogen or $C_1$-$C_6$ alkyl;
R$^{15}$ is hydrogen, substituted or unsubstituted alkyl, substituted or unsubstituted heteroalkyl, substituted or unsubstituted $C_2$-$C_{10}$ heterocycloalkyl, —C(=O)R$^{16}$, —C(=O)—OR$^{16}$, or —C(=O)N(R$^{16}$)$_2$;

$R^2$ is hydrogen, $C_1$-$C_6$ alkyl, $C_1$-$C_6$ deuteroalkyl, or $C_1$-$C_6$fluoroalkyl;

$R^3$ is hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$ heterocycloalkyl;

or $R^2$ and $R^3$ are taken together with the carbon atom to which they are attached to form a carbonyl (C=O) or thiocarbonyl (C=S);

or $R^2$ and $R^3$ are taken together with the carbon atom to which they are attached to form a ring B that is a substituted or unsubstituted $C_3$-$C_6$ cycloalkyl, or substituted or unsubstituted $C_2$-$C_6$ heterocycloalkyl, wherein if the ring B is substituted then it is substituted with one or more $R^2$;

Z is N or $CR^8$;

L is absent or —NH—;

$R^4$, $R^5$, $R^7$, and $R^8$ are each independently hydrogen, halogen, —CN, $C_1$-$C_6$ alkyl, $C_1$-$C_6$ deuteroalkyl, $C_1$-$C_6$ fluoroalkyl, —$OR^{16}$, —C(=O)$R^{16}$, —$CO_2R^{16}$, —C(=O)N($R^{16}$)$_2$, —N($R^{16}$)$_2$, or —$NR^{16}$C(=O)$R^{16}$;

$R^6$ is hydrogen, halogen, —CN, $C_1$-$C_6$ alkyl, $C_1$-$C_6$ deuteroalkyl, $C_1$-$C_6$ fluoroalkyl, —$OR^{16}$, —C(=O)$R^{16}$, —$CO_2R^{16}$, —C(=O)N($R^{16}$)$_2$, —N($R^{16}$)$_2$, —$NR^{16}$C(=O)$R^{16}$, substituted or unsubstituted $C_3$-$C_6$ cycloalkyl, substituted or unsubstituted $C_2$-$C_6$ heterocycloalkyl, substituted or unsubstituted phenyl, or substituted or unsubstituted heteroaryl;

wherein if $R^6$ is substituted then it is substituted with one or more $R^{13}$;

ring A is a substituted or unsubstituted phenyl, or substituted or unsubstituted heteroaryl;

each $R^9$, $R^{10}$, R, $R^{12}$, $R^{13}$, and $R^{14}$ is independently hydrogen, deuterium, halogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, —CN, —$OR^{16}$, —C(=O)$R^{16}$, —$CO_2R^{16}$, —C(=O)N($R^{16}$)$_2$, —N($R^{16}$)$_2$, or —$NR^{16}$C(=O)$R^{16}$;

each $R^{16}$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), or -alkyl-(substituted or unsubstituted $C_2$-$C_6$ heterocycloalkyl);

or both $R^{16}$ are taken together with the N atom to which they are attached to form a substituted or unsubstituted $C_2$-$C_6$ heterocycloalkyl;

$R^{18}$ and $R^{19}$ are each independently hydrogen, deuterium, $C_1$-$C_6$ alkyl, $C_1$-$C_6$ deuteroalkyl, or $C_1$-$C_6$ fluoroalkyl;

or $R^{18}$ and $R^{19}$ are taken together with the carbon atom to which they are attached to form a ring E that is a $C_3$-$C_6$cycloalky, or $C_2$-$C_6$ heterocycloalkyl;

m is 1 or 2; and n is 0, 1, 2, 3, or 4.

In another embodiment is a compound having the structure of Formula (II):

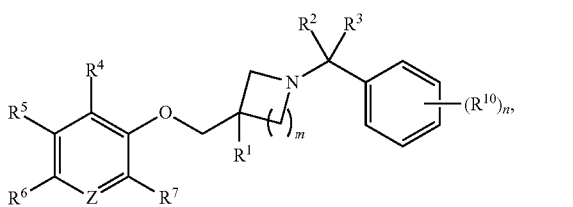

Formula (II)

or a pharmaceutically acceptable salt or solvate thereof

In another embodiment is a compound having the structure of Formula (III):

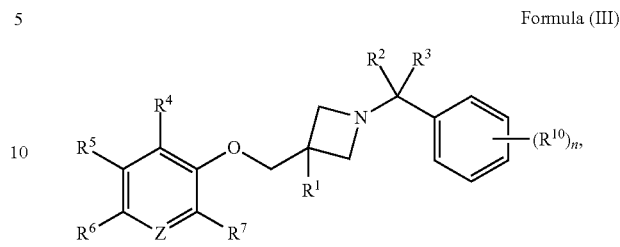

Formula (III)

or a pharmaceutically acceptable salt or solvate thereof.

In another embodiment is a compound having the structure of Formula (IV):

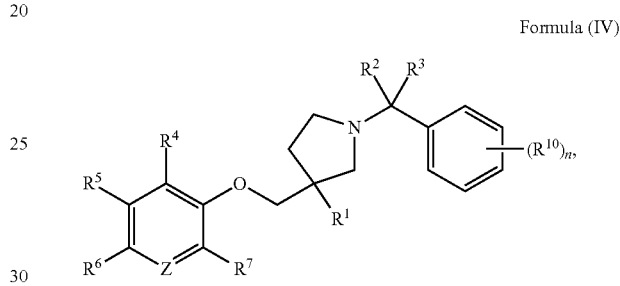

Formula (IV)

or a pharmaceutically acceptable salt or solvate thereof.

In another embodiment is a compound having the structure of Formula (VI):

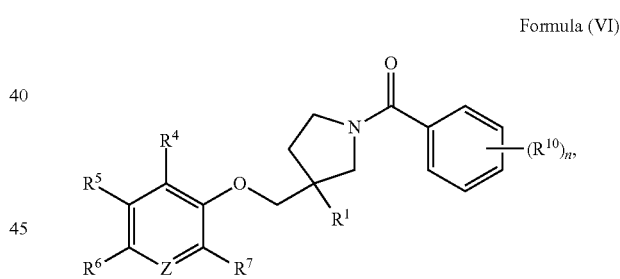

Formula (VI)

or a pharmaceutically acceptable salt or solvate thereof.

In another embodiment is a compound having the structure of Formula (VI-A):

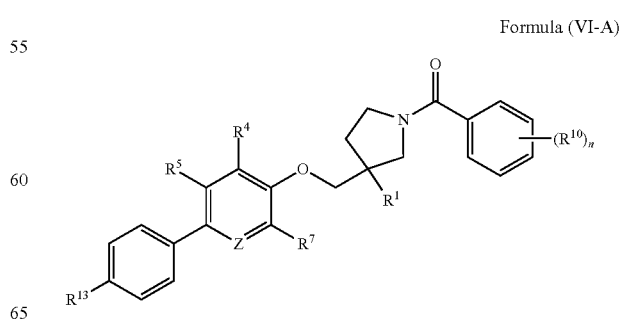

Formula (VI-A)

or a pharmaceutically acceptable salt, or solvate thereof.

In another embodiment is a compound having the structure of Formula (X):

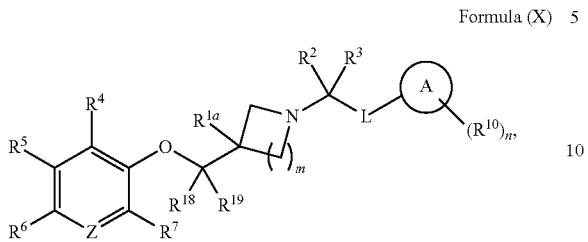

Formula (X)

wherein:
$R^{1a}$ is $-CO_2H$, $-CO_2-R^{1b}$, $-C(O)N(R^{1c})_2$, or $-CN$;
$R^{1b}$ is $C_1-C_6$ alkyl, $C_1-C_6$ deuteroalkyl, $C_1-C_6$ fluoroalkyl, substituted or unsubstituted $C_1-C_6$ heteroalkyl, substituted or unsubstituted $C_3-C_6$ cycloalkyl, substituted or unsubstituted $C_2-C_6$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3-C_6$cycloalkyl), -alkyl-(substituted or unsubstituted $C_2-C_6$heterocycloalkyl), $-C(=O)R^{16}$, $-C(=O)-OR^{16}$, $-C(=O)N(R^{16})_2$, $-(C(R^{17})_2O)_p-R^{15}$, $-(CH_2CH_2O)_q-R^{15}$, or $-(C(R^{17})_2)_p-OR^{15}$;
p is 1, 2, 3, 4, or 5;
q is 1, 2, 3, 4, or 5;
each $R^{17}$ is independently hydrogen or $C_1-C_6$ alkyl;
$R^{15}$ is hydrogen, substituted or unsubstituted alkyl, substituted or unsubstituted heteroalkyl, substituted or unsubstituted $C_2-C_{10}$heterocycloalkyl, $-C(=O)R^{16}$, $-C(=O)-OR^{16}$, or $-C(=O)N(R^{16})_2$;
each $R^{1c}$ is independently hydrogen, $C_1-C_6$ alkyl, $C_1-C_6$ deuteroalkyl, $C_1-C_6$ fluoroalkyl, substituted or unsubstituted $C_3-C_6$ cycloalkyl, substituted or unsubstituted $C_2-C_6$ heterocycloalkyl, $-OH$, $-SOR^{1d}$, or $-SO_2R^{1d}$; wherein $R^{1d}$ is substituted or unsubstituted $C_1-C_6$ alkyl;
or both $R^{1c}$ are taken together with the N atom to which they are attached to form a substituted or unsubstituted $C_2-C_6$ heterocycloalkyl;
$R^2$ is hydrogen, $C_1-C_6$ alkyl, $C_1-C_6$ deuteroalkyl, or $C_1-C_6$ fluoroalkyl;
$R^3$ is hydrogen, $C_1-C_6$ alkyl, $C_1-C_6$ deuteroalkyl, $C_1-C_6$ fluoroalkyl, substituted or unsubstituted $C_3-C_6$ cycloalkyl, or substituted or unsubstituted $C_2-C_6$ heterocycloalkyl;
or $R^2$ and $R^3$ are taken together with the carbon atom to which they are attached to form a thiocarbonyl (C=S);
or $R^2$ and $R^3$ are taken together with the carbon atom to which they are attached to form a ring B that is a substituted or unsubstituted $C_3-C_6$ cycloalkyl, or substituted or unsubstituted $C_2-C_6$ heterocycloalkyl, wherein if the ring B is substituted then it is substituted with one or more $R^{12}$;
Z is N or $CR^8$;
L is absent or $-NH-$;
$R^4$, $R^5$, $R^7$, and $R^8$ are each independently hydrogen, halogen, $-CN$, $C_1-C_6$ alkyl, $C_1-C_6$ deuteroalkyl, $C_1-C_6$ fluoroalkyl, $-OR^{16}$, $-C(=O)R^{16}$, $-CO_2R^{16}$, $-C(=O)N(R^{16})_2$, $-N(R^{16})_2$, or $-NR^{16}C(=O)R^{16}$;
$R^6$ is hydrogen, halogen, $-CN$, $C_1-C_6$ alkyl, $C_1-C_6$ deuteroalkyl, $C_1-C_6$ fluoroalkyl, $-OR^6$, $-C(=O)R^{16}$, $-CO_2R^{16}$, $-C(=O)N(R^{16})_2$, $-N(R^{16})_2$, $-NR^{16}C(=O)R^{16}$, substituted or unsubstituted $C_3-C_6$ cycloalkyl, substituted or unsubstituted $C_2-C_6$heterocycloalkyl, substituted or unsubstituted phenyl, or substituted or unsubstituted heteroaryl; wherein if $R^6$ is substituted then it is substituted with one or more $R^{13}$;
or $R^5$ and $R^6$ are taken together, with the intervening atoms to which they are attached, to form a fused ring D that is a substituted or unsubstituted 5- or 6-membered carbocycle or substituted or unsubstituted 5- or 6-membered heterocycle, wherein if ring D is substituted then it is substituted with one or more $R^{14}$;
ring A is a substituted or unsubstituted phenyl, or substituted or unsubstituted heteroaryl;
each $R^{10}$, $R^{12}$, $R^{13}$, and $R^{14}$ is independently hydrogen, deuterium, halogen, $C_1-C_6$ alkyl, $C_1-C_6$ deuteroalkyl, $C_1-C_6$ fluoroalkyl, substituted or unsubstituted $C_3-C_6$ cycloalkyl, substituted or unsubstituted $C_2-C_6$ heterocycloalkyl, $-CN$, $-OR^{16}$, $-C(=O)R^{16}$, $-CO_2R^{16}$, $-C(=O)N(R^{16})_2$, $-N(R^{16})_2$, or $-NR^{16}C(=O)R^{16}$;
each $R^{16}$ is independently hydrogen, $C_1-C_6$ alkyl, $C_1-C_6$ deuteroalkyl, $C_1-C_6$ fluoroalkyl, substituted or unsubstituted $C_3-C_6$ cycloalkyl, substituted or unsubstituted $C_2-C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3-C_6$ cycloalkyl), -alkyl-(substituted or unsubstituted $C_2-C_6$ heterocycloalkyl);
or both $R^{16}$ are taken together with the N atom to which they are attached to form a substituted or unsubstituted $C_2-C_6$ heterocycloalkyl;
$R^{18}$ and $R^{19}$ are each independently hydrogen, deuterium, $C_1-C_6$ alkyl, $C_1-C_6$ deuteroalkyl, or $C_1-C_6$ fluoroalkyl;
or $R^{18}$ and $R^{19}$ are taken together with the carbon atom to which they are attached to form a ring E that is a $C_3-C_6$cycloalky, or $C_2-C_6$ heterocycloalkyl;
m is 1 or 2; and
n is 0, 1, 2, 3, or 4.

In another embodiment is a compound having the structure of Formula (XX):

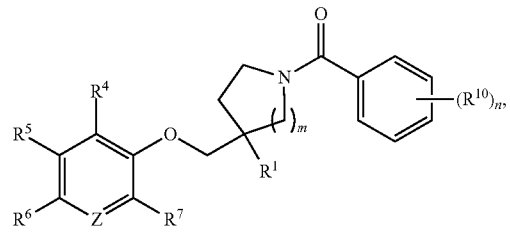

Formula (XX)

or a pharmaceutically acceptable salt, or solvate thereof;
wherein:
$R^1$ is

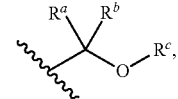

—C(O)NR$^d$R$^e$, —N(R$^f$)$_2$, substituted or unsubstituted monocyclic heterocycle, or substituted or unsubstituted monocyclic carbocycle, wherein if R$^1$ is a substituted monocyclic heterocycle, then it is substituted with one or more instances of R$^9$;

R$^a$ is hydrogen, deuterium, C$_1$-C$_6$ alkyl, C$_1$-C$_6$ deuteroalkyl, C$_1$-C$_6$ fluoroalkyl;

R$^b$ is hydrogen, deuterium, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, or substituted or unsubstituted C$_2$-C$_6$ heterocycloalkyl;

or R$^a$ and R$^b$ are taken together with the carbon atom to which they are attached to form a ring C that is a substituted or unsubstituted C$_3$-C$_6$cycloalkyl, or substituted or unsubstituted C$_2$-C$_6$ heterocycloalkyl, wherein if the ring C is substituted then it is substituted with one or more R$^{11}$; and R$^c$ is hydrogen, C$_1$-C$_6$ alkyl, or R$^g$;

or R$^a$ and R$^b$ are taken together with the carbon atom to which they are attached to form a carbonyl (C═O); and R$^c$ is C$_3$-C$_6$ alkyl or R$^g$;

R$^d$ is —CN, C$_1$-C$_6$ alkyl, C$_1$-C$_6$ deuteroalkyl, C$_1$-C$_6$ fluoroalkyl, C$_{1-6}$ alkoxy, substituted or unsubstituted C$_3$-C$_6$ cycloalkyl, substituted or unsubstituted C$_2$-C$_6$ heterocycloalkyl, —OH, —OR$^{1d}$, —SOR$^{1d}$, or —SO$_2$R$^{1d}$; wherein R$^{1d}$ is substituted or unsubstituted C$_1$-C$_6$ alkyl, substituted or unsubstituted C$_3$-C$_6$ cycloalkyl, substituted or unsubstituted 3- to 6-membered heterocycloalkyl, substituted or unsubstituted phenyl, or substituted or unsubstituted 5- to 6-membered heteroaryl; wherein if R$^{1d}$ is substituted then it is substituted with one or more R$^{14}$;

R$^e$ is hydrogen, C$_1$-C$_6$ alkyl, C$_1$-C$_6$ deuteroalkyl, C$_1$-C$_6$ fluoroalkyl, C$_{1-6}$ alkoxy, substituted or unsubstituted C$_3$-C$_6$ cycloalkyl, or substituted or unsubstituted C$_2$-C$_6$ heterocycloalkyl;

or R$^d$ and R$^e$ are taken together with the N atom to which they are attached to form a substituted or unsubstituted C$_2$-C$_6$ heterocycloalkyl;

each R$^f$ is independently hydrogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, or substituted or unsubstituted C$_2$-C$_6$heterocycloalkyl;

or both R$^f$ are taken together with the N atom to which they are attached to form a substituted or unsubstituted C$_2$-C$_6$heterocycloalkyl;

R$^g$ is C$_1$-C$_6$ deuteroalkyl, C$_1$-C$_6$ fluoroalkyl, substituted or unsubstituted C$_1$-C$_6$ heteroalkyl, substituted or unsubstituted C$_3$-C$_6$ cycloalkyl, substituted or unsubstituted C$_2$-C$_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted C$_3$-C$_6$ cycloalkyl), -alkyl-(substituted or unsubstituted C$_2$-C$_6$ heterocycloalkyl), —C(═O)R$^{16}$, —C(═O)—OR$^{16}$, —C(═O)N(R$^{16}$)$_2$, —(C(R$^{17}$)$_2$O)$_p$—R$^{15}$, —(CH$_2$CH$_2$O)$_q$—R$^{15}$, or —(C(R$^{17}$)$_2$)$_p$—OR$^{15}$;

Z is N or CR$^8$;

R$^4$, R$^5$, R$^7$, and R$^8$ are each independently hydrogen, halogen, —CN, C$_1$-C$_6$ alkyl, C$_1$-C$_6$ deuteroalkyl, C$_1$-C$_6$ fluoroalkyl, —OR$^{16}$, —C(═O)R$^{16}$, —CO$_2$R$^{16}$, —C(═O)N(R$^{16}$)$_2$, —N(R$^{16}$)$_2$, or —NR$^{16}$C(═O)R$^{16}$;

R$^6$ is hydrogen, halogen, —CN, C$_1$-C$_6$ alkyl, C$_1$-C$_6$ deuteroalkyl, C$_1$-C$_6$ fluoroalkyl, —OR$^{16}$, —C(═O)R$^{16}$, —CO$_2$R$^{16}$, —C(═O)N(R$^{16}$)$_2$, —N(R$^{16}$)$_2$, —NR$^{16}$C(═O)R$^{16}$, substituted or unsubstituted C$_3$-C$_6$ cycloalkyl, substituted or unsubstituted C$_2$-C$_6$heterocycloalkyl, substituted or unsubstituted phenyl, or substituted or unsubstituted heteroaryl; wherein if R$^6$ is substituted then it is substituted with one or more R$^{13}$;

each R$^9$, R$^{10}$, R$^{11}$, R$^{13}$, and R$^{14}$ is independently hydrogen, deuterium, halogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, substituted or unsubstituted C$_2$-C$_6$ heterocycloalkyl, —CN, —OR$^{16}$, —C(═O)R$^{16}$, —CO$_2$R$^{16}$, —C(═O)N(R$^{16}$)$_2$, —N(R$^{16}$)$_2$, or —NR$^{16}$C(═O)R$^{16}$;

R$^{15}$ is hydrogen, substituted or unsubstituted alkyl, substituted or unsubstituted heteroalkyl, substituted or unsubstituted C$_2$-C$_{10}$ heterocycloalkyl, —C(═O)R$^{16}$, —C(═O)—OR$^{16}$, or —C(═O)N(R$^{16}$)$_2$;

each R$^{16}$ is independently hydrogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, substituted or unsubstituted C$_2$-C$_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted C$_3$-C$_6$cycloalkyl), -alkyl-(substituted or unsubstituted C$_2$-C$_6$ heterocycloalkyl);

or both R$^{16}$ are taken together with the N atom to which they are attached to form a substituted or unsubstituted C$_2$-C$_6$ heterocycloalkyl;

each R$^{17}$ is independently hydrogen or C$_1$-C$_6$ alkyl;

m is 1 or 2;

n is 0, 1, 2, 3, or 4;

p is 1, 2, 3, 4, or 5; and q is 1, 2, 3, 4, or 5.

In another embodiment is a compound having the structure of Formula (XXI):

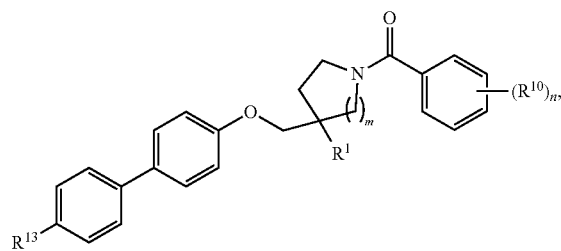

Formula XXI or a pharmaceutically acceptable salt thereof; wherein:

R$^1$ is —C(O)OR$^c$ or —C(O)NR$^d$R$^e$;

R$^c$ is C$_3$-C$_6$ alkyl or R$^g$;

R$^d$ is —CN, C$_1$-C$_6$ alkyl, C$_1$-C$_6$ fluoroalkyl, —OH, —OR$^{1d}$, or —SO$_2$R$^{1d}$;

R$^{1d}$ is substituted or unsubstituted C$_1$-C$_6$ alkyl, substituted or unsubstituted C$_3$-C$_6$ cycloalkyl, substituted or unsubstituted 3- to 6-membered heterocycloalkyl, or substituted or unsubstituted phenyl; wherein if R$^{1d}$ is substituted then it is substituted with one or more R$^{14}$;

R$^e$ is hydrogen or —CH$_3$;

R$^g$ is C$_1$-C$_6$ deuteroalkyl, C$_1$-C$_6$ fluoroalkyl, substituted or unsubstituted C$_1$-C$_6$ heteroalkyl, substituted or unsubstituted C$_3$-C$_6$ cycloalkyl, substituted or unsubstituted C$_2$-C$_6$ heterocycloalkyl, substituted or unsubstituted phenyl, or substituted or unsubstituted heteroaryl;

$R^{10}$ is hydrogen, halogen, —CN, $C_1$-$C_6$ alkyl, $C_1$-$C_6$ fluoroalkyl, or $OR^{16}$;

$R^{13}$ is hydrogen, deuterium, halogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, —CN, —$OR^{16}$, —C(=O)$R^{16}$, —$CO_2R^{16}$, —C(=O)N($R^{16}$)$_2$, —N($R^{16}$)$_2$, or —$NR^{16}$C(=O)$R^{16}$;

$R^{14}$ is hydrogen, halogen, $C_1$-$C_6$ alkyl, —CN, or —$OR^{16}$;

each $R^{16}$ is independently hydrogen, $C_1$-$C_6$ alkyl, $C_1$-$C_6$ deuteroalkyl, $C_1$-$C_6$ fluoroalkyl, or substituted or unsubstituted $C_3$-$C_6$ cycloalkyl;

m is 1 or 2; and n is 0, 1, 2, 3, or 4.

In another embodiment, disclosed herein is a compound of Table 1, Table 2, Table 3, or Table 4, or a pharmaceutically acceptable salt, or solvate, or tautomer thereof.

In another embodiment is a compound of Formula I, Formula I', Formula II, Formula III, Formula IV, Formula V, Formula V', Formula VI, Formula VI', Formula VI-A, Formula VI-A', Formula VI-A", Formula VI-A‴, Formula VI-B, or Formula VI-C, or a pharmaceutically acceptable salt, or solvate, or tautomer thereof.

In another embodiment is a compound of Formula X, Formula XI, Formula XII, Formula XIII, Formula XIII-A, Formula XIII-B, Formula XIII-C, Formula XIV, Formula XV, or Formula XVI, or a pharmaceutically acceptable salt, or solvate, or tautomer thereof.

In another embodiment is a compound of Formula XX, Formula XXI, Formula XXI', Formula XXI", Formula XXI‴, Formula XXII, or a pharmaceutically acceptable salt, or solvate, or tautomer thereof.

In another embodiment is a pharmaceutical composition comprising a compound disclosed herein, or a pharmaceutically acceptable salt, or solvate thereof, and at least one pharmaceutically acceptable excipient.

In another embodiment is a method of modulating the activity of the prostaglandin E2 receptor 2 (EP2) in a mammal comprising administering to the mammal a compound disclosed herein, or a pharmaceutically acceptable salt, or solvate thereof.

In another embodiment is a method of treating a disease or condition that would benefit from the modulation of prostaglandin $E_2$ receptor 2 (EP2) activity comprising administering to the mammal a compound disclosed herein, or a pharmaceutically acceptable salt, or solvate thereof.

Any combination of the groups described above for the various variables is contemplated herein. Throughout the specification, groups and substituents thereof are chosen by one skilled in the field to provide stable moieties and compounds.

In another aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, or nasal administration. In some embodiments, the pharmaceutical composition is in the form of a tablet, a pill, a capsule, a liquid, a suspension, a dispersion, a solution, or an emulsion.

In another aspect, described herein is a method of modulating the activity of the prostaglandin E2 receptor 2 (EP2) in a mammal comprising administering to the mammal a compound described herein, or a pharmaceutically acceptable salt, or solvate thereof.

In yet another aspect, described herein is a method of treating a disease or condition that would benefit from the modulation of prostaglandin E2 receptor 2 (EP2) activity comprising administering to the mammal a compound of described herein, or a pharmaceutically acceptable salt, or solvate thereof.

Other objects, features, and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Prostaglandins act on prostaglandin receptors such as the prostaglandin DP1 receptor (DP1), prostaglandin DP2 receptor (DP2), prostaglandin EP1 receptor (EP1), prostaglandin EP2 receptor (EP2), prostaglandin EP3 receptor (EP3), prostaglandin EP4 receptor (EP4), prostaglandin F2a receptor (FP1), prostacyclin 12 receptor (IP), and thromboxane A2 receptor (TP), or a combination thereof.

Prostaglandin E2 (PGE2) is a metabolite of arachidonic acid, synthesized by the action of cyclooxygenase and prostaglandin E synthase. PGE2, which is produced in nearly all organs and tissues, has a variety of physiological effects, including mucosal protection, induction of gastric acid secretion in stomach, generation of fever, hyperalgesia, inflammation and immunity. The actions of $PGE_2$ are mediated by four receptors, EP1, EP2, EP3 and EP4. PGE2 has affinity not only for all four EP receptor subtypes but also for other prostanoid receptors, such as the PGE2 DP1 receptor.

PGE2 is a downstream product of the cyclooxy-genase 2 (COX-2) pathway and a major modulator of inflammation.

EP2 is a G-protein coupled receptor that, when bound to PGE2, mobilizes $G_s$ proteins and initiates signaling cascades involving adenylyl cyclase (and thereby elevates cAMP) and protein kinase A (PKA). Coupling of EP2 to $G_s$ proteins stimulates adenylate cyclase and their activation increases intracellular cAMP levels. This signaling pathway has implications on inflammation, pain, immunoregulation, mitogenesis, plasticity, and cell injury. EP2 also interacts with β-arrestin/JNK pathways, which pathway can affect proliferation and metastasis.

Expression of EP2 receptors has been demonstrated in a broad range of cell types and tissues, including lung, gastrointestinal tract, kidney, uterus, myleoid and thymus and has been linked with PGE2-mediated vasodilation and smooth muscle relaxation in pulmonary, gastrointestinal and reproductive tracts.

In some embodiments, compounds described herein modulate the activity of EP2. In some embodiments, compounds described herein inhibit or reduce the magnitude of inflammatory PGE2 signalling through the EP2 receptor. In some embodiments, compounds described herein reduce or abolish one or more symptoms associated with an EP2 mediated disease or disorder (e.g., an EP2 mediated inflammatory disease or disorder.)

Abberrant EP2 expression is observed in several forms of cancers, including cancers of the colon, prostate, liver, and breast. EP2 activity (e.g., over-activity) has also been associated with risk factors for cancer including chronic inflammation, immunoregulation, angiogenesis, metastasis, and multidrug resistance. In some embodiments, disclosed herein are methods of treating cancer with a compound disclosed herein. The term "cancer" as used herein, refers to an abnormal growth of cells that tend to proliferate in an uncontrolled way and, in some cases, to metastasize (spread).

In some embodiments, compounds described herein reduce one or more symptoms of an EP2 mediated cancer. In some embodiments, compounds described herein reduce or reverse the progression of an EP2 mediated cancer. In some embodiments, the cancer is a solid tumor. In some embodiments, the cancer is colon cancer.

In some embodiments, EP2 signaling (i.e., through activation by $PGE_2$), contributes to inflammation by enhancing edema and leukocyte infiltration from increased vascular permeability, thereby allowing more blood flow into an inflamed area of the body. In some embodiments, modulation of EP2 function has effects on B lymphocytes, T lymphocytes, cytotoxic T-cell function, or a combination thereof.

In some embodiments, disclosed herein are methods of treating inflammation with a compound disclosed herein. In some embodiments, the compounds disclosed herein are used in the reduction or suppression of inflammation in a mammal. In some embodiments, the compounds disclosed herein are used in the treatment or prevention of inflammation-related conditions (e.g., allergies, pain, and the like).

In some embodiments, disclosed herein is a method of reducing inflammation in a tissue comprising contacting an inflamed cell or tissue with a compound disclosed herein, in an amount sufficient to decrease or inhibit the inflammation. In some embodiments, the inflammation includes an inflammatory or allergic condition.

In some embodiments, disclosed the compounds disclosed herein reduce one or more symptoms of a neuroinflammatory disease or disorder comprising reducing the activity of EP2 (e.g., by contacting the inflamed tissue with an EP2 antagonist disclosed herein). In some embodiments, disclosed herein is a method of reducing or halting the progression of a neuroinflammatory disease or disorder comprising administering a compound disclosed herein to an individual (e.g., a mammal, a human, etc.) in need thereof.

In some embodiments, reducing inflammation, or treatment of an inflammatory condition, includes reducing or inhibiting the activity of EP2. In some embodiments, reducing inflammation, or treatment of an inflammatory condition, includes administering an antagonist of EP2 (e.g., an EP2 antagonist disclosed herein).

In some embodiments, the inflammatory condition is an allergic condition. In some embodiments, the inflammatory condition is asthma. In some embodiments, the inflammatory condition is anaphylaxis. In some embodiments, the inflammatory condition is chronic inflammation. In some embodiments, disclosed herein is a method of treating chronic inflammation comprising administering an EP2 antagonist (e.g., a compound disclosed herein) to the individual in need thereof.

Compounds

Compounds described herein, including pharmaceutically acceptable salts, prodrugs, active metabolites and pharmaceutically acceptable solvates thereof, are EP2 antagonists.

In one aspect, described herein is a compound of Formula (I), or a pharmaceutically acceptable salt, or solvate thereof:

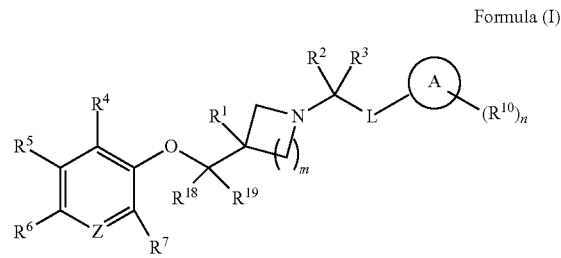

Formula (I)

wherein:
$R^1$ is

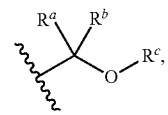

—C(O)NR$^d$R$^e$, —N(R$^f$)$_2$, substituted or unsubstituted monocyclic heterocycle, or substituted or unsubstituted monocyclic carbocycle, wherein if $R^1$ is a substituted monocyclic heterocycle, then it is substituted with one or more instances of $R^9$;

$R^a$ is hydrogen, deuterium, $C_1$-$C_6$ alkyl, $C_1$-$C_6$ deuteroalkyl, $C_1$-$C_6$ fluoroalkyl;

$R^b$ is hydrogen, deuterium, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$ heterocycloalkyl;

or $R^a$ and $R^b$ are taken together with the carbon atom to which they are attached to form a ring C that is a substituted or unsubstituted $C_3$-$C_6$cycloalkyl, or substituted or unsubstituted $C_2$-$C_6$ heterocycloalkyl, wherein if the ring C is substituted then it is substituted with one or more $R^{11}$; and $R^c$ is hydrogen, $C_1$-$C_6$ alkyl, or $R^g$;

or $R^a$ and $R^b$ are taken together with the carbon atom to which they are attached to form a carbonyl (C=O); and $R^c$ is $C_3$-$C_6$ alkyl or $R^g$;

$R^d$ is —CN, $C_1$-$C_6$ alkyl, $C_1$-$C_6$ deuteroalkyl, $C_1$-$C_6$ fluoroalkyl, $C_{1-6}$ alkoxy, substituted or unsubstituted $C_3$-$C_6$ cycloalkyl, substituted or unsubstituted $C_2$-$C_6$ heterocycloalkyl, OH, OR$^{1d}$, —SOR$^{1d}$, or —SO$_2$R$^{1d}$; wherein R$^{1d}$ is substituted or unsubstituted $C_1$-$C_6$ alkyl, substituted or unsubstituted $C_3$-$C_6$ cycloalkyl, substituted or unsubstituted 3- to 6-membered heterocycloalkyl, substituted or unsubstituted phenyl, or substituted or unsubstituted 5- to 6-membered heteroaryl; wherein if R$^{1d}$ is substituted then it is substituted with one or more R$^{14}$;

$R^e$ is hydrogen, $C_1$-$C_6$ alkyl, $C_1$-$C_6$ deuteroalkyl, $C_1$-$C_6$ fluoroalkyl, $C_{1-6}$ alkoxy, substituted or unsubstituted $C_3$-$C_6$ cycloalkyl, or substituted or unsubstituted $C_2$-$C_6$ heterocycloalkyl;

or $R^d$ and $R^e$ are taken together with the N atom to which they are attached to form a substituted or unsubstituted $C_2$-$C_6$ heterocycloalkyl;

each $R^f$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$heterocycloalkyl;
or both $R^f$ are taken together with the N atom to which they are attached to form a substituted or unsubstituted $C_2$-$C_6$heterocycloalkyl;

$R^g$ is $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$ cycloalkyl), -alkyl-(substituted or unsubstituted $C_2$-$C_6$ heterocycloalkyl), —C(=O)$R^{16}$, —C(=O)—O$R^{16}$, —C(=O)N($R^{16}$)$_2$, —(C($R^{17}$)$_2$O)$_p$—$R^1$, —(CH$_2$CH$_2$O)$_q$—$R^1$, or —(C($R^{17}$)$_2$)$_p$—O$R^{15}$;

p is 1, 2, 3, 4, or 5;
q is 1, 2, 3, 4, or 5;
each $R^{17}$ is independently hydrogen or $C_1$-$C_6$ alkyl;
$R^{15}$ is hydrogen, substituted or unsubstituted alkyl, substituted or unsubstituted heteroalkyl, substituted or unsubstituted $C_2$-$C_{10}$ heterocycloalkyl, —C(=O)$R^{16}$, —C(=O)—O$R^{16}$, or —C(=O)N($R^{16}$)$_2$;
$R^2$ is hydrogen, $C_1$-$C_6$ alkyl, $C_1$-$C_6$ deuteroalkyl, or $C_1$-$C_6$fluoroalkyl;
$R^3$ is hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$ heterocycloalkyl;
or $R^2$ and $R^3$ are taken together with the carbon atom to which they are attached to form a carbonyl (C=O) or thiocarbonyl (C=S);
or $R^2$ and $R^3$ are taken together with the carbon atom to which they are attached to form a ring B that is a substituted or unsubstituted $C_3$-$C_6$ cycloalkyl, or substituted or unsubstituted $C_2$-$C_6$ heterocycloalkyl, wherein if the ring B is substituted then it is substituted with one or more $R^{12}$;
Z is N or C$R^8$;
L is absent or —NH—;
$R^4$, $R^5$, $R^7$, and $R^8$ are each independently hydrogen, halogen, —CN, $C_1$-$C_6$ alkyl, $C_1$-$C_6$ deuteroalkyl, $C_1$-$C_6$ fluoroalkyl, —O$R^{16}$, —C(=O)$R^{16}$, —CO$_2R^{16}$, —C(=O)N($R^{16}$)$_2$, —N($R^{16}$)$_2$, or —N$R^{16}$C(=O)$R^{16}$;
$R^6$ is hydrogen, halogen, —CN, $C_1$-$C_6$ alkyl, $C_1$-$C_6$ deuteroalkyl, $C_1$-$C_6$ fluoroalkyl, —O$R^{16}$, —C(=O)$R^{16}$, —CO$_2R^{16}$, —C(=O)N($R^{16}$)$_2$, —N($R^{16}$)$_2$, —N$R^{16}$C(=O)$R^{16}$, substituted or unsubstituted $C_3$-$C_6$ cycloalkyl, substituted or unsubstituted $C_2$-$C_6$heterocycloalkyl, substituted or unsubstituted phenyl, or substituted or unsubstituted heteroaryl; wherein if $R^6$ is substituted then it is substituted with one or more $R^{13}$;
ring A is a substituted or unsubstituted phenyl, or substituted or unsubstituted heteroaryl;
each $R^9$, $R^{10}$, $R^{11}$, $R^{12}$, $R^{13}$, and $R^{14}$ is independently hydrogen, deuterium, halogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, —CN, —O$R^{16}$, —C(=O)$R^{16}$, —CO$_2R^{16}$, —C(=O)N($R^{16}$)$_2$, —N($R^{16}$)$_2$, or —N$R^{16}$C(=O)$R^{16}$;
each $R^{16}$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), -alkyl-(substituted or unsubstituted $C_2$-$C_6$ heterocycloalkyl);
or both $R^{16}$ are taken together with the N atom to which they are attached to form a substituted or unsubstituted $C_2$-$C_6$ heterocycloalkyl;
$R^{18}$ and $R^{19}$ are each independently hydrogen, deuterium, $C_1$-$C_6$ alkyl, $C_1$-$C_6$ deuteroalkyl, or $C_1$-$C_6$ fluoroalkyl;
or $R^{18}$ and $R^{19}$ are taken together with the carbon atom to which they are attached to form a ring E that is a $C_3$-$C_6$cycloalky, or $C_2$-$C_6$ heterocycloalkyl;
m is 1 or 2; and
n is 0, 1, 2, 3, or 4.

In another aspect, described herein is a compound of Formula (I'), or a pharmaceutically acceptable salt, or solvate thereof:

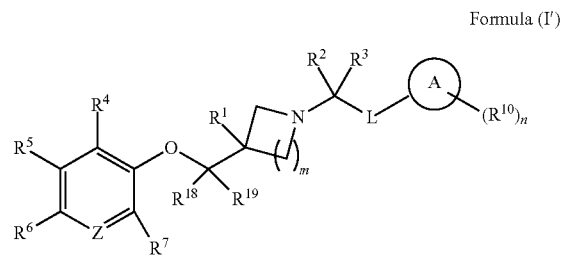

Formula (I')

wherein:
$R^1$ is

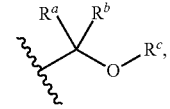

—C(O)N$R^dR^e$, —N($R^f$)$_2$, substituted or unsubstituted monocyclic heterocycle, or substituted or unsubstituted monocyclic carbocycle, wherein if $R^1$ is a substituted monocyclic heterocycle, then it is substituted with one or more instances of $R^9$;
$R^a$ is hydrogen, deuterium, $C_1$-$C_6$ alkyl, $C_1$-$C_6$ deuteroalkyl, or $C_1$-$C_6$ fluoroalkyl;
$R^b$ is hydrogen, deuterium, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$ heterocycloalkyl;
or $R^a$ and $R^b$ are taken together with the carbon atom to which they are attached to form a ring C that is a substituted or unsubstituted $C_3$-$C_6$cycloalkyl, or substituted or unsubstituted $C_2$-$C_6$ heterocycloalkyl, wherein if the ring C is substituted then it is substituted with one or more $R^{11}$; and $R^c$ is hydrogen, $C_1$-$C_6$ alkyl, or $R^g$;
or $R^a$ and $R^b$ are taken together with the carbon atom to which they are attached to form a carbonyl (C=O); and $R^c$ is $C_3$-$C_6$ alkyl or $R^g$;
$R^d$ is $C_1$-$C_6$ alkyl, $C_1$-$C_6$ deuteroalkyl, $C_1$-$C_6$ fluoroalkyl, $C_{1-6}$ alkoxy, substituted or unsubstituted $C_3$-$C_6$ cycloalkyl, or substituted or unsubstituted $C_2$-$C_6$ heterocycloalkyl;
$R^e$ is hydrogen, $C_1$-$C_6$ alkyl, $C_1$-$C_6$ deuteroalkyl, $C_1$-$C_6$ fluoroalkyl, $C_{1-6}$ alkoxy, substituted or unsubstituted $C_3$-$C_6$ cycloalkyl, or substituted or unsubstituted $C_2$-$C_6$ heterocycloalkyl;

or $R^d$ and $R^e$ are taken together with the N atom to which they are attached to form a substituted or unsubstituted $C_2$-$C_6$ heterocycloalkyl;

each $R^f$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$ heterocycloalkyl;

or both $R^f$ are taken together with the N atom to which they are attached to form a substituted or unsubstituted $C_2$-$C_6$ heterocycloalkyl;

$R^g$ is $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$ cycloalkyl), -alkyl-(substituted or unsubstituted $C_2$-$C_6$ heterocycloalkyl), —C(=O)$R^{16}$, —C(=O)—O$R^{16}$, —C(=O)N($R^{16}$)$_2$, —(C($R^{17}$)$_2$O)$_p$—$R^{15}$, —(CH$_2$CH$_2$O)$_q$—$R^{15}$, or —(C($R^{17}$)$_2$)$_p$—O$R^{15}$;

p is 1, 2, 3, 4, or 5;

q is 1, 2, 3, 4, or 5;

each $R^{17}$ is independently hydrogen or $C_1$-$C_6$ alkyl;

$R^{15}$ is hydrogen, substituted or unsubstituted alkyl, substituted or unsubstituted heteroalkyl, substituted or unsubstituted $C_2$-$C_{10}$ heterocycloalkyl, —C(=O)$R^{16}$, —C(=O)—O$R^{16}$, or —C(=O)N($R^{16}$)$_2$;

$R^2$ is hydrogen, $C_1$-$C_6$ alkyl, $C_1$-$C_6$ deuteroalkyl, or $C_1$-$C_6$ fluoroalkyl;

$R^3$ is hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$ heterocycloalkyl;

or $R^2$ and $R^3$ are taken together with the carbon atom to which they are attached to form a carbonyl (C=O) or thiocarbonyl (C=S);

or $R^2$ and $R^3$ are taken together with the carbon atom to which they are attached to form a ring B that is a substituted or unsubstituted $C_3$-$C_6$ cycloalkyl, or substituted or unsubstituted $C_2$-$C_6$ heterocycloalkyl, wherein if the ring B is substituted then it is substituted with one or more $R^{12}$;

Z is N or $CR^8$;

L is absent or —NH—;

$R^4$, $R^5$, $R^7$, and $R^8$ are each independently hydrogen, halogen, —CN, $C_1$-$C_6$ alkyl, $C_1$-$C_6$ deuteroalkyl, $C_1$-$C_6$ fluoroalkyl, —O$R^{16}$, —C(=O)$R^{16}$, —CO$_2R^{16}$, —C(=O)N($R^{16}$)$_2$, —N($R^{16}$)$_2$, or —N$R^{16}$C(=O)$R^{16}$;

$R^6$ is hydrogen, halogen, —CN, $C_1$-$C_6$ alkyl, $C_1$-$C_6$ deuteroalkyl, $C_1$-$C_6$ fluoroalkyl, —O$R^{16}$, —C(=O)$R^{16}$, —CO$_2R^{16}$, —C(=O)N($R^{16}$)$_2$, —N($R^{16}$)$_2$, —N$R^{16}$C(=O)$R^{16}$, substituted or unsubstituted $C_3$-$C_6$ cycloalkyl, substituted or unsubstituted $C_2$-$C_6$ heterocycloalkyl, substituted or unsubstituted phenyl, or substituted or unsubstituted heteroaryl; wherein if $R^6$ is substituted then it is substituted with one or more $R^{13}$;

or $R^5$ and $R^6$ are taken together, with the intervening atoms to which they are attached, to form a fused ring D that is a substituted or unsubstituted 5- or 6-membered carbocycle or substituted or unsubstituted 5- or 6-membered heterocycle, wherein if ring D is substituted then it is substituted with one or more $R^{14}$;

ring A is a substituted or unsubstituted phenyl, or substituted or unsubstituted heteroaryl;

each $R^9$, $R^{10}$, $R^{11}$, $R^{12}$, $R^{13}$, and $R^{14}$ is independently hydrogen, deuterium, halogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, —CN, —O$R^{16}$, —C(=O)$R^{16}$, —CO$_2R^{16}$, —C(=O)N($R^{16}$)$_2$, —N($R^{16}$)$_2$, or —N$R^{16}$C(=O)$R^{16}$;

each $R^{16}$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$ cycloalkyl), -alkyl-(substituted or unsubstituted $C_2$-$C_6$ heterocycloalkyl);

or both $R^{16}$ are taken together with the N atom to which they are attached to form a substituted or unsubstituted $C_2$-$C_6$ heterocycloalkyl;

$R^{18}$ and $R^{19}$ are each independently hydrogen, deuterium, $C_1$-$C_6$ alkyl, $C_1$-$C_6$ deuteroalkyl, or $C_1$-$C_6$ fluoroalkyl;

or $R^{18}$ and $R^{19}$ are taken together with the carbon atom to which they are attached to form a ring E that is a $C_3$-$C_6$cycloalky, or $C_2$-$C_6$ heterocycloalkyl;

m is 1 or 2; and n is 0, 1, 2, 3, or 4.

For any and all of the embodiments, substituents are selected from among a subset of the listed alternatives. For example, in some embodiments, ring A is an unsubstituted or substituted phenyl, unsubstituted or substituted pyridinyl, unsubstituted or substituted pyrimidinyl, unsubstituted or substituted pyrazinyl, unsubstituted or substituted pyridazinyl, or unsubstituted or substituted triazinyl. In some embodiments, ring A is an unsubstituted or substituted phenyl. In some embodiments, ring A is an unsubstituted or substituted pyridinyl. In some embodiments, ring A is an unsubstituted or substituted pyrimidinyl. In some embodiments, ring A is an unsubstituted or substituted pyrazinyl. In some embodiments, ring A is an unsubstituted or substituted pyridazinyl. In some embodiments, ring A is an unsubstituted or substituted triazinyl.

In some embodiments, ring A is an unsubstituted or substituted phenyl, or unsubstituted or substituted pyridinyl. In some embodiments, ring A is an unsubstituted phenyl. In some embodiments, ring A is a substituted pyridinyl. In some embodiments, ring A is an unsubstituted phenyl. In some embodiments, ring A is a substituted pyridinyl. In some embodiments, ring A is a substituted phenyl or a substituted pyridinyl. In some embodiments, ring A is a substituted phenyl or a substituted pyridinyl, wherein the substituted phenyl or substituted pyridinyl is substituted with n instances of $R^{10}$. In some embodiments, ring A is a substituted phenyl or a substituted pyridinyl, wherein the substituted phenyl or substituted pyridinyl is substituted with 1 $R^{10}$.

In some embodiments, ring A is a substituted phenyl or a substituted pyridinyl, wherein the substituted phenyl or substituted pyridinyl is substituted with hydrogen, deuterium, substituted or unsubstituted $C_3$-$C_6$ cycloalkyl, F, Cl, Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$F, —CHF$_2$, —CF$_3$, —CH$_2$CF$_3$, —CH$_2$D, —CHD$_2$, —CD$_3$, —OH, —OCH$_3$, —OCH$_2$CH$_3$, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, or —N(CH$_3$)$_2$. In some embodiments, ring A is a substituted phenyl or a substituted pyridinyl, wherein the substituted phenyl or substituted pyridinyl is substituted with halogen, $C_{1-6}$ alkyl, $C_{1-6}$ fluoroalkyl, or CN. In some embodiments, ring A is a substituted phenyl or a substituted pyridinyl, wherein the substituted phenyl or substitute pyridinyl is substituted with —F, —Cl, —Br, —I, —CH$_3$, —CF$_3$, or —CN. In some embodiments, ring A is a phenyl ring substituted with —F, —Cl, —CF$_3$, or —CN. In some embodiments, ring A is a phenyl ring substituted with —F or —Cl. In some embodiments, ring A is a phenyl ring substituted with —F. In some embodiments, ring A is a phenyl ring substituted with —Cl. In some embodiments, ring A is a phenyl ring substituted with —CF$_3$. In some embodiments, ring A is a phenyl ring substituted with —CN. In some embodiments, ring A is a pyridinyl ring substituted with —F or —Cl. In some embodiments, ring A is a pyridinyl ring substituted with —F. In some embodiments, ring A is a pyridinyl ring substituted with —Cl. In some embodiments, ring A is a pyridinyl ring substituted with —CF$_3$. In some embodiments, ring A is a pyridinyl ring substituted with —CN.

In some embodiments,

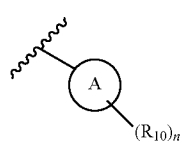

is

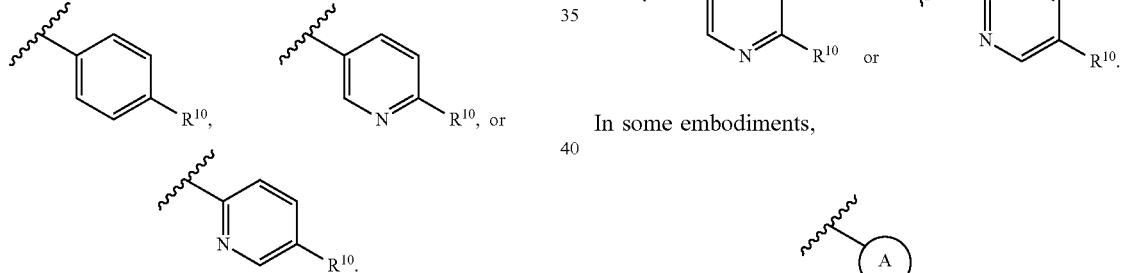

In some embodiments,

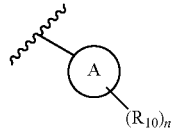

is

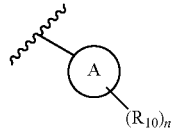

In some embodiments,

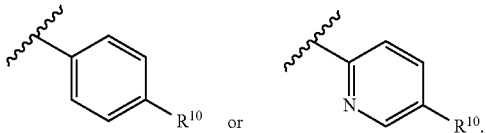

In some embodiments,

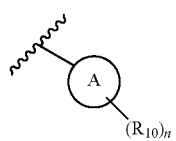

is

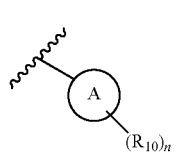

In some embodiments,

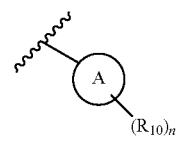

is

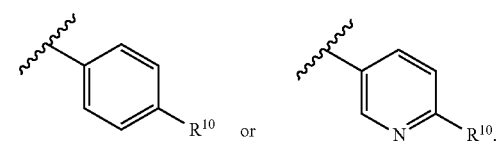

In some embodiments,

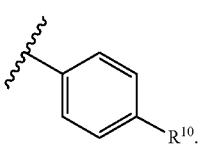

is

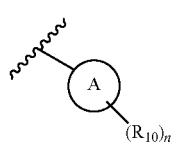

In some embodiments, is

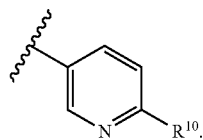

In some embodiments,

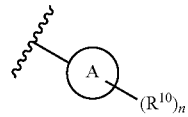

is

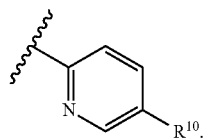

In some embodiments, L is absent or —NH—. In some embodiments, L is —NH—. In some embodiments, L is absent.

In some embodiments, $R^{18}$ and $R^{19}$ are each independently hydrogen, deuterium, $C_1$-$C_6$ alkyl, $C_1$-$C_6$ deuteroalkyl, or $C_1$-$C_6$ fluoroalkyl; or $R^{18}$ and $R^{19}$ are taken together with the carbon atom to which they are attached to form a ring E that is a $C_3$-$C_6$cycloalky, or $C_2$-$C_6$ heterocycloalkyl. In some embodiments, $R^{18}$ and $R^{19}$ are each independently hydrogen, deuterium, or —CH$_3$. In some embodiments, $R^{18}$ and $R^{19}$ are each hydrogen. In some embodiments, $R^{18}$ and $R^{19}$ are each deuterium. In some embodiments, $R^{18}$ and $R^{19}$ are each —CH$_3$. In some embodiments, one of $R^{18}$ and $R^{19}$ is hydrogen, and the other is deuterium or —CH$_3$. In some embodiments, one of $R^{18}$ and $R^{19}$ is hydrogen, and the other is deuterium. In some embodiments, one of $R^{18}$ and $R^{19}$ is hydrogen, and the other is —CH$_3$. In some embodiments, $R^{18}$ and $R^{19}$ are taken together with the carbon atom to which they are attached to form a ring E that is a $C_3$-$C_6$cycloalky, or $C_2$-$C_6$ heterocycloalkyl. In some embodiments, $R^{18}$ and $R^{19}$ are taken together with the carbon atom to which they are attached to form a ring E that is a cyclopropyl, cyclobutyl, azirane, azetidine, oxirane, or oxetane. In some embodiments, $R^{18}$ and $R^{19}$ are taken together with the carbon atom to which they are attached to form a ring E that is a cyclopropyl, azetidine, or oxetane. In some embodiments, $R^{18}$ and $R^{19}$ are taken together with the carbon atom to which they are attached to form a ring E that is a cyclopropyl. In some embodiments, $R^{18}$ and $R^{19}$ are taken together with the carbon atom to which they are attached to form a ring E that is an azetidine. In some embodiments, $R^{18}$ and $R^{19}$ are taken together with the carbon atom to which they are attached to form a ring E that is an oxetane.

In some embodiments, L is —NH— and each $R^{18}$ and $R^{19}$ is hydrogen. In some embodiments, L is absent and each $R^{18}$ and $R^{19}$ is hydrogen. In some embodiments, L is —NH— and each $R^{18}$ and $R^{19}$ is deuterium. In some embodiments, L is absent and each $R^{18}$ and $R^{19}$ is deuterium. In some embodiments, L is —NH— and $R^{18}$ and $R^{19}$ are taken together with the carbon atom to which they are attached to form a ring E that is a cyclopropyl, azetidine, or oxetane. In some embodiments, L is absent and $R^{18}$ and $R^{19}$ are taken together with the carbon atom to which they are attached to form a ring E that is a cyclopropyl, azetidine, or oxetane.

In some embodiments, the compound of Formula (I) has the following structure of Formula (II):

Formula (II)

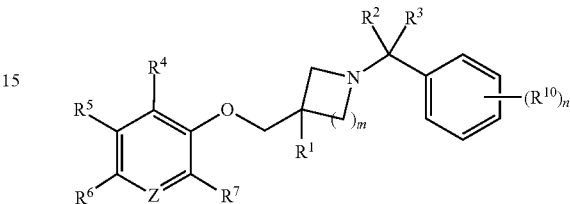

or a pharmaceutically acceptable salt, or solvate thereof.

In some embodiments, m is 1 or 2. In some embodiments, m is 1. In some embodiments, the compound of Formula (I) has the following structure of Formula (III):

Formula (III)

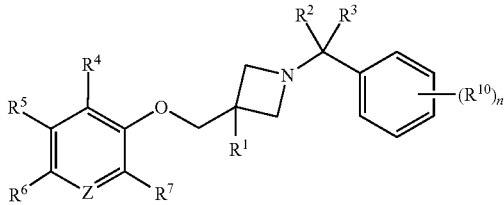

or a pharmaceutically acceptable salt, or solvate thereof.

In some embodiments, m is 2. In some embodiments, the compound of Formula (I) has the following structure of Formula (IV):

Formula (IV)

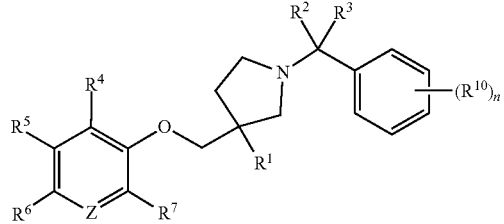

or a pharmaceutically acceptable salt, or solvate thereof.

In some embodiments, each $R^{10}$ is independently hydrogen, deuterium, substituted or unsubstituted $C_3$-$C_6$ cycloalkyl, F, Cl, Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$F, —CHF$_2$, —CF$_3$, —CH$_2$CF$_3$, —CH$_2$D, —CHD$_2$, —CD$_3$, —OH, —OCH$_3$, —OCH$_2$CH$_3$, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, or —N(CH$_3$)$_2$. In some embodiments, ring A is a phenyl ring substituted with hydrogen, deuterium, substituted or unsubstituted $C_3$-$C_6$ cycloalkyl, F, Cl, Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$F, —CHF$_2$, —CF$_3$, —CH$_2$CF$_3$, —CH$_2$D, —CHD$_2$, —CD$_3$, —OH, —OCH$_3$, —OCH$_2$CH$_3$, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, or —N(CH$_3$)$_2$. In some embodiments, each R$^{10}$ is independently hydrogen, F, Cl, Br, —CN, —CH$_3$, —CH$_2$CH$_3$, —CH$_2$CN, —CH$_2$F, —CHF$_2$, —CF$_3$, —OH, —OCH$_3$, —OCH$_2$CH$_3$, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, or —N(CH$_3$)$_2$. In some embodiments, each R$^{10}$ is independently hydrogen, —F, —Cl, —Br, —CN, —CH$_3$, —CH$_2$F, —CHF$_2$, —CF$_3$, —OCF$_3$, —C(=O)NH$_2$, —C(=O)NHCH$_3$, —C(=O)N(CH$_3$)$_2$, —NH$_2$, —NHCH$_3$, or —N(CH$_3$)$_2$. In some embodiments, each R$^{10}$ is independently —F, —Cl, —Br, —CN, —CH$_3$, —CH$_2$F, —CHF$_2$, —CF$_3$, —OCF$_3$, —C(=O)NH$_2$, —C(=O)NHCH$_3$, —C(=O)N(CH$_3$)$_2$, —NH$_2$, —NHCH$_3$, or —N(CH$_3$)$_2$. In some embodiments, each R$^{10}$ is independently —F, —Cl, —Br, —CN, —CH$_3$, —CH$_2$F, —CHF$_2$, —CF$_3$, or —OCF$_3$. In some embodiments, each R$^{10}$ is independently —F, —Cl, —CN, —CH$_3$, or —CF$_3$. In some embodiments, each R$^{10}$ is independently —F, —Cl, or —CN. In some embodiments, each R$^{10}$ is independently —F or —Cl. In some embodiments, R$^{10}$ is —F. In some embodiments, R$^{10}$ is —Cl. In some embodiments, R$^{10}$ is —CN. In some embodiments, R$^{10}$ is —CF$_3$. In some embodiments, R$^{10}$ is —CH$_3$. In some embodiments, R$^{10}$ is —OCF$_3$.

In some embodiments, R$^1$ is a substituted or unsubstituted monocyclic heterocycle, or substituted or unsubstituted monocyclic carbocycle, wherein if R$^1$ is a substituted monocyclic heterocycle, then it is substituted with one or more instances of R$^9$. In some embodiments, R$^1$ is a substituted or unsubstituted monocyclic heterocycle. In some embodiments, R$^1$ is an unsubstituted monocyclic heterocycle. In some embodiments, R$^1$ is a monocyclic heterocycle substituted with one or more instances of R$^9$. In some embodiments, R$^1$ is a monocyclic heteroaryl substituted with one or more instances of R$^9$. In some embodiments, R$^1$ is a monocyclic heterocycloalkyl substituted with one or more instances of R$^9$. In some embodiments, R$^1$ is a 5- or 6-membered monocyclic heteroaryl substituted with one or more instances of R$^9$. In some embodiments, R$^1$ is a 5- or 6-membered monocyclic heterocycloalkyl substituted with one or more instances of R$^9$. In some embodiments, R$^1$ is an unsubstituted 5- or 6-membered monocyclic heterocycle. In some embodiments, R$^1$ is an unsubstituted 5- or 6-membered monocyclic heteroaryl. In some embodiments, R$^1$ is an unsubstituted 5- or 6-membered monocyclic heterocycloalkyl.

In some embodiments, R$^1$ is

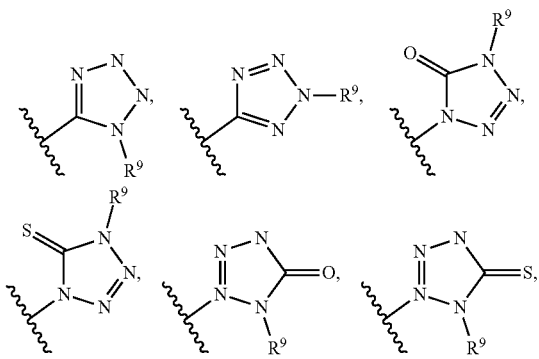

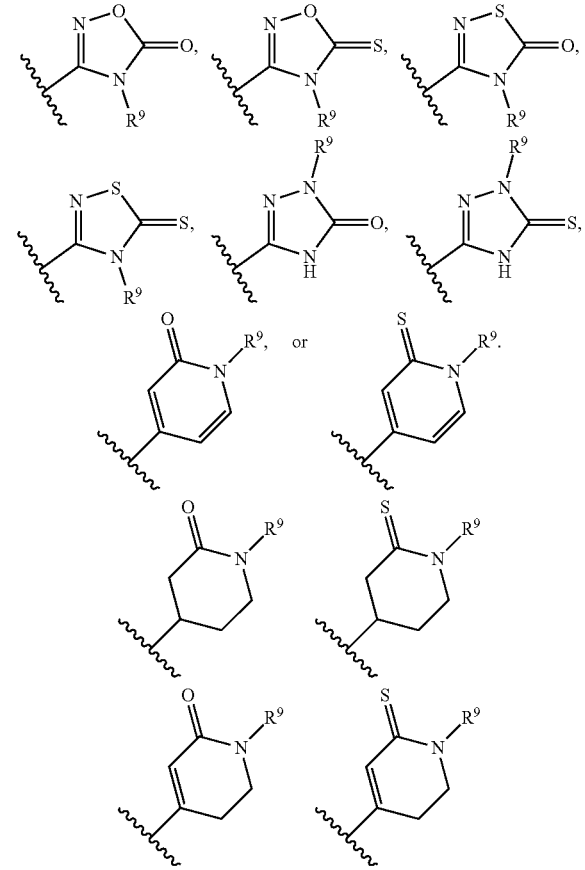

In some embodiments, R$^1$ is a 5-membered monocyclic heteroaryl substituted with one or more instances of R$^9$. In some embodiments, R$^1$ is a 5-membered monocyclic heterocycloalkyl substituted with one or more instances of R$^9$. In some embodiments, R$^1$ is an unsubstituted 5-membered monocyclic heterocycle. In some embodiments, R$^1$ is an unsubstituted 5-membered monocyclic heteroaryl. In some embodiments, R$^1$ is an unsubstituted 5-membered monocyclic heterocycloalkyl.

In some embodiments, R$^1$ is

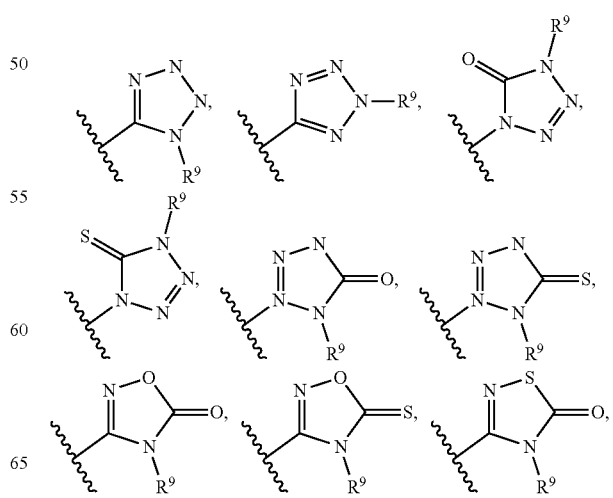

-continued

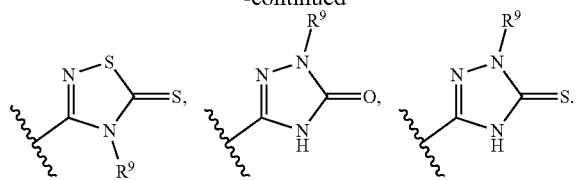

In some embodiments, $R^1$ is

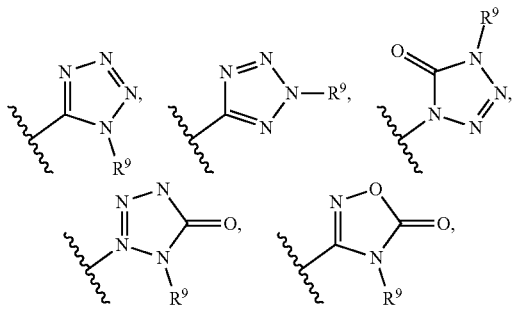

In some embodiments, $R^1$ is

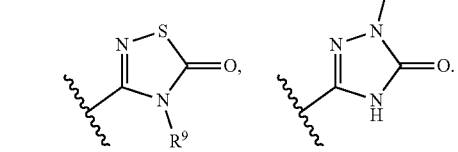

In some embodiments, $R^1$ is

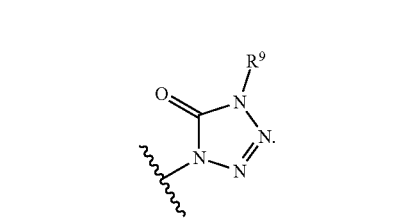

In some embodiments, each $R^9$ is independently hydrogen, deuterium, halogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, —CN, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$. In some embodiments, each $R^9$ is independently hydrogen, deuterium, or $C_1$-$C_6$ alkyl. In some embodiments, each $R^9$ is independently hydrogen or $C_1$-$C_6$ alkyl. In some embodiments, each $R^9$ is $C_1$-$C_6$ alkyl. In some embodiments, each $R^9$ is independently hydrogen, —CH$_3$, —CH$_2$CH$_3$, —(CH$_2$)$_2$CH$_3$, —(CH$_2$)$_3$CH$_3$, —CH(CH$_3$)$_2$, or —C(CH$_3$)$_3$. In some embodiments, each $R^9$ is independently hydrogen or —CH$_3$. In some embodiments, each $R^9$ is —CH$_3$. In some embodiments, each $R^9$ is hydrogen.

In some embodiments, $R^1$ is

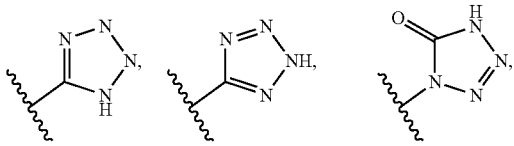

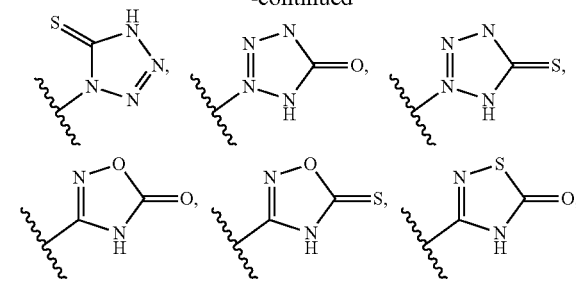

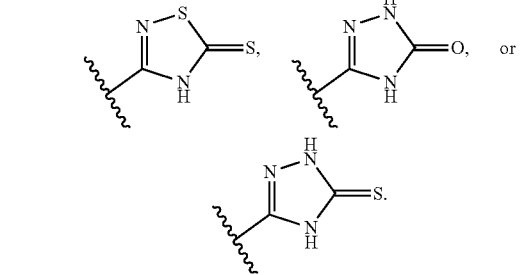

In some embodiments, $R^1$ is

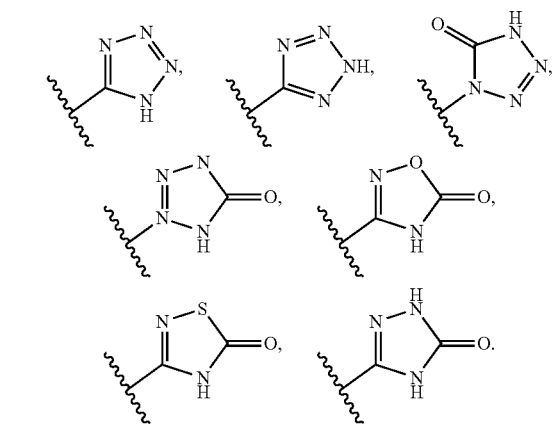

In some embodiments, $R^1$ is

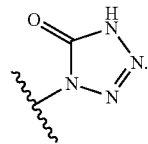 [SMILES: *n1nn[nH]c1=O]

In some embodiments, $R^1$ is

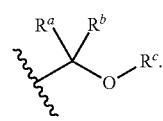

In some embodiments, $R^a$ is hydrogen, deuterium, $C_1$-$C_6$ alkyl, $C_1$-$C_6$ deuteroalkyl, or $C_1$-$C_6$ fluoroalkyl. In some embodiments, $R^a$ is hydrogen, —CH$_3$, —CH$_2$CH$_3$, —CD$_3$, —CH$_2$CD$_3$, —CF$_3$, or —CH$_2$CF$_3$. In some embodiments, $R^b$ is hydrogen, deuterium, $C_1$-$C_6$ alkyl, $C_1$-$C_6$ deuteroalkyl, or $C_1$-$C_6$ fluoroalkyl. In some embodiments, $R^b$ is hydrogen, —$CH_3$, —$CH_2CH_3$, —$CD_3$, —$CH_2CD_3$, —$CF_3$, or —$CH_2CF_3$. In some embodiments, $R^a$ is hydrogen or deuterium. In some embodiments, $R^b$ is hydrogen or deuterium. In some embodiments, $R^a$ and $R^b$ are taken together with the carbon atom to which they are attached to form a ring C that is a substituted or unsubstituted oxetane, substituted or unsubstituted thietane 1,1-dioxide, or substituted or unsubstituted azetidine. In some embodiments, $R^a$ and $R^b$ are taken together with the carbon atom to which they are attached to form a ring C that is an unsubstituted oxetane, unsubstituted thietane 1,1-dioxide, or unsubstituted azetidine. In some embodiments, $R^a$ and $R^b$ are taken together with the carbon atom to which they are attached to form a ring C that is a substituted oxetane, substituted thietane 1,1-dioxide, or substituted azetidine. In some embodiments, $R^a$ and $R^b$ are taken together with the carbon atom to which they are attached to form a ring C that is a substituted or unsubstituted oxetane. In some embodiments, $R^a$ and $R^b$ are taken together with the carbon atom to which they are attached to form a ring C that is a substituted or unsubstituted thietane 1,1-dioxide. In some embodiments, $R^a$ and $R^b$ are taken together with the carbon atom to which they are attached to form a ring C that is a substituted or unsubstituted azetidine.

In some embodiments, $R^c$ is hydrogen, $C_1$-$C_6$alkyl, $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), -alkyl-(substituted or unsubstituted $C_2$-$C_6$heterocycloalkyl), —$C(=O)R^{16}$, —$C(=O)$—$OR^{16}$, —$C(=O)N(R^{16})_2$, —$(CH_2O)_p$—$R^{15}$, or —$(CH(CH_3)O)_p$—$R^{15}$. In some embodiments, $R^c$ is hydrogen or $C_1$-$C_6$ alkyl. In some embodiments, $R^c$ is hydrogen. In some embodiments, $R^c$ is $C_1$-$C_6$ alkyl. In some embodiments, $R^c$ is —$CH_3$, —$CH_2CH_3$, —$(CH_2)_2CH_3$, —$(CH_2)_3CH_3$, —$CH(CH_3)_2$, or —$C(CH_3)_3$. In some embodiments, $R^c$ is —$CH_3$. In some embodiments, $R^c$ is —$CH_2CH_3$. In some embodiments, $R^c$ is $C_3$-$C_6$ alkyl. In some embodiments, $R^c$ is —$(CH_2)_2CH_3$, —$(CH_2)_3CH_3$, —$CH(CH_3)_2$, or —$C(CH_3)_3$. In some embodiments, $R^c$ is $R^g$.

In some embodiments, $R^a$ and $R^b$ are taken together with the carbon atom to which they are attached to form a carbonyl (C=O); and $R^c$ is $C_3$-$C_6$ alkyl or $R^g$. In some embodiments, $R^a$ and $R^b$ are taken together with the carbon atom to which they are attached to form a carbonyl (C=O); and $R^c$ is —$(CH_2)_2CH_3$, —$(CH_2)_3CH_3$, —$(CH_2)_4CH_3$, —$(CH_2)_5CH_3$, —$CH(CH_3)_2$, or —$C(CH_3)_3$.

In some embodiments, $R^a$ and $R^b$ are taken together with the carbon atom to which they are attached to form a carbonyl (C=O); $R^c$ is $R^g$; and $R^g$ is $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$ cycloalkyl), -alkyl-(substituted or unsubstituted $C_2$-$C_6$ heterocycloalkyl), —$C(=O)R^{16}$, —$C(=O)$—$OR^{16}$, —$C(=O)N(R^{16})_2$, —$(C(R^{17})_2O)_p$—$R^{15}$, —$(CH_2CH_2O)_q$—$R^{15}$, or —$(C(R^7)_2)_p$—$OR^{15}$.

In some embodiments, $R^a$ and $R^b$ are taken together with the carbon atom to which they are attached to form a carbonyl (C=O); $R^c$ is $R^g$; and $R^g$ is $C_1$-$C_6$ deuteroalkyl, $C_1$-$C_6$ fluoroalkyl, or substituted or unsubstituted $C_1$-$C_6$ heteroalkyl. In some embodiments, $R^a$ and $R^b$ are taken together with the carbon atom to which they are attached to form a carbonyl (C=O); $R^c$ is $R^g$; and $R^g$ is —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^a$ and $R^b$ are taken together with the carbon atom to which they are attached to form a carbonyl (C=O); $R^c$ is $R^g$; and $R^g$ is —$CD_3$, —$CD_2CD_3$, —$CF_3$, or —$CF_2CF_3$. In some embodiments, $R^a$ and $R^b$ are taken together with the carbon atom to which they are attached to form a carbonyl (C=O); $R^c$ is $R^g$; and $R^g$ is —$CD_3$, or —$CD_2CD_3$.

In some embodiments, $R^a$ and $R^b$ are taken together with the carbon atom to which they are attached to form a carbonyl (C=O); $R^c$ is $R^g$; and $R^g$ is -alkyl-(substituted or unsubstituted phenyl), -alkyl-(substituted or unsubstituted heteroaryl), -alkyl-(substituted or unsubstituted $C_3$-$C_6$ cycloalkyl), -alkyl-(substituted or unsubstituted $C_2$-$C_6$ heterocycloalkyl).

In some embodiments, $R^a$ and $R^b$ are taken together with the carbon atom to which they are attached to form a carbonyl (C=O); $R^c$ is $R^g$; and $R^g$ is —$C(=O)R^{16}$, —$C(=O)$—$OR^{16}$, —$C(=O)N(R^{16})_2$, —$(C(R^{17})_2O)_p$—$R^{15}$, —$(CH_2CH_2O)_q$—$R^{15}$, or —$(C(R^{17})_2)_p$—$OR^{15}$. In some embodiments, $R^a$ and $R^b$ are taken together with the carbon atom to which they are attached to form a carbonyl (C=O); $R^c$ is $R^g$; and $R^g$ is —$C(=O)R^{16}$ or —$C(=O)$—$OR^{16}$. In some embodiments, $R^a$ and $R^b$ are taken together with the carbon atom to which they are attached to form a carbonyl (C=O); $R^c$ is $R^g$; $R^g$ is —$(C(R^{17})_2O)_p$—$R^{15}$, —$(CH_2CH_2O)_q$—$R^{15}$, or —$(C(R^{17})_2)_p$—$OR^{15}$; and $R^{15}$ is hydrogen, substituted or unsubstituted alkyl, substituted or unsubstituted heteroalkyl, substituted or unsubstituted $C_2$-$C_{10}$heterocycloalkyl, —$C(=O)R^{16}$, —$C(=O)$—$OR^{16}$, or —$C(=O)N(R^{16})_2$. In some embodiments, $R^a$ and $R^b$ are taken together with the carbon atom to which they are attached to form a carbonyl (C=O); $R^c$ is $R^g$; and $R^g$ is —$(CH_2O)_p$—$R^{15}$, —$(CH_2CH_2O)_q$—$R^{15}$, or —$(CH_2)_p$—$OR^{15}$. In some embodiments, $R^a$ and $R^b$ are taken together with the carbon atom to which they are attached to form a carbonyl (C=O); $R^c$ is $R^g$; and $R^g$ is —$CH_2OR^{15}$, —$CH_2CH_2OR^{15}$, —$(CH_2CH_2O)_2$—$R^{15}$, —$(CH_2CH_2O)_3$—$R^{15}$, —$(CH_2CH_2O)_4$—$R^{15}$, —$(CH_2CH_2O)_5$—$R^{15}$, —$(CH_2)_3$—$OR^{15}$, —$(CH_2)_4$—$OR^{15}$, or —$(CH_2)_5$—$OR^{15}$. In some embodiments, $R^a$ and $R^b$ are taken together with the carbon atom to which they are attached to form a carbonyl (C=O); $R^c$ is $R^g$; and $R^g$ is —$CH_2OR^{15}$ or —$CH_2CH_2OR^{15}$. In some embodiments, $R^a$ and $R^b$ are taken together with the carbon atom to which they are attached to form a carbonyl (C=O); $R^c$ is $R^g$; and $R^g$ is —$CH_2OR^{15}$.

In some embodiments, $R^a$ and $R^b$ are taken together with the carbon atom to which they are attached to form a carbonyl (C=O); $R^c$ is $R^g$; $R^g$ is —$CH_2OR^{15}$; and $R^{15}$ is hydrogen, substituted or unsubstituted alkyl, substituted or unsubstituted heteroalkyl, substituted or unsubstituted $C_2$-$C_{10}$heterocycloalkyl, —$C(=O)R^{16}$, —$C(=O)$—$OR^{16}$, or —$C(=O)N(R^{16})_2$. In some embodiments, $R^a$ and $R^b$ are taken together with the carbon atom to which they are attached to form a carbonyl (C=O); $R^c$ is $R^g$; $R^g$ is —$CH_2OR^{15}$; and $R^{15}$ is substituted or unsubstituted $C_2$-$C_{10}$heterocycloalkyl, —$C(=O)R^{16}$, —$C(=O)$—$OR^{16}$, or —$C(=O)N(R^{16})_2$. In some embodiments, $R^a$ and $R^b$ are taken together with the carbon atom to which they are attached to form a carbonyl (C=O); $R^c$ is $R^g$; $R^g$ is —CH$_2$OR$^{15}$; and R$^{15}$ is —C(=O)R$^{16}$, —C(=O)—OR$^{16}$, or —C(=O)N(R$^{16}$)$_2$.

In some embodiments, $R^a$ and $R^b$ are taken together with the carbon atom to which they are attached to form a carbonyl (C=O); $R^c$ is $R^g$; $R^g$ is —CH$_2$OR$^{15}$; R$^{15}$ is —C(=O)R$^{16}$; and each R$^{16}$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), or -alkyl-(substituted or unsubstituted $C_2$-$C_6$ heterocycloalkyl).

In some embodiments,

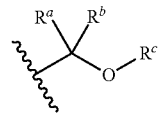

is

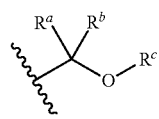

In some embodiments,

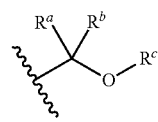

is

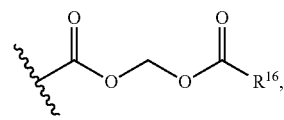

In some embodiments,

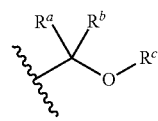

is

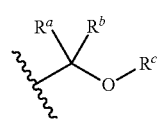

In some embodiments,

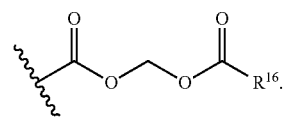

is

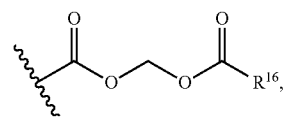

and R$^{16}$ is hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), or -alkyl-(substituted or unsubstituted $C_2$-$C_6$ heterocycloalkyl).

In some embodiments,

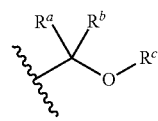

is

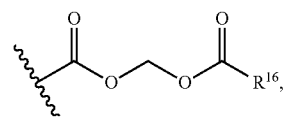

and R$^{16}$ is substituted or unsubstituted $C_2$-$C_6$ heterocycloalkyl, substituted or unsubstituted heteroaryl, -alkyl-(substituted or unsubstituted heteroaryl), or -alkyl-(substituted or unsubstituted $C_2$-$C_6$ heterocycloalkyl). In some embodiments,

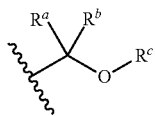

is

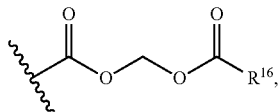

and $R^{16}$ is substituted or unsubstituted $C_2$-$C_6$ heterocycloalkyl, substituted or unsubstituted heteroaryl, —CH$_2$-(substituted or unsubstituted heterocycloalkyl), —(CH$_2$)$_2$-(substituted or unsubstituted heterocycloalkyl), —(CH$_2$)$_3$-(substituted or unsubstituted heterocycloalkyl), —CH$_2$-(substituted or unsubstituted heteroaryl), —(CH$_2$)$_2$-(substituted or unsubstituted heteroaryl), or —(CH$_2$)$_3$-(substituted or unsubstituted heteroaryl). In some embodiments,

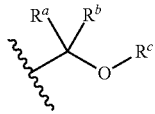

is

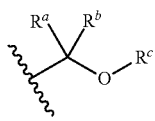

and $R^{16}$ is substituted $C_2$-$C_6$ heterocycloalkyl or substituted heteroaryl. In some embodiments

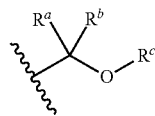

is

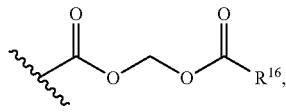

and $R^{16}$ is unsubstituted $C_2$-$C_6$ heterocycloalkyl or unsubstituted heteroaryl. In some embodiments,

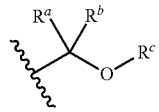

is

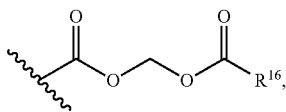

and $R^{16}$ is substituted $C_2$-$C_6$ heterocycloalkyl. In some embodiments,

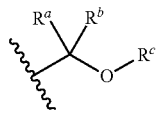

is

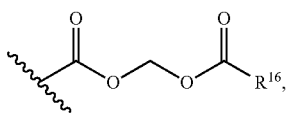

and $R^{16}$ is substituted heteroaryl. In some embodiments,

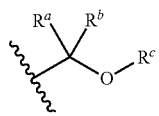

is

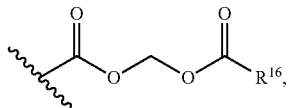

and R[16] is unsubstituted $C_2$-$C_6$ heterocycloalkyl. In some embodiments,

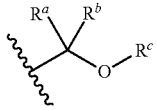

is

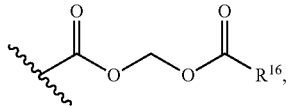

and R[16] is unsubstituted heteroaryl.
In some embodiments,

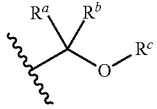

is

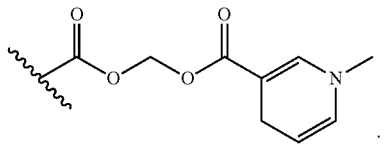 [SMILES: *C(=O)OCOC(=O)C1=CN(C)C=CC1]

In some embodiments, R[1] is

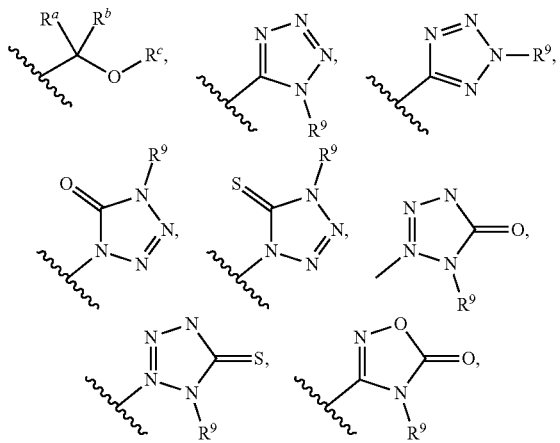

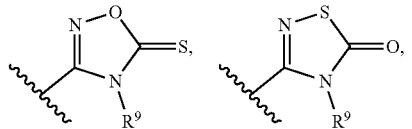

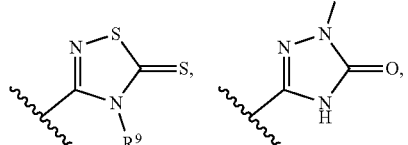

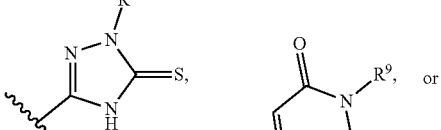

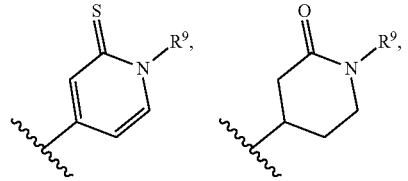

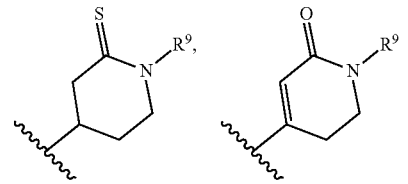

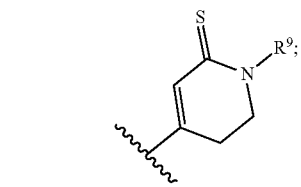

$R^a$ is hydrogen, —CH₃, —CH₂CH₃, —CD₃, —CH₂CD₃, —CF₃, or —CH₂CF₃; $R^b$ is hydrogen, —CH₃, —CH₂CH₃, —CD₃, —CH₂CD₃, —CF₃, or —CH₂CF₃; or $R^a$ and $R^b$ are taken together with the carbon atom to which they are attached to form a ring C that is a substituted or unsubstituted oxetane, substituted or unsubstituted thietane 1,1-dioxide, or substituted or unsubstituted azetidine; and $R^c$ is hydrogen, $C_1$-$C_6$alkyl, $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), -alkyl-(substituted or unsubstituted $C_2$-$C_6$heterocycloalkyl), —C(=O)R[16], —C(=O)—OR[16], —C(=O)N(R[16])₂, —(CH₂O)$_p$—R[15], or —(CH(CH₃)O)$_p$—R[15]; p is 1, 2, 3, 4, or 5; and R[15] is hydrogen, substituted or unsubstituted alkyl, substituted or unsubstituted heteroalkyl, substituted or unsubstituted $C_2$-$C_{10}$heterocycloalkyl, —C(=O)R[16], —C(=O)—OR[16], or —C(=O)N(R[16])₂.

In some embodiments, $R^1$ is

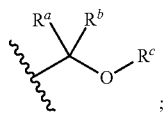

$R^a$ and $R^b$ are taken together with the carbon atom to which they are attached to form a ring C that is a substituted or unsubstituted oxetane, substituted or unsubstituted thietane 1,1-dioxide, or substituted or unsubstituted azetidine. In some embodiments, $R^1$ is

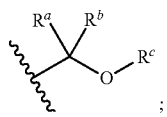

$R^a$ and $R^b$ are taken together with the carbon atom to which they are attached to form a ring C that is a substituted or unsubstituted oxetane, substituted or unsubstituted thietane 1,1-dioxide, or substituted or unsubstituted azetidine; and $R^c$ is hydrogen, $C_1$-$C_6$alkyl, $C_1$-$C_6$ deuteroalkyl, or $C_1$-$C_6$ fluoroalkyl. In some embodiments, $R^1$ is

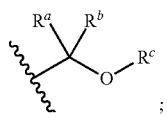

$R^a$ and $R^b$ are taken together with the carbon atom to which they are attached to form a ring C that is a substituted or unsubstituted oxetane, substituted or unsubstituted thietane 1,1-dioxide, or substituted or unsubstituted azetidine; and $R^c$ is hydrogen, —$CH_3$, —$CH_2CH_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^1$ is

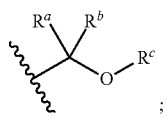

$R^a$ and $R^b$ are taken together with the carbon atom to which they are attached to form a ring C that is a substituted or unsubstituted oxetane, substituted or unsubstituted thietane 1,1-dioxide, or substituted or unsubstituted azetidine; and $R^c$ is hydrogen, —$CH_3$, or —$CH_2CH_3$. In some embodiments, $R^1$ is

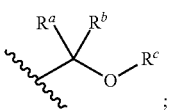

$R^a$ and $R^b$ are taken together with the carbon atom to which they are attached to form a ring C that is a substituted or unsubstituted oxetane, substituted or unsubstituted thietane 1,1-dioxide, or substituted or unsubstituted azetidine; and $R^c$ is hydrogen.

In some embodiments, $R^1$ is

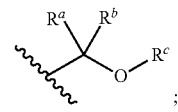

$R^a$ and $R^b$ are taken together with the carbon atom to which they are attached to form a ring C that is a substituted or unsubstituted oxetane. In some embodiments, $R^1$ is

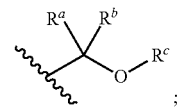

$R^a$ and $R^b$ are taken together with the carbon atom to which they are attached to form a ring C that is a substituted or unsubstituted oxetane; and $R^c$ is hydrogen, —$CH_3$, —$CH_2CH_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^1$ is

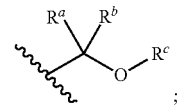

$R^a$ and $R^b$ are taken together with the carbon atom to which they are attached to form a ring C that is a substituted or unsubstituted oxetane; and $R^c$ is hydrogen.

In some embodiments, $R^1$ is

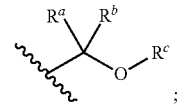

$R^a$ and $R^b$ are taken together with the carbon atom to which they are attached to form a ring C that is a substituted or unsubstituted thietane 1,1-dioxide. In some embodiments, $R^1$ is

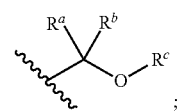

$R^a$ and $R^b$ are taken together with the carbon atom to which they are attached to form a ring C that is a substituted or unsubstituted thietane 1,1-dioxide; and $R^c$ is hydrogen, —$CH_3$, —$CH_2CH_3$, —$CH_2D$, —$CHD_2$, —$CD_3$, —$CH_2CH_2D$, —$CH_2CHD_2$, —$CH_2CD_3$, —$CD_2CD_3$, —CH$_2$F, —CHF$_2$, —CF$_3$, —CH$_2$CH$_2$F, —CH$_2$CHF$_2$, —CH$_2$CF$_3$, or —CF$_2$CF$_3$. In some embodiments, R$^1$ is

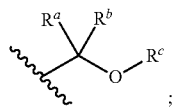

R$^a$ and R$^b$ are taken together with the carbon atom to which they are attached to form a ring C that is a substituted or unsubstituted thietane 1,1-dioxide; and R$^c$ is hydrogen.

In some embodiments, R$^1$ is

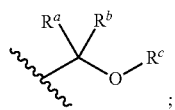

R$^a$ and R$^b$ are taken together with the carbon atom to which they are attached to form a ring C that is a substituted or unsubstituted azetidine. In some embodiments, R$^1$ is

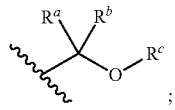

R$^a$ and R$^b$ are taken together with the carbon atom to which they are attached to form a ring C that is a substituted or unsubstituted azetidine; and R$^c$ is hydrogen, —CH$_3$, —CH$_2$CH$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, or —CF$_2$CF$_3$. In some embodiments, R$^1$ is

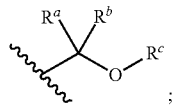

R$^a$ and R$^b$ are taken together with the carbon atom to which they are attached to form a ring C that is a substituted or unsubstituted azetidine; and R$^c$ is hydrogen.

In some embodiments, R$^1$ is

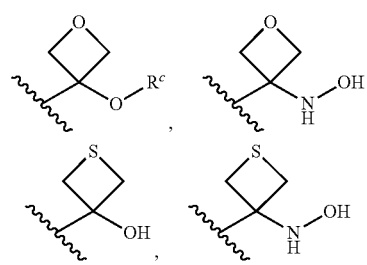

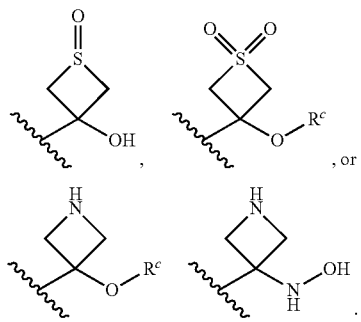

In some embodiments, R$^1$ is

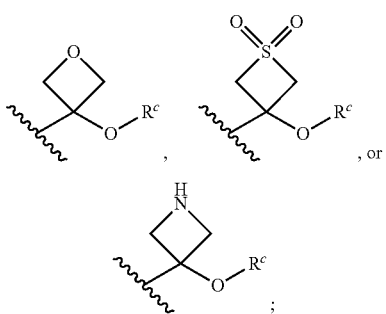

and R$^c$ is hydrogen, —CH$_3$, —CH$_2$CH$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, or —CF$_2$CF$_3$. In some embodiments, R$^1$ is

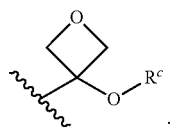

In some embodiments, R$^1$ is

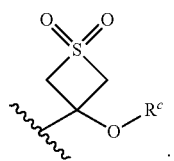

In some embodiments, R$^1$ is

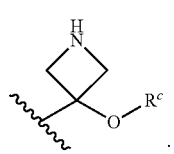

In some embodiments, R$^1$ is

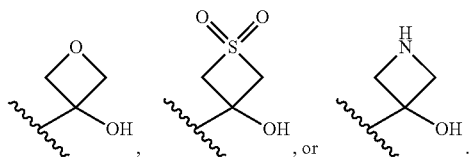 [SMILES: *C1(O)COC1 ; *C1(O)CS(=O)(=O)C1 ; *C1(O)CNC1]

In some embodiments, R$^1$ is

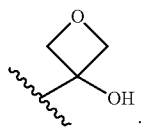 [SMILES: *C1(O)COC1]

In some embodiments, R$^1$ is

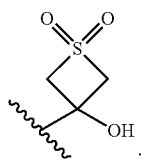 [SMILES: *C1(O)CS(=O)(=O)C1]

In some embodiments, R$^1$ is

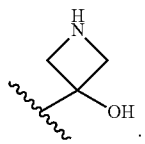 [SMILES: *C1(O)CNC1]

In some embodiments, R$^1$ is —C(O)NR$^d$R$^e$. In some embodiments, R$^1$ is —C(O)NR$^d$R$^e$, and R$^e$ is hydrogen or —CH$_3$. In some embodiments, R$^1$ is —C(O)NR$^d$R$^e$, and R$^e$ is hydrogen. In some embodiments, R$^1$ is —C(O)NR$^d$R$^e$, and R$^e$ is —CH$_3$. In some embodiments, R$^1$ is —C(O)NHR$^d$. In some embodiments R$^d$ is —CN, C$_1$-C$_6$ alkyl, C$_1$-C$_6$ fluoroalkyl, —OH, —OR$^{1d}$, or —SO$_2$R$^{1d}$. In some embodiments R$^d$ is —CN. In some embodiments, R$^1$ is —C(O)NHCN. In some embodiments, R$^d$ is —OH or —OR$^{1d}$. In some embodiments, R$^1$ is —C(O)NHOH or —C(O)NHOR$^{1d}$. In some embodiments R$^{1d}$ is —CH$_3$. In some embodiments, R$^1$ is —C(O)NHOH or —C(O)NHOCH$_3$. In some embodiments, R$^1$ is —C(O)NH(C$_1$-C$_6$ alkyl). In some embodiments, R$^1$ is —C(O)NHCH$_3$, —C(O)NHCH$_2$CH$_3$, —C(O)NHCH(CH$_3$)$_2$, —C(O)NC(CH$_3$)$_3$, or —C(O)NHCH$_2$CH$_2$CH$_3$. In some embodiments, R$^1$ is —C(O)NHCH$_3$. In some embodiments, R$^1$ is —C(O)N(CH$_3$)$_2$. In some embodiments, R$^1$ is —C(O)NH(C$_1$-C$_6$ haloalkyl). In some embodiments, R$^1$ is —C(O)NHCH$_2$CF$_3$.

In some embodiments, R$^1$ is —C(O)NHSO$_2$R$^{1d}$. In some embodiments, R$^{1d}$ is substituted or unsubstituted C$_1$-C$_6$ alkyl, substituted or unsubstituted C$_3$-C$_6$ cycloalkyl, substituted or unsubstituted 3- to 6-membered heterocycloalkyl, substituted or unsubstituted phenyl, or substituted or unsubstituted 5- to 6-membered heteroaryl; wherein if R$^{1d}$ is substituted then it is substituted with one or more R$^{14}$. In some embodiments, R$^{1d}$ is substituted or unsubstituted C$_1$-C$_6$ alkyl. In some embodiments, R$^{1d}$ is substituted or unsubstituted methyl, wherein if R$^{1d}$ is substituted, then it is substituted with one, two, or three R$^{14}$. In some embodiments, R$^{14}$ is fluorine. In some embodiments, R$^{14}$ is —C$_1$-C$_6$ alkyl. In some embodiments, R$^{14}$ is —OCH$_3$. In some embodiments, R$^{1d}$ is —CH$_3$, —CH$_2$CH$_3$, —CH$_2$CF$_3$, —CH$_2$OCH$_3$, —CH$_2$F, —CH(CH$_3$)$_2$, —CHF$_2$, —C(CH$_3$)$_3$, or —CF$_3$. In some embodiments, R$^1$ is —C(O)NHSO$_2$CH$_3$, —C(O)NHSO$_2$CH$_2$CH$_3$, —C(O)NHSO$_2$CH$_2$CF$_3$, —C(O)NHSO$_2$CH$_2$OCH$_3$, —C(O)NHSO$_2$CH$_2$F, —C(O)NHSO$_2$CH(CH$_3$)$_2$, —C(O)NHSO$_2$CHF$_2$, —C(O)NHSO$_2$C(CH$_3$)$_3$, or —C(O)NHSO$_2$CF$_3$. In some embodiments, R$^1$ is —C(O)NHSO$_2$(C$_1$-C$_6$ alkyl). In some embodiments, R$^1$ is —C(O)NHSO$_2$(substituted or unsubstituted methyl).

In some embodiments, R$^{1d}$ is substituted or unsubstituted C$_3$-C$_6$ cycloalkyl. In some embodiments, R$^{1d}$ is substituted or unsubstituted cyclopropyl, substituted or unsubstituted cyclobutyl, substituted or unsubstituted cyclopentyl, or substituted or unsubstituted cyclohexyl. In some embodiments, R$^{1d}$ is substituted or unsubstituted cyclopropyl. In some embodiments, R$^1$ is —C(O)NHSO$_2$(C$_3$-C$_6$ cycloalkyl). In some embodiments, R$^1$ is —C(O)NHSO$_2$(3- to 6-membered heterocycloalkyl). In some embodiments, R$^{1d}$ is oxetanyl, azetidinyl, tetrahydrofuranyl, or pyrrolidinyl. In some embodiments, R$^1$ is —C(O)NHSO$_2$(oxetanyl). In some embodiments, R$^{1d}$ is substituted or unsubstituted phenyl. In some embodiments, R$^1$ is —C(O)NHSO$_2$(phenyl). In some embodiments, R$^{1d}$ is substituted or unsubstituted 5- or 6-membered heteroaryl. In some embodiments, R$^{1d}$ is substituted or unsubstituted piperidinyl, or substituted or unsubstituted pyrimidinyl. In some embodiments, R$^1$ is —C(O)NHSO$_2$(phenyl).

In some embodiments, R$^2$ is hydrogen, C$_1$-C$_6$ alkyl, C$_1$-C$_6$ deuteroalkyl, or C$_1$-C$_6$ fluoroalkyl. In some embodiments, R$^2$ is hydrogen, —CH$_3$, —CH$_2$CH$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, or —CF$_2$CF$_3$. In some embodiments, R$^2$ is hydrogen, —CH$_3$, —CH$_2$CH$_3$, —CD$_3$, —CH$_2$CD$_3$, —CF$_3$, or —CH$_2$CF$_3$. In some embodiments, R$^2$ is hydrogen, —CH$_3$, —CD$_3$, or —CF$_3$. In some embodiments, R$^2$ is —CH$_3$, —CD$_3$, or —CF$_3$. In some embodiments, R$^2$ is —CH$_3$. In some embodiments, R$^2$ is —CD$_3$. In some embodiments, R$^2$ is —CF$_3$. In some embodiments, R$^2$ is hydrogen.

In some embodiments, R$^3$ is hydrogen, C$_1$-C$_6$ alkyl, C$_1$-C$_6$ deuteroalkyl, or C$_1$-C$_6$ fluoroalkyl. In some embodiments, R$^3$ is hydrogen, —CH$_3$, —CH$_2$CH$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, or —CF$_2$CF$_3$. In some embodiments, R$^3$ is hydrogen, —CH$_3$, —CH$_2$CH$_3$, —CD$_3$, —CH$_2$CD$_3$, —CF$_3$, or —CH$_2$CF$_3$. In some embodiments, R$^3$ is hydrogen, —CH$_3$, —CD$_3$, or —CF$_3$. In some embodiments, R$^3$ is —CH$_3$, —CD$_3$, or —CF$_3$. In some embodiments, R$^3$ is —CH$_3$. In some embodiments, R$^3$ is —CD$_3$. In some embodiments, R$^3$ is —CF$_3$. In some embodiments, R$^3$ is hydrogen.

In some embodiments, R$^2$ is hydrogen, —CH$_3$, —CH$_2$CH$_3$, —CD$_3$, —CH$_2$CD$_3$, —CF$_3$, or —CH$_2$CF$_3$; R$^3$ is hydrogen, —CH$_3$, —CH$_2$CH$_3$, —CD$_3$, —CH$_2$CD$_3$, —CF$_3$, or —CH$_2$CF$_3$; or R$^2$ and R$^3$ are taken together with the carbon atom to which they are attached to form a carbonyl (C=O); or R$^2$ and R$^3$ are taken together with the carbon atom to which they are attached to form a ring B that is a substituted or unsubstituted oxetane, substituted or unsubstituted thietane 1,1-dioxide, or substituted or unsubstituted azetidine.

In some embodiments, $R^2$ is hydrogen, —$CH_3$, —$CD_3$, or —$CF_3$; $R^3$ is hydrogen, —$CH_3$, —$CD_3$, or —$CF_3$; or $R^2$ and $R^3$ are taken together with the carbon atom to which they are attached to form a carbonyl (C=O); or $R^2$ and $R^3$ are taken together with the carbon atom to which they are attached to form a ring B that is a substituted or unsubstituted oxetane, substituted or unsubstituted thietane 1,1-dioxide, or substituted or unsubstituted azetidine.

In some embodiments, the compound of Formula (I) has the following structure of Formula (V) or (VI):

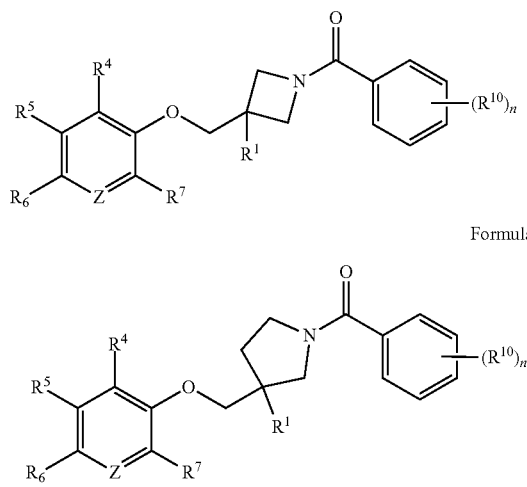

Formula (V)

or

Formula (VI)

or a pharmaceutically acceptable salt, or solvate thereof.

In some embodiments, the compound of Formula (I') has the following structure of Formula (V') or (VI'):

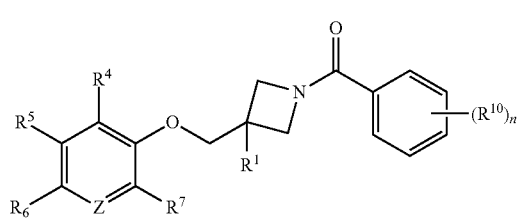

Formula (V')

or

Formula (VI")

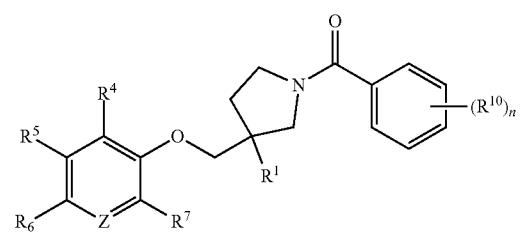

or a pharmaceutically acceptable salt, or solvate thereof.

In some embodiments, the compound of Formula (I) has the following structure of Formula (V):

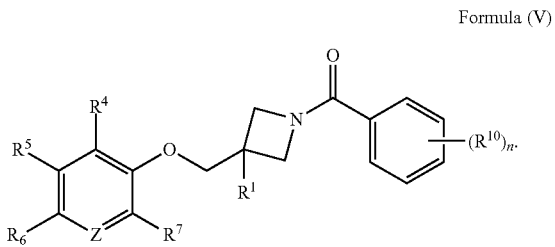

Formula (V)

or a pharmaceutically acceptable salt, or solvate thereof.

In some embodiments, the compound of Formula (I) has the following structure of Formula (VI):

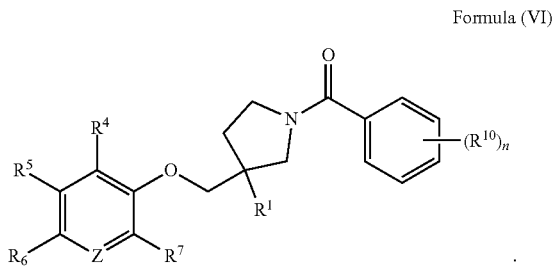

Formula (VI)

or a pharmaceutically acceptable salt, or solvate thereof.

In some embodiments, the compound of Formula (I) has the following structure of Formula (VI-A):

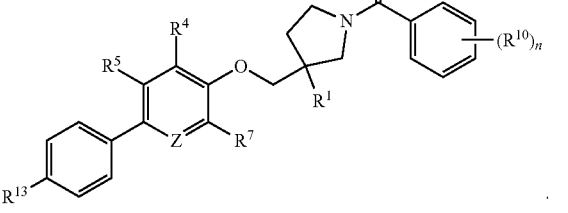

Formula (VI-A)

or a pharmaceutically acceptable salt, or solvate thereof.

In some embodiments, the compound of Formula (I') has the following structure of Formula (VI-A'):

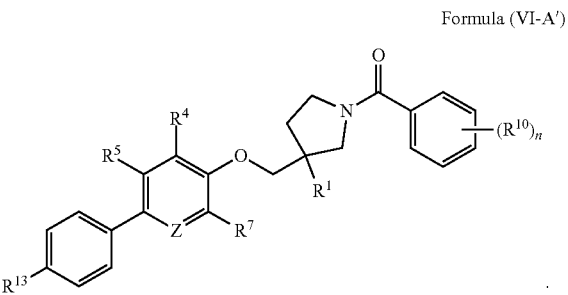

Formula (VI-A')

or a pharmaceutically acceptable salt, or solvate thereof.

In some embodiments, the compound of Formula (I) has the following structure of Formula (VI-A″):

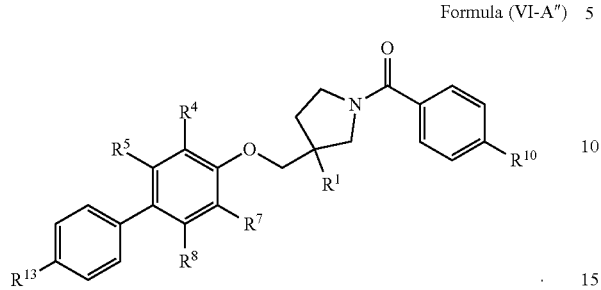

Formula (VI-A″)

or a pharmaceutically acceptable salt, or solvate thereof.

In some embodiments, the compound of Formula (I) has the following structure of Formula (VI-A‴):

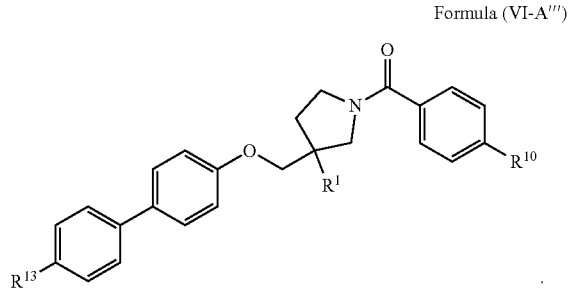

Formula (VI-A‴)

or a pharmaceutically acceptable salt, or solvate thereof.

In some embodiments, $R^1$ is —C(O)NHSO$_2$R$^{1d}$. In some embodiments, $R^{1d}$ is substituted or unsubstituted C$_1$-C$_6$ alkyl; wherein if $R^{1d}$ is substituted then it is substituted with one or more $R^{14}$. In some embodiments, $R^{1d}$ is substituted or unsubstituted methyl, wherein if $R^{1d}$ is substituted, then it is substituted with one, two, or three $R^{14}$. In some embodiments, $R^{14}$ is fluorine. In some embodiments, $R^{14}$ is —C$_1$-C$_6$ alkyl. In some embodiments, $R^{14}$ is —OCH$_3$. In some embodiments, $R^{1d}$ is —CH$_3$, —CH$_2$CH$_3$, —CH$_2$CF$_3$, —CH$_2$OCH$_3$, —CH$_2$F, —CH(CH$_3$)$_2$, —CHF$_2$, —C(CH$_3$)$_3$, or —CF$_3$. In some embodiments, $R^1$ is —C(O)NHSO$_2$CH$_3$, —C(O)NHSO$_2$CH$_2$CH$_3$, —C(O)NHSO$_2$CH$_2$CF$_3$, —C(O)NHSO$_2$CH$_2$OCH$_3$, —C(O)NHSO$_2$CH$_2$F, —C(O)NHSO$_2$CH(CH$_3$)$_2$, —C(O)NHSO$_2$CHF$_2$, —C(O)NHSO$_2$C(CH$_3$)$_3$, or —C(O)NHSO$_2$CF$_3$. In some embodiments, $R^1$ is —C(O)NHSO$_2$(C$_1$-C$_6$ alkyl).

In some embodiments, the compound of Formula (I) has the following structure of Formula (VI-B) or (VI-C):

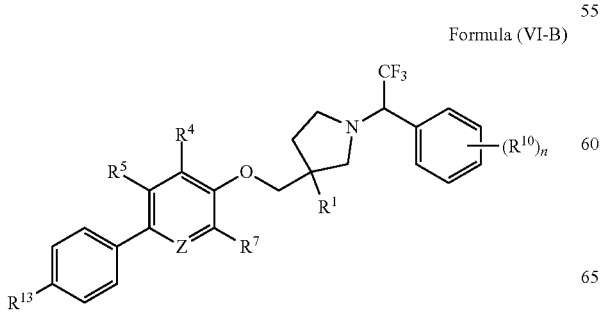

Formula (VI-B)

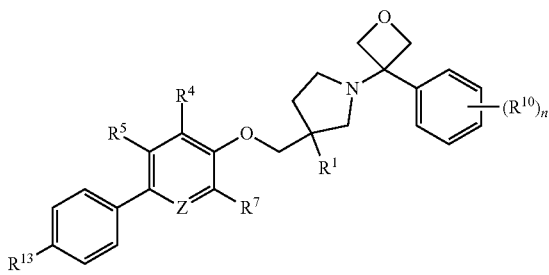

Formula (VI-C)

or a pharmaceutically acceptable salt, or solvate thereof.

In some embodiments, the compound of Formula (I) has the following structure of Formula (VII):

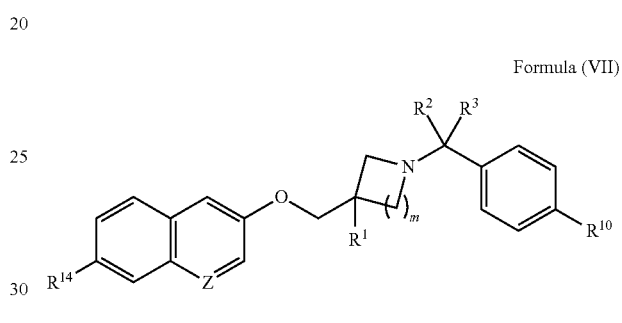

Formula (VII)

or a pharmaceutically acceptable salt, or solvate thereof.

In some embodiments, the compound of Formula (I) has the following structure of Formula (VIII) or Formula (IX):

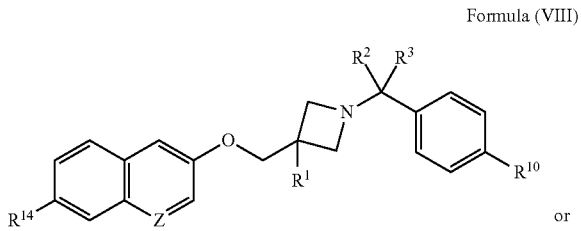

Formula (VIII)

or

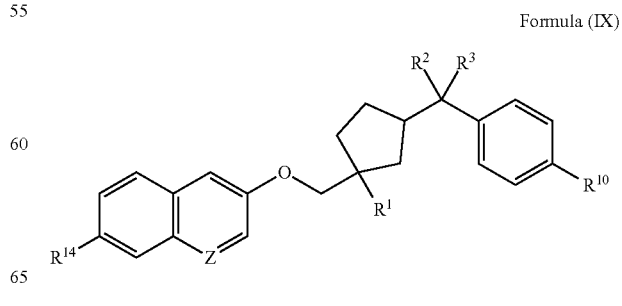

Formula (IX)

or a pharmaceutically acceptable salt, or solvate thereof.

In another aspect, described herein is a compound of Formula (X), or a pharmaceutically acceptable salt, or solvate thereof:

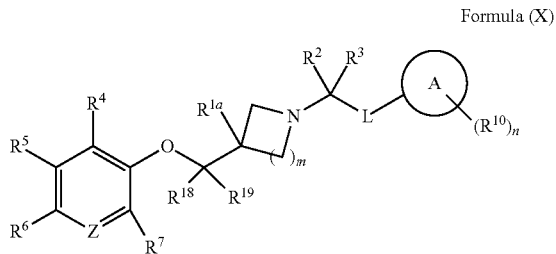

Formula (X)

wherein:

$R^{1a}$ is —CO$_2$H, —CO$_2$—R$^{1b}$, —C(O)N(R$^{1c}$)$_2$, or —CN;

$R^{1b}$ is C$_1$-C$_6$ alkyl, C$_1$-C$_6$ deuteroalkyl, C$_1$-C$_6$ fluoroalkyl, substituted or unsubstituted C$_1$-C$_6$ heteroalkyl, substituted or unsubstituted C$_3$-C$_6$ cycloalkyl, substituted or unsubstituted C$_2$-C$_6$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted C$_3$-C$_6$cycloalkyl), -alkyl-(substituted or unsubstituted C$_2$-C$_6$heterocycloalkyl), —C(=O)R$^{16}$, —C(=O)—OR$^{16}$, —C(=O)N(R$^{16}$)$_2$, —(C(R$^{17}$)$_2$O)$_p$—R$^{15}$, —(CH$_2$CH$_2$O)$_q$—R$^{15}$, or —(C(R$^{17}$)$_2$)$_p$—OR$^{15}$;

p is 1, 2, 3, 4, or 5;

q is 1, 2, 3, 4, or 5;

each R$^{17}$ is independently hydrogen or C$_1$-C$_6$ alkyl;

R$^{15}$ is hydrogen, substituted or unsubstituted alkyl, substituted or unsubstituted heteroalkyl, substituted or unsubstituted C$_2$-C$_{10}$heterocycloalkyl, —C(=O)R$^{16}$, —C(=O)—OR$^{16}$, or —C(=O)N(R$^{16}$)$_2$;

each R$^{1c}$ is independently hydrogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, or substituted or unsubstituted C$_2$-C$_6$ heterocycloalkyl;

or both R$^{1c}$ are taken together with the N atom to which they are attached to form a substituted or unsubstituted C$_2$-C$_6$ heterocycloalkyl;

R$^2$ is hydrogen, C$_1$-C$_6$ alkyl, C$_1$-C$_6$ deuteroalkyl, or C$_1$-C$_6$ fluoroalkyl;

R$^3$ is hydrogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, or substituted or unsubstituted C$_2$-C$_6$ heterocycloalkyl;

or R$^2$ and R$^3$ are taken together with the carbon atom to which they are attached to form a thiocarbonyl (C=S);

or R$^2$ and R$^3$ are taken together with the carbon atom to which they are attached to form a ring B that is a substituted or unsubstituted C$_3$-C$_6$ cycloalkyl, or substituted or unsubstituted C$_2$-C$_6$ heterocycloalkyl, wherein if the ring B is substituted then it is substituted with one or more R$^{12}$;

Z is N or CR$^8$;

L is absent or —NH—;

R$^4$, R$^5$, R$^7$, and R$^8$ are each independently hydrogen, halogen, —CN, C$_1$-C$_6$ alkyl, C$_1$-C$_6$ deuteroalkyl, C$_1$-C$_6$ fluoroalkyl, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$;

R$^6$ is hydrogen, halogen, —CN, C$_1$-C$_6$ alkyl, C$_1$-C$_6$ deuteroalkyl, C$_1$-C$_6$ fluoroalkyl, —OR$^{16}$, —C(=O)R$^{16}$, —CO$_2$R$^{16}$, —C(=O)N(R$^{16}$)$_2$, —N(R$^{16}$)$_2$, —NR$^{16}$C(=O)R$^{16}$, substituted or unsubstituted C$_3$-C$_6$ cycloalkyl, substituted or unsubstituted C$_2$-C$_6$heterocycloalkyl, substituted or unsubstituted phenyl, or substituted or unsubstituted heteroaryl; wherein if R$^6$ is substituted then it is substituted with one or more R$^{13}$;

or R$^5$ and R$^6$ are taken together, with the intervening atoms to which they are attached, to form a fused ring D that is a substituted or unsubstituted 5- or 6-membered carbocycle or substituted or unsubstituted 5- or 6-membered heterocycle, wherein if ring D is substituted then it is substituted with one or more R$^{14}$;

ring A is a substituted or unsubstituted phenyl, or substituted or unsubstituted heteroaryl;

each R$^{10}$, R$^{12}$, R$^{13}$, and R$^{14}$ is independently hydrogen, deuterium, halogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, substituted or unsubstituted C$_2$-C$_6$ heterocycloalkyl, —CN, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$;

each R$^{16}$ is independently hydrogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, substituted or unsubstituted C$_2$-C$_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted C$_3$-C$_6$ cycloalkyl), -alkyl-(substituted or unsubstituted C$_2$-C$_6$ heterocycloalkyl);

or both R$^{16}$ are taken together with the N atom to which they are attached to form a substituted or unsubstituted C$_2$-C$_6$ heterocycloalkyl;

R$^{18}$ and R$^{19}$ are each independently hydrogen, deuterium, C$_1$-C$_6$ alkyl, C$_1$-C$_6$ deuteroalkyl, or C$_1$-C$_6$ fluoroalkyl;

or R$^{18}$ and R$^{19}$ are taken together with the carbon atom to which they are attached to form a ring E that is a C$_3$-C$_6$cycloalky, or C$_2$-C$_6$ heterocycloalkyl;

m is 1 or 2; and n is 0, 1, 2, 3, or 4.

In some embodiments, the compound of Formula (X) has the following structure of Formula (XI):

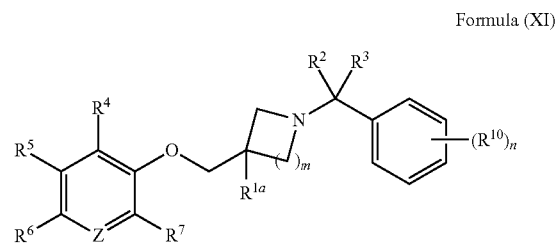

Formula (XI)

or a pharmaceutically acceptable salt, or solvate thereof.

In some embodiments, m is 1. In some embodiments, the compound of Formula (X) has the following structure of Formula (XII):

Formula (XII)

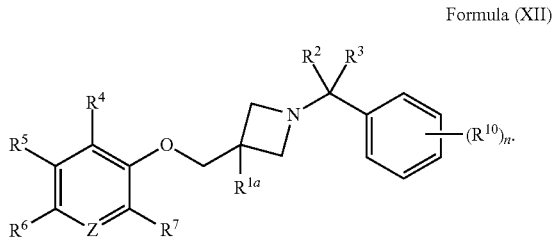

or a pharmaceutically acceptable salt, or solvate thereof.

In some embodiments, m is 2. In some embodiments, the compound of Formula (X) has the following structure of Formula (XIII):

Formula (XIII)

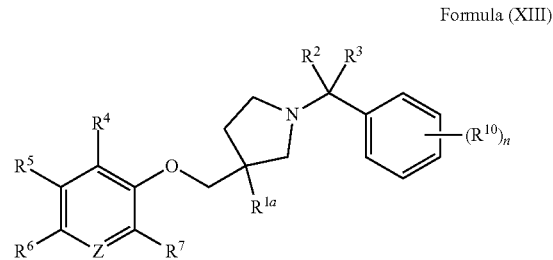

or a pharmaceutically acceptable salt, or solvate thereof.

In some embodiments, $R^{1a}$ is —$CO_2H$, —$CO_2$—$R^{1b}$, —C(O)N($R^{1c}$)$_2$, or —CN. In some embodiments, $R^{1a}$ is —$CO_2H$, —$CO_2$—$R^{1b}$, or —CN. In some embodiments, $R^{1a}$ is —$CO_2H$ or —CN. In some embodiments, $R^{1a}$ is —$CO_2H$. In some embodiments, $R^{1a}$ is —CN.

In some embodiments, $R^{1a}$ is —$CO_2H$ or —$CO_2$—$R^{1b}$. In some embodiments, $R^{1a}$ is —$CO_2$—$R^{1b}$. In some embodiments, $R^{1a}$ is —$CO_2$—$R^{1b}$; and $R^{1b}$ is $C_1$-$C_6$ alkyl, $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), -alkyl-(substituted or unsubstituted $C_2$-$C_6$heterocycloalkyl), —C(=O)$R^{16}$, —C(=O)—$OR^{16}$, —C(=O)N($R^{16}$)$_2$, —(C($R^{17}$)$_2$O)$_p$—$R^{15}$, —($CH_2CH_2$O)$_q$—$R^{15}$, or —(C($R^7$)$_2$)$_p$—$OR^{15}$.

In some embodiments, $R^{1a}$ is —$CO_2H$, —$CO_2$—$R^{1b}$, —C(=O)N($R^{1c}$)$_2$, —C(=O)$NH_2$, —C(=O)$NHCH_3$, —C(=O)N($CH_3$)$_2$, or —CN; $R^{1b}$ is $C_1$-$C_6$ alkyl, $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$ cycloalkyl), -alkyl-(substituted or unsubstituted $C_2$-$C_6$ heterocycloalkyl), —C(=O)$R^{16}$, —C(=O)—$OR^{16}$, —C(=O)N($R^{16}$)$_2$, —($CH_2$O)$_p$—$R^{15}$, or —(CH($CH_3$)O)$_p$—$R^{15}$; p is 1, 2, 3, 4, or 5; and $R^{15}$ is hydrogen, substituted or unsubstituted alkyl, substituted or unsubstituted heteroalkyl, substituted or unsubstituted $C_2$-$C_{10}$ heterocycloalkyl, —C(=O)$R^{16}$, —C(=O)—$OR^{16}$, or —C(=O)N($R^{16}$)$_2$.

In some embodiments, $R^{1b}$ is $C_1$-$C_6$alkyl, $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), -alkyl-(substituted or unsubstituted $C_2$-$C_6$heterocycloalkyl), —C(=O)$R^{16}$, —C(=O)—$OR^{16}$, —C(=O)N($R^{16}$)$_2$, —($CH_2$O)$_p$—$R^{15}$, or —(CH($CH_3$)O)$_p$—$R^{15}$. In some embodiments, $R^{1b}$ is —$CH_3$, —$CH_2CH_3$, —($CH_2$)$_2CH_3$, —($CH_2$)$_3CH_3$, —CH($CH_3$)$_2$, or —C($CH_3$)$_3$. In some embodiments, $R^{1b}$ is —$CH_3$. In some embodiments, $R^{1b}$ is —$CH_2CH_3$. In some embodiments, $R^{1b}$ is —($CH_2$)$_2CH_3$, —($CH_2$)$_3CH_3$, —CH($CH_3$)$_2$, or —C($CH_3$)$_3$.

In some embodiments, $R^{1b}$ is $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$ cycloalkyl), -alkyl-(substituted or unsubstituted $C_2$-$C_6$ heterocycloalkyl), —C(=O)$R^{16}$, —C(=O)—$OR^{16}$, —C(=O)N($R^{16}$)$_2$, —(C($R^{17}$)$_2$O)$_p$—$R^{15}$, —($CH_2CH_2$O)$_q$—$R^{15}$, or —(C($R^{17}$)$_2$)$_p$—$OR^{15}$.

In some embodiments, $R^{1b}$ is $C_1$-$C_6$ deuteroalkyl, $C_1$-$C_6$ fluoroalkyl, or substituted or unsubstituted $C_1$-$C_6$ heteroalkyl. In some embodiments, $R^{1b}$ is —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^{1b}$ is —$CD_3$, —$CD_2CD_3$, —$CF_3$, or —$CF_2CF_3$.

In some embodiments, $R^{1b}$ is -alkyl-(substituted or unsubstituted phenyl), -alkyl-(substituted or unsubstituted heteroaryl), -alkyl-(substituted or unsubstituted $C_3$-$C_6$ cycloalkyl), -alkyl-(substituted or unsubstituted $C_2$-$C_6$ heterocycloalkyl).

In some embodiments, $R^{1b}$ is —C(=O)$R^{16}$, —C(=O)—$OR^{16}$, or —C(=O)N($R^{16}$)$_2$. In some embodiments, $R^{1b}$ is —C(=O)$R^{16}$ or —C(=O)—$OR^{16}$. In some embodiments, $R^{1b}$ is —($CH_2$O)$_p$—$R^{15}$ or —(CH($CH_3$)O)$_p$—$OR^{15}$; and $R^{15}$ is hydrogen, substituted or unsubstituted alkyl, substituted or unsubstituted heteroalkyl, substituted or unsubstituted $C_2$-$C_{10}$heterocycloalkyl, —C(=O)$R^{16}$, —C(=O)—$OR^{16}$, or —C(=O)N($R^{16}$)$_2$. In some embodiments, $R^{1b}$ is —$CH_2OR^{15}$, —CH($CH_3$)$OR^{15}$, —(CH($CH_3$)O)$_2$—$R^{15}$, —(CH($CH_3$)O)$_3$—$R^{15}$, —(CH($CH_3$)O)$_4$—$R^{15}$, or —(CH($CH_3$)O)$_5$—$R^{15}$. In some embodiments, $R^{1b}$ is —$CH_2OR^1$.

In some embodiments, $R^{1b}$ is —$CH_2OR^{15}$; and $R^{15}$ is hydrogen, substituted or unsubstituted alkyl, substituted or unsubstituted heteroalkyl, substituted or unsubstituted $C_2$-$C_{10}$heterocycloalkyl, —C(=O)$R^{16}$, —C(=O)—$OR^{16}$, or —C(=O)N($R^{16}$)$_2$. In some embodiments, $R^{1b}$ is —$CH_2OR^{15}$; and $R^{15}$ is substituted or unsubstituted $C_2$-$C_{10}$heterocycloalkyl, —C(=O)$R^{16}$, —C(=O)—$OR^{16}$, or —C(=O)N($R^{16}$)$_2$. In some embodiments, $R^{1b}$ is —$CH_2OR^{15}$; and $R^{15}$ is —C(=O)$R^{16}$, —C(=O)—$OR^{16}$, or —C(=O)N($R^{16}$)$_2$.

In some embodiments, $R^{1b}$ is —$CH_2OR^{15}$; $R^{15}$ is —C(=O)$R^{16}$; and each $R^{16}$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), or -alkyl-(substituted or unsubstituted $C_2$-$C_6$ heterocycloalkyl).

In some embodiments, $R^{1b}$ is —$CH_2OR^{15}$. In some embodiments, —$CO_2$—$R^{1b}$ is

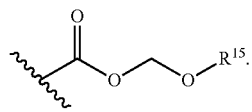

In some embodiments, $R^{15}$ is —$C(=O)R^{16}$. In some embodiments, —$CO_2$—$R^{1b}$ is

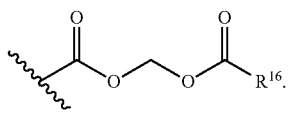

In some embodiments, —$CO_2$—$R^{1b}$ is

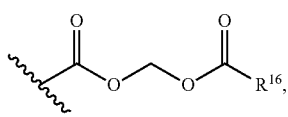

and $R^{16}$ is hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), or -alkyl-(substituted or unsubstituted $C_2$-$C_6$ heterocycloalkyl).

In some embodiments, —$CO_2$—$R^{1b}$ is

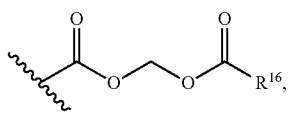

and $R^{16}$ is substituted or unsubstituted $C_2$-$C_6$ heterocycloalkyl, substituted or unsubstituted heteroaryl, -alkyl-(substituted or unsubstituted heteroaryl), or -alkyl-(substituted or unsubstituted $C_2$-$C_6$ heterocycloalkyl). In some embodiments, —$CO_2$—$R^{1b}$ is

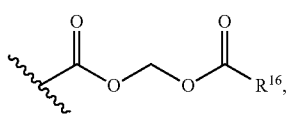

and $R^{16}$ is substituted or unsubstituted $C_2$-$C_6$ heterocycloalkyl, substituted or unsubstituted heteroaryl, —$CH_2$-(substituted or unsubstituted heterocycloalkyl), —$(CH_2)_2$-(substituted or unsubstituted heterocycloalkyl), —$(CH_2)_3$-(substituted or unsubstituted heterocycloalkyl), —$CH_2$-(substituted or unsubstituted heteroaryl), —$(CH_2)_2$-(substituted or unsubstituted heteroaryl), or —$(CH_2)_3$-(substituted or unsubstituted heteroaryl). In some embodiments, —$CO_2$—$R^{1b}$ is

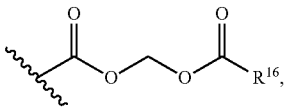

and $R^{16}$ is substituted or unsubstituted $C_2$-$C_6$ heterocycloalkyl, or substituted or unsubstituted heteroaryl.

In some embodiments, —$CO_2$—$R^{1b}$ is

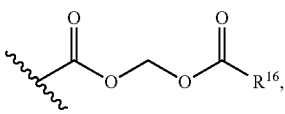

and $R^{16}$ is substituted $C_2$-$C_6$ heterocycloalkyl or substituted heteroaryl. In some embodiments, —$CO_2$—$R^{1b}$ is

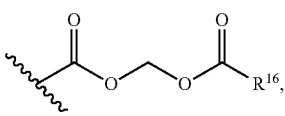

and $R^{16}$ is unsubstituted $C_2$-$C_6$ heterocycloalkyl or unsubstituted heteroaryl. In some embodiments, —$CO_2$—$R^{1b}$ is

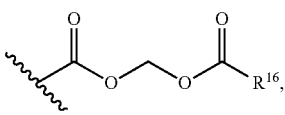

and $R^{16}$ is substituted $C_2$-$C_6$ heterocycloalkyl. In some embodiments, —$CO_2$—$R^{1b}$ is

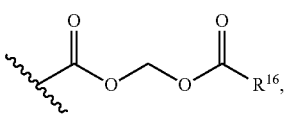

and $R^{16}$ is substituted heteroaryl. In some embodiments, —$CO_2$—$R^{1b}$ is

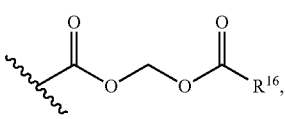

and $R^{16}$ is unsubstituted $C_2$-$C_6$ heterocycloalkyl. In some embodiments, —$CO_2$—$R^{1b}$ is

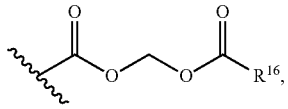

and $R^{16}$ is unsubstituted heteroaryl. In some embodiments, —$CO_2$—$R^{1b}$ is

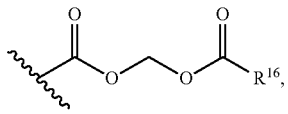

and $R^{16}$ is a benzyl-substituted heteroaryl.

In some embodiments, —$CO_2$—$R^{1b}$ is

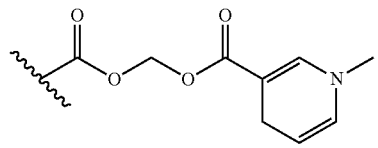

In some embodiments, —$CO_2$—$R^{1b}$ is

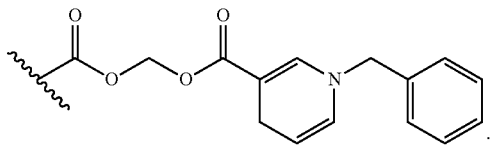 [SMILES: *C(=O)OCOC(=O)C1=CN(Cc2ccccc2)C=CC1]

In some embodiments, $R^{1a}$ is —$CO_2H$, —$CO_2$—$R^{1b}$, or —C(O)N($R^{1c}$)$_2$. In some embodiments, $R^{1a}$ is —$CO_2H$ or —C(O)N($R^{1c}$)$_2$. In some embodiments, $R^{1a}$ is —C(O)N($R^{1c}$)$_2$. In some embodiments, $R^{1a}$ is —C(O)N($R^{1c}$)$_2$; and each $R^{1c}$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$ heterocycloalkyl. In some embodiments, $R^{1a}$ is —C(O)N($R^{1c}$)$_2$; and each $R^{1c}$ is independently hydrogen, $C_1$-$C_6$ alkyl, or $C_1$-$C_6$ deuteroalkyl. In some embodiments, each $R^{1c}$ is independently hydrogen or $C_1$-$C_6$ alkyl. In some embodiments, each $R^{1c}$ is independently hydrogen, —$CH_3$, —$CH_2CH_3$, —$CH_2D$, —$CHD_2$, —$CD_3$, —$CH_2CH_2D$, —$CH_2CHD_2$, —$CH_2CD_3$, or -$CD_2CD_3$. In some embodiments, each $R^{1c}$ is independently hydrogen, —$CH_3$, —$CH_2CH_3$, —$CD_3$, or -$CD_2CD_3$. In some embodiments, each $R^{1c}$ is independently hydrogen, —$CH_3$, or -$CD_3$. In some embodiments, each $R^{1c}$ is independently hydrogen or —$CH_3$. In some embodiments, each $R^{1c}$ is independently hydrogen or -$CD_3$. In some embodiments, each $R^{1c}$ is hydrogen. In some embodiments, each $R^{1c}$ is —$CH_3$. In some embodiments, each $R^{1c}$ is —$CD_3$.

In some embodiments, $R^2$ is hydrogen, —$CH_3$, —$CH_2CH_3$, —$CD_3$, —$CH_2CD_3$, —$CF_3$, or —$CH_2CF_3$; $R^3$ is hydrogen, —$CH_3$, —$CH_2CH_3$, —$CD_3$, —$CH_2CD_3$, —$CF_3$, or —$CH_2CF_3$; or $R^2$ and $R^3$ are taken together with the carbon atom to which they are attached to form a ring B that is a substituted or unsubstituted oxetane, substituted or unsubstituted thietane 1,1-dioxide, or substituted or unsubstituted azetidine.

In some embodiments, $R^2$ is hydrogen, —$CH_3$, —$CD_3$, or —$CF_3$; $R^3$ is hydrogen, —$CH_3$, —$CD_3$, or —$CF_3$; or $R^2$ and $R^3$ are taken together with the carbon atom to which they are attached to form a ring B that is a substituted or unsubstituted oxetane, substituted or unsubstituted thietane 1,1-dioxide, or substituted or unsubstituted azetidine.

In some embodiments, $R^6$ is hydrogen, halogen, —CN, $C_1$-$C_6$ alkyl, $C_1$-$C_6$ deuteroalkyl, $C_1$-$C_6$ fluoroalkyl, —$OR^{16}$, —C(=O)$R^{16}$, —$CO_2R^{16}$, —C(=O)N($R^{16}$)$_2$, —N($R^{16}$)$_2$, —$NR^{16}$C(=O)$R^{16}$, substituted or unsubstituted $C_3$-$C_6$ cycloalkyl, substituted or unsubstituted $C_2$-$C_6$heterocycloalkyl, substituted or unsubstituted phenyl, or substituted or unsubstituted heteroaryl; wherein if $R^6$ is substituted then it is substituted with one or more $R^{13}$; or $R^5$ and $R^6$ are taken together, with the intervening atoms to which they are attached, to form a fused ring D that is a substituted or unsubstituted 5- or 6-membered carbocycle or substituted or unsubstituted 5- or 6-membered heterocycle, wherein if ring D is substituted then it is substituted with one or more $R^{14}$.

In some embodiments, $R^6$ is hydrogen, halogen, —CN, $C_1$-$C_6$ alkyl, $C_1$-$C_6$ deuteroalkyl, $C_1$-$C_6$ fluoroalkyl, —$OR^{16}$, —C(=O)$R^{16}$, —$CO_2R^{16}$, —C(=O)N($R^{16}$)$_2$, —N($R^{16}$)$_2$, or —$NR^{16}$C(=O)$R^{16}$. In some embodiments, $R^6$ is hydrogen, —F, —Cl, —Br, —CN, —$CH_3$, —$CH_2CH_3$, —(CH$_2$)$_2$CH$_3$, —(CH$_2$)$_3$CH$_3$, —CH(CH$_3$)$_2$, —C(CH$_3$)$_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, —$CF_2CF_3$, —OH, —$OCH_3$, —$OCH_2CH_3$, —$OCF_3$, —$CO_2H$, —$CO_2CH_3$, —$CO_2CH_2CH_3$, —C(=O)NH$_2$, —C(=O)NHCH$_3$, —C(=O)N(CH$_3$)$_2$, —NH$_2$, —NHCH$_3$, or —N(CH$_3$)$_2$.

In some embodiments, $R^6$ is hydrogen, halogen, —CN, $C_1$-$C_6$ alkyl, $C_1$-$C_6$ deuteroalkyl, $C_1$-$C_6$ fluoroalkyl. In some embodiments, $R^6$ is hydrogen, —F, —Cl, —Br, —CN, —$CH_3$, —$CH_2CH_3$, —(CH$_2$)$_2$CH$_3$, —(CH$_2$)$_3$CH$_3$, —CH(CH$_3$)$_2$, —C(CH$_3$)$_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$.

In some embodiments, $R^6$ is hydrogen, halogen, or —CN. In some embodiments, $R^6$ is hydrogen, —F, —Cl, —Br, or —CN. In some embodiments, $R^6$ is hydrogen, —F, —Cl, or —CN. In some embodiments, $R^6$ is —F, or —$C_1$. In some embodiments, $R^6$ is hydrogen. In some embodiments, $R^6$ is —F. In some embodiments, $R^6$ is —$C_1$. In some embodiments, $R^6$ is —CN.

In some embodiments, $R^6$ is $C_1$-$C_6$ alkyl, $C_1$-$C_6$ deuteroalkyl, $C_1$-$C_6$ fluoroalkyl. In some embodiments, $R^6$ is —$CH_3$, —$CH_2CH_3$, —(CH$_2$)$_2$CH$_3$, —(CH$_2$)$_3$CH$_3$, —CH(CH$_3$)$_2$, —C(CH$_3$)$_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^6$ is —$CH_3$, —$CH_2CH_3$, —CH(CH$_3$)$_2$, —$CD_3$, —$CH_2F$, —$CHF_2$, or —$CF_3$. In some embodiments, $R^6$ is —$CH_3$, —$CD_3$, —$CH_2F$, —$CHF_2$, or —$CF_3$.

In some embodiments, $R^6$ is —$OR^{16}$, —C(=O)$R^{16}$, —$CO_2R^{16}$, —C(=O)N($R^{16}$)$_2$, —N($R^{16}$)$_2$, or —$NR^{16}$C(=O)$R^{16}$. In some embodiments, $R^6$ is —OH, —$OCH_3$, —$OCH_2CH_3$, —$OCF_3$, —$CO_2H$, —$CO_2CH_3$, —$CO_2CH_2CH_3$, —C(=O)NH$_2$, —C(=O)NHCH$_3$, —C(=O)N(CH$_3$)$_2$, —NH$_2$, —NHCH$_3$, or —N(CH$_3$)$_2$.

In some embodiments, $R^6$ is a substituted or unsubstituted $C_3$-$C_6$ cycloalkyl, substituted or unsubstituted $C_2$-$C_6$ heterocycloalkyl, substituted or unsubstituted phenyl, or substituted or unsubstituted heteroaryl, wherein if $R^6$ is substituted then it is substituted with one or more $R^{13}$.

In some embodiments, $R^6$ is an unsubstituted $C_3$-$C_6$ cycloalkyl, unsubstituted $C_2$-$C_6$ heterocycloalkyl, unsubstituted phenyl, or unsubstituted heteroaryl. In some embodiments, $R^6$ is a substituted $C_3$-$C_6$ cycloalkyl, substituted $C_2$-$C_6$ heterocycloalkyl, substituted phenyl, or substituted heteroaryl, each of which is substituted with one or more $R^{13}$.

In some embodiments, $R^6$ is a substituted or unsubstituted $C_3$-$C_6$ cycloalkyl, or substituted or unsubstituted phenyl. In some embodiments, $R^6$ is a substituted or unsubstituted $C_3$-$C_6$ cycloalkyl.

In some embodiments, $R^6$ is a substituted or unsubstituted cyclopropyl. In some embodiments, $R^6$ is an unsubstituted cyclopropyl. In some embodiments,

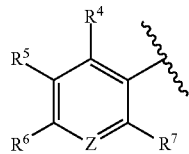

is

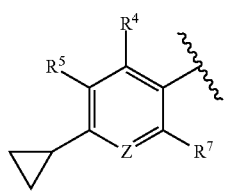

In some embodiments, $R^6$ is a cyclopropyl substituted with one or more $R^{13}$.

In some embodiments,

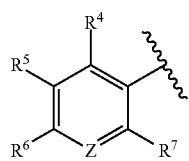

is

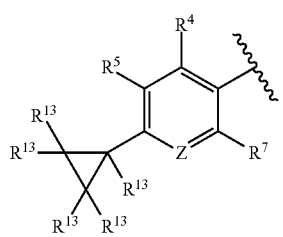

In some embodiments, $R^6$ is a substituted or unsubstituted phenyl or substituted or unsubstituted 6-membered heteroaryl. In some embodiments, $R^6$ is substituted or unsubstituted phenyl, substituted or unsubstituted pyridinyl, substituted or unsubstituted pyrimidinyl, substituted or unsubstituted pyridazinyl, substituted or unsubstituted pyrazinyl, substituted or unsubstituted triazinyl, or substituted or unsubstituted tetrazinyl, or a tautomer thereof. In some embodiments, $R^6$ is substituted or unsubstituted phenyl, substituted or unsubstituted pyridinyl, or substituted or unsubstituted pyrimidinyl. In some embodiments, $R^6$ is a substituted or unsubstituted phenyl. In some embodiments, $R^6$ is a substituted or unsubstituted pyridinyl. In some embodiments, $R^6$ is a substituted or unsubstituted pyrimidinyl.

In some embodiments,

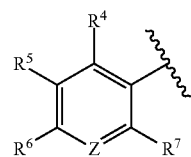

is

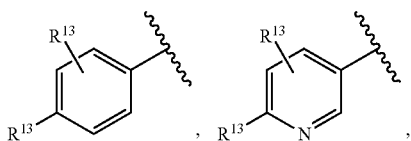

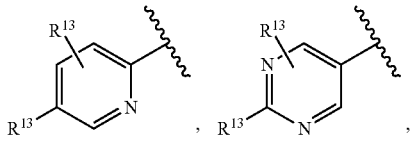

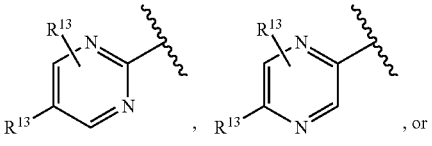

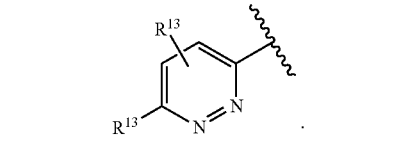

, or

In some embodiments, $R^6$ is a phenyl substituted with one or more $R^{13}$. In some embodiment,

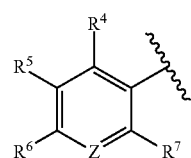

is

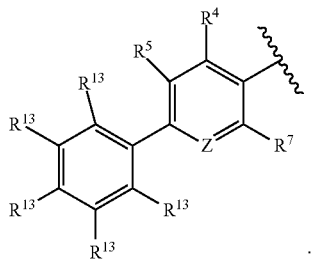

In some embodiments,

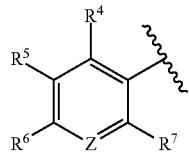

is

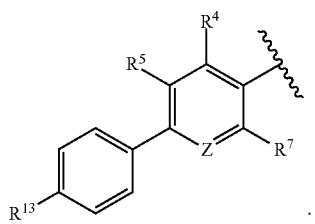

In some embodiments, R is an unsubstituted phenyl. In some embodiments,

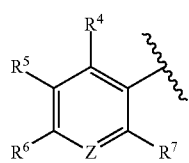

is

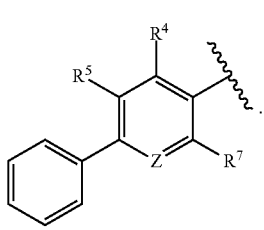

In some embodiments, $R^{13}$ is —CN. In some embodiments,

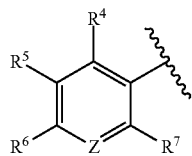

is

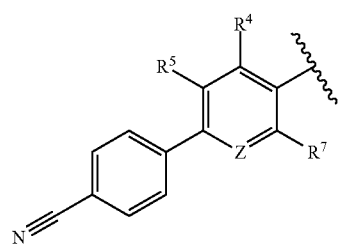

In some embodiments, the compound of Formula (I) has the following structure of Formula (XIII-A):

Formula (XIII-A)

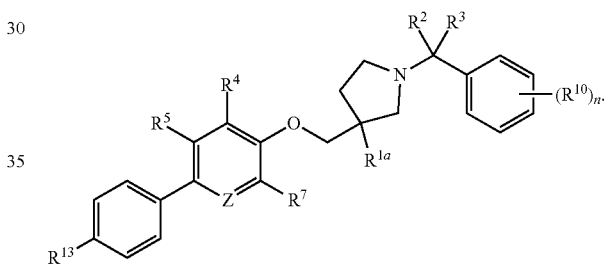

or a pharmaceutically acceptable salt, or solvate thereof.

In some embodiments of a compound of Formula (XIII-A), $R^2$ and $R^3$ are taken together with the carbon atom to which they are attached to form a ring B that is a substituted or unsubstituted $C_3$-$C_6$ cycloalkyl, or substituted or unsubstituted $C_2$-$C_6$ heterocycloalkyl, wherein if the ring B is substituted then it is substituted with one or more $R^{12}$. In some embodiments of a compound of Formula (XIII-A), $R^2$ and $R^3$ are taken together with the carbon atom to which they are attached to form a ring B that is an oxetane, azetidine, thietane 1-oxide, or thietane 1,1-dioxide.

In some embodiments, the compound of Formula (I) has the following structure of Formula (XIII-B) or (XIII-C):

Formula (XIII-B)

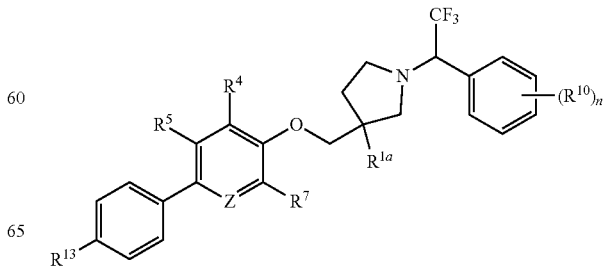

-continued

Formula (XIII-C)

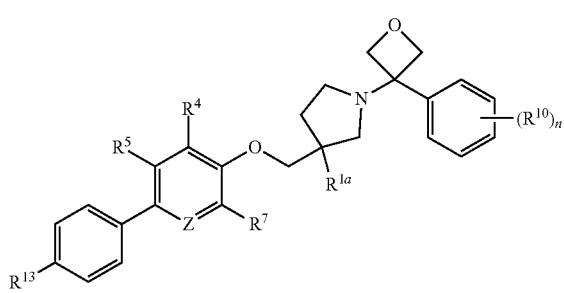

or a pharmaceutically acceptable salt, or solvate thereof.

In some embodiments, the compound of Formula (X) has the following structure of Formula (XIV):

Formula (XIV)

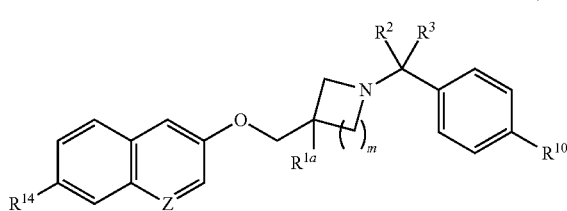

or a pharmaceutically acceptable salt, or solvate thereof.

In some embodiments, the compound of Formula (X) has the following structure of Formula (XV) or Formula (XVI):

Formula (XV)

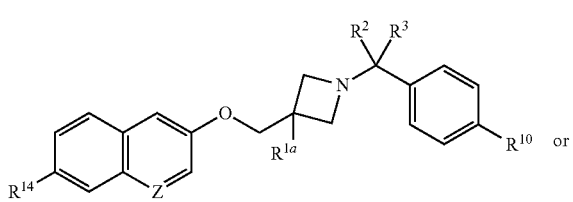

or

Formula (XVI)

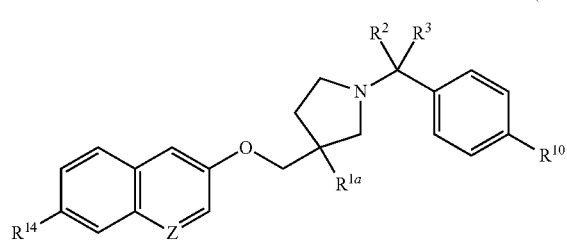

or a pharmaceutically acceptable salt, or solvate thereof.

In some embodiments, $R^6$ is a substituted or unsubstituted $C_2$-$C_6$ heterocycloalkyl or unsubstituted heteroaryl. In some embodiments, $R^6$ is a substituted or unsubstituted $C_2$-$C_6$ heterocycloalkyl. In some embodiments, $R^6$ is a substituted or unsubstituted oxetane, azetidine, or thietane 1,1-dioxide.

In some embodiments, $R^6$ is a substituted oxetane, azetidine, or thietane 1,1-dioxide, wherein each $R^6$ is substituted with one or more $R^{13}$. In some embodiments,

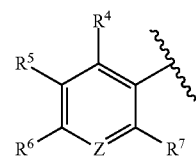

is

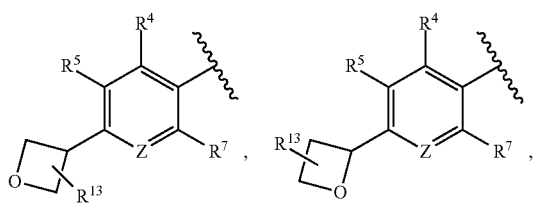

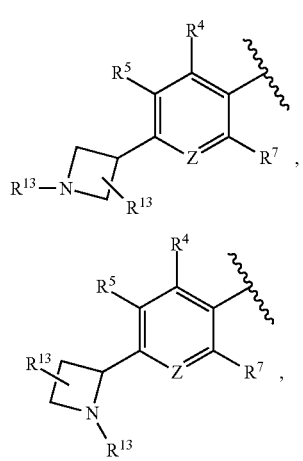

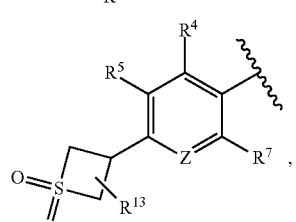

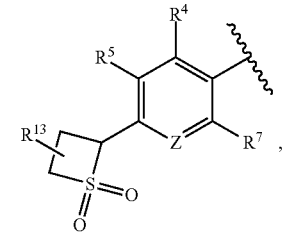

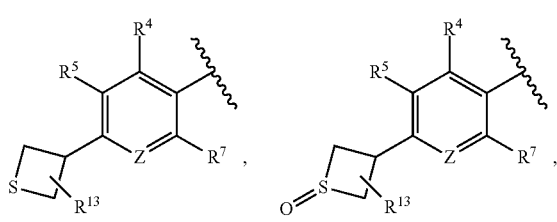

-continued

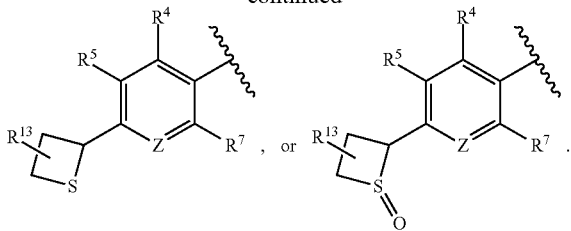

In some embodiments,

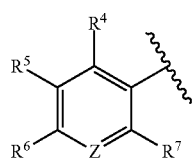

is

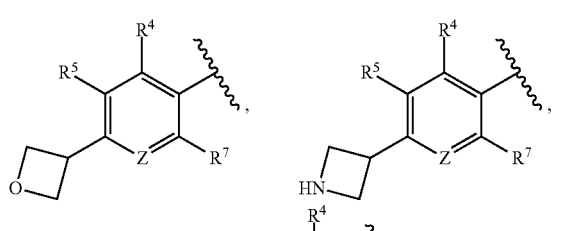

In some embodiments, $R^6$ is a substituted or unsubstituted heteroaryl. In some embodiments, $R^6$ is a substituted or unsubstituted pyridinyl, pyrazinyl, pyridazinyl, or pyrimidinyl.

In some embodiments, $R^5$ and $R^6$ are taken together, with the intervening atoms to which they are attached, to form a fused ring D that is a substituted or unsubstituted 5- or 6-membered carbocycle or substituted or unsubstituted 5- or 6-membered heterocycle, wherein if ring D is substituted then it is substituted with one or more $R^{14}$.

In some embodiments, $R^5$ and $R^6$ are taken together, with the intervening atoms to which they are attached, to form a fused substituted or unsubstituted ring D that is a fused substituted or unsubstituted phenyl, a fused substituted or unsubstituted pyridinyl, or a fused substituted or unsubstituted cyclohexyl, wherein if ring D is substituted then it is substituted with one or more $R^{14}$.

In some embodiments, $R^5$ and $R^6$ are taken together, with the intervening atoms to which they are attached, to form a fused substituted or unsubstituted phenyl, wherein if ring D is substituted then it is substituted with one or more $R^{14}$. In some embodiments, $R^5$ and $R^6$ are taken together, with the intervening atoms to which they are attached, to form a fused unsubstituted phenyl. In some embodiments,

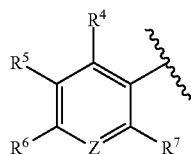

is

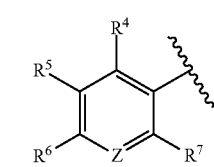

In some embodiments, $R^5$ and $R^6$ are taken together, with the intervening atoms to which they are attached, to form a fused phenyl, substituted with one or more $R^{14}$. In some embodiments,

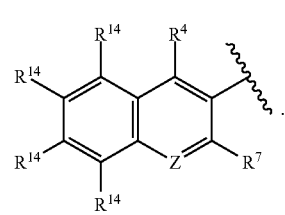

is

In some embodiments,

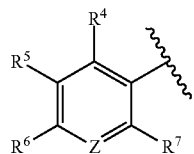

is

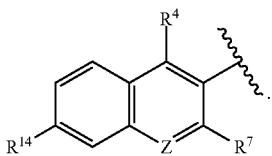

In some embodiments, $R^5$ and $R^6$ are taken together, with the intervening atoms to which they are attached, to form a fused substituted or unsubstituted pyridinyl, wherein if ring D is substituted then it is substituted with one or more $R^{14}$. In some embodiments, $R^5$ and $R^6$ are taken together, with the intervening atoms to which they are attached, to form a fused unsubstituted pyridinyl. In some embodiments,

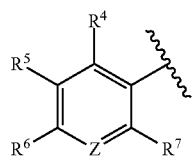

is

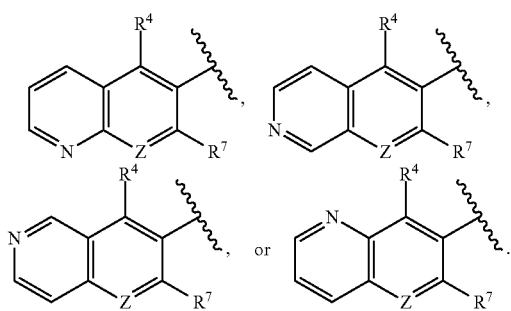

In some embodiments, $R^5$ and $R^6$ are taken together, with the intervening atoms to which they are attached, to form a fused pyridinyl, substituted with one or more $R^{14}$. In some embodiments,

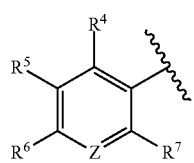

is

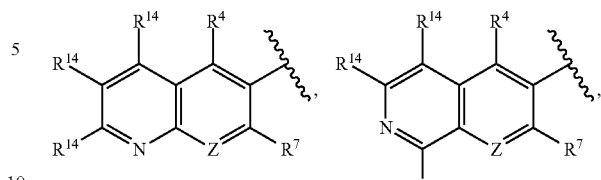

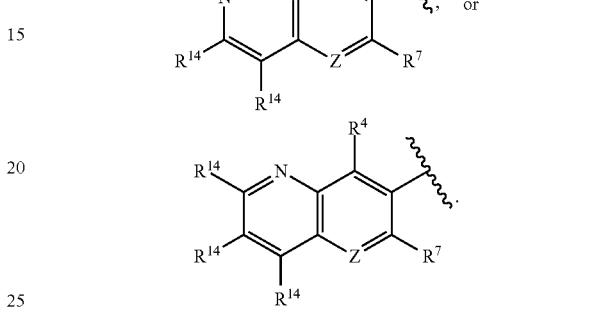

In some embodiments,

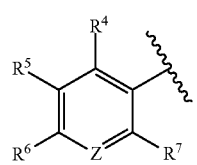

is

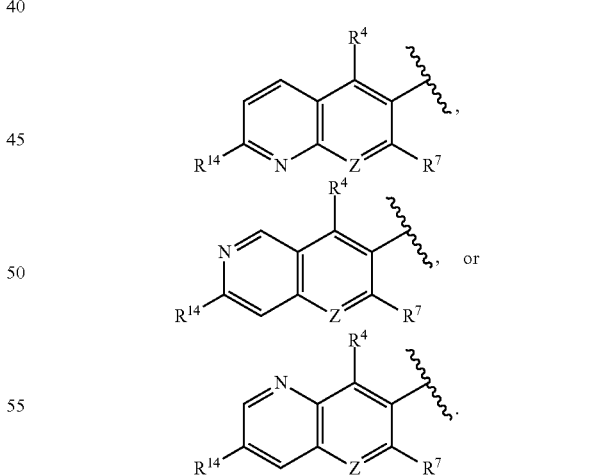

In some embodiments, $R^5$ and $R^6$ are taken together, with the intervening atoms to which they are attached, to form a fused substituted or unsubstituted cyclohexyl, wherein if ring D is substituted then it is substituted with one or more $R^{14}$. In some embodiments, $R^5$ and $R^6$ are taken together, with the intervening atoms to which they are attached, to form a fused unsubstituted cyclohexyl. In some embodiments, is

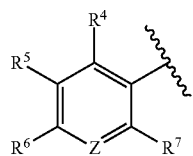

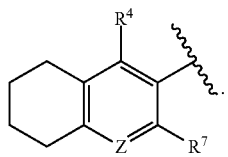

In some embodiments, $R^5$ and $R^6$ are taken together, with the intervening atoms to which they are attached, to form a fused cyclohexyl, substituted with one or more $R^{14}$. In some embodiments,

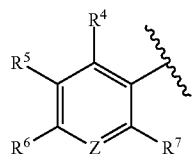

is

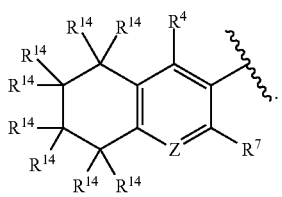

In some embodiments,

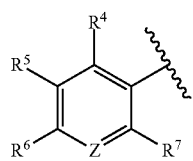

is

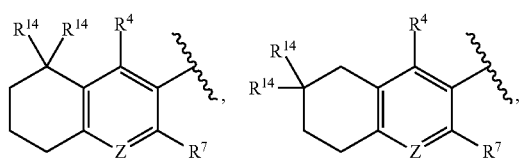

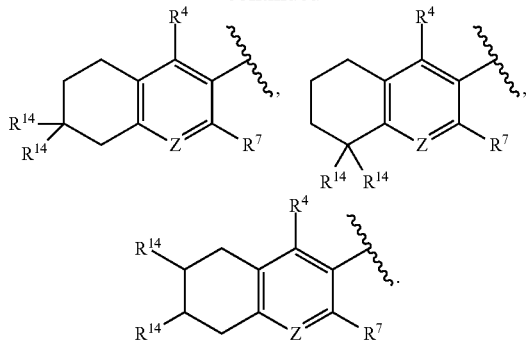

In some embodiments,

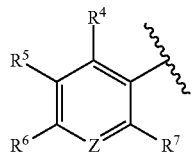

is

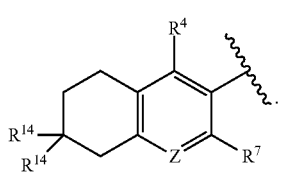

In some embodiments,

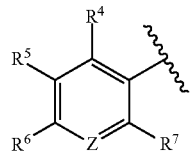

is

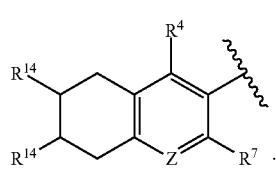

In some embodiments, $R^4$ is hydrogen, halogen, —CN, $C_1$-$C_6$ alkyl, $C_1$-$C_6$ deuteroalkyl, $C_1$-$C_6$ fluoroalkyl, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$. In some embodiments, $R^4$ is hydrogen, —F, —Cl, —Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, —CF$_2$CF$_3$, —OH, —OCH$_3$, —OCH$_2$CH$_3$, —OCF$_3$, —CO$_2$H, —CO$_2$CH$_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^4$ is hydrogen, halogen, —CN, $C_1$-$C_6$ alkyl, $C_1$-$C_6$ deuteroalkyl, $C_1$-$C_6$ fluoroalkyl. In some embodiments, $R^4$ is hydrogen, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$.

In some embodiments, $R^4$ is hydrogen, halogen, or —CN. In some embodiments, $R^4$ is hydrogen, —F, —Cl, —Br, or —CN. In some embodiments, $R^4$ is hydrogen, —F, —Cl, or —CN. In some embodiments, $R^4$ is —F, or —Cl. In some embodiments, $R^4$ is hydrogen. In some embodiments, $R^4$ is —F. In some embodiments, $R^4$ is —Cl. In some embodiments, $R^4$ is —CN.

In some embodiments, $R^4$ is $C_1$-$C_6$ alkyl, $C_1$-$C_6$ deuteroalkyl, $C_1$-$C_6$ fluoroalkyl. In some embodiments, $R^4$ is —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^4$ is —$CH_3$, —$CH_2CH_3$, —$CH(CH_3)_2$, —$CD_3$, —$CH_2F$, —$CHF_2$, or —$CF_3$. In some embodiments, $R^4$ is —$CH_3$, —$CD_3$, —$CH_2F$, —$CHF_2$, or —$CF_3$.

In some embodiments, $R^4$ is —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^4$ is —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^5$ is hydrogen, halogen, —CN, $C_1$-$C_6$ alkyl, $C_1$-$C_6$ deuteroalkyl, $C_1$-$C_6$ fluoroalkyl, —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^5$ is hydrogen, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, —$CF_2CF_3$, —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^5$ is hydrogen, halogen, —CN, $C_1$-$C_6$ alkyl, $C_1$-$C_6$ deuteroalkyl, $C_1$-$C_6$ fluoroalkyl. In some embodiments, $R^5$ is hydrogen, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$.

In some embodiments, $R^5$ is hydrogen, halogen, or —CN. In some embodiments, $R^5$ is hydrogen, —F, —Cl, —Br, or —CN. In some embodiments, $R^5$ is hydrogen, —F, —Cl, or —CN. In some embodiments, $R^5$ is —F, or —$C_1$. In some embodiments, $R^5$ is hydrogen. In some embodiments, $R^5$ is —F. In some embodiments, $R^5$ is —$C_1$. In some embodiments, $R^5$ is —CN.

In some embodiments, $R^5$ is $C_1$-$C_6$ alkyl, $C_1$-$C_6$ deuteroalkyl, $C_1$-$C_6$ fluoroalkyl. In some embodiments, $R^5$ is —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^5$ is —$CH_3$, —$CH_2CH_3$, —$CH(CH_3)_2$, —$CD_3$, —$CH_2F$, —$CHF_2$, or —$CF_3$. In some embodiments, $R^5$ is —$CH_3$, —$CD_3$, —$CH_2F$, —$CHF_2$, or —$CF_3$.

In some embodiments, $R^5$ is —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^5$ is —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^7$ is hydrogen, halogen, —CN, $C_1$-$C_6$ alkyl, $C_1$-$C_6$ deuteroalkyl, $C_1$-$C_6$ fluoroalkyl, —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^7$ is hydrogen, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, —$CF_2CF_3$, —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^7$ is hydrogen, halogen, —CN, $C_1$-$C_6$ alkyl, $C_1$-$C_6$ deuteroalkyl, $C_1$-$C_6$ fluoroalkyl. In some embodiments, $R^7$ is hydrogen, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$.

In some embodiments, $R^7$ is hydrogen, halogen, or —CN. In some embodiments, $R^7$ is hydrogen, —F, —Cl, —Br, or —CN. In some embodiments, $R^7$ is hydrogen, —F, —Cl, or —CN. In some embodiments, $R^7$ is —F, or —Cl. In some embodiments, $R^7$ is hydrogen. In some embodiments, $R^7$ is —F. In some embodiments, $R^7$ is —Cl. In some embodiments, $R^7$ is —CN.

In some embodiments, $R^7$ is $C_1$-$C_6$ alkyl, $C_1$-$C_6$ deuteroalkyl, $C_1$-$C_6$ fluoroalkyl. In some embodiments, $R^7$ is —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^7$ is —$CH_3$, —$CH_2CH_3$, —$CH(CH_3)_2$, —$CD_3$, —$CH_2F$, —$CHF_2$, or —$CF_3$. In some embodiments, $R^7$ is —$CH_3$, —$CD_3$, —$CH_2F$, —$CHF_2$, or —$CF_3$.

In some embodiments, $R^7$ is —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^7$ is —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^8$ is hydrogen, halogen, —CN, $C_1$-$C_6$ alkyl, $C_1$-$C_6$ deuteroalkyl, $C_1$-$C_6$ fluoroalkyl, —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^8$ is hydrogen, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, —$CF_2CF_3$, —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^8$ is hydrogen, halogen, —CN, $C_1$-$C_6$ alkyl, $C_1$-$C_6$ deuteroalkyl, $C_1$-$C_6$ fluoroalkyl. In some embodiments, $R^8$ is hydrogen, —F, —Cl, —Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, or —CF$_2$CF$_3$.

In some embodiments, R$^8$ is hydrogen, halogen, or —CN. In some embodiments, R$^8$ is hydrogen, —F, —Cl, —Br, or —CN. In some embodiments, R$^8$ is hydrogen, —F, —Cl, or —CN. In some embodiments, R$^8$ is —F, or —Cl. In some embodiments, R$^8$ is hydrogen. In some embodiments, R$^8$ is —F. In some embodiments, R$^8$ is —Cl. In some embodiments, R$^8$ is —CN.

In some embodiments, R$^8$ is C$_1$-C$_6$ alkyl, C$_1$-C$_6$ deuteroalkyl, C$_1$-C$_6$ fluoroalkyl. In some embodiments, R$^8$ is —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, or —CF$_2$CF$_3$. In some embodiments, R$^8$ is —CH$_3$, —CH$_2$CH$_3$, —CH(CH$_3$)$_2$, —CD$_3$, —CH$_2$F, —CHF$_2$, or —CF$_3$. In some embodiments, R$^8$ is —CH$_3$, —CD$_3$, —CH$_2$F, —CHF$_2$, or —CF$_3$.

In some embodiments, R$^8$ is —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$. In some embodiments, R$^8$ is —OH, —OCH$_3$, —OCH$_2$CH$_3$, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, or —N(CH$_3$)$_2$.

In some embodiments, R$^4$, R$^5$, R$^7$, and R$^8$ are each independently hydrogen; R$^6$ is hydrogen, halogen, —CN, C$_1$-C$_6$ alkyl, C$_1$-C$_6$ deuteroalkyl, C$_1$-C$_6$ fluoroalkyl, —OR$^{16}$, —C(=O)R$^{16}$, —CO$_2$R$^{16}$, —C(=O)N(R$^{16}$)$_2$, —N(R$^{16}$)$_2$, —NR$^{16}$C(=O)R$^{16}$, substituted or unsubstituted C$_3$-C$_6$ cycloalkyl, substituted or unsubstituted C$_2$-C$_6$ heterocycloalkyl, substituted or unsubstituted phenyl, or substituted or unsubstituted heteroaryl, wherein if R$^6$ is substituted then it is substituted with one or more R$^{13}$; or R$^5$ and R$^6$ are taken together, with the intervening atoms to which they are attached, to form a fused substituted or unsubstituted ring D that is a fused substituted or unsubstituted phenyl, a fused substituted or unsubstituted pyridinyl, or a fused substituted or unsubstituted cyclohexyl, wherein if ring D is substituted then it is substituted with one or more R$^{14}$.

In some embodiments, R$^4$, R$^5$, R$^7$, and R$^8$ are each independently hydrogen; R$^6$ is hydrogen, halogen, —CN, C$_1$-C$_6$ alkyl, substituted or unsubstituted C$_3$-C$_6$ cycloalkyl, substituted or unsubstituted C$_2$-C$_6$ heterocycloalkyl, or substituted or unsubstituted phenyl. In some embodiments, R$^4$, R$^5$, R$^7$, and R$^8$ are each independently hydrogen; and R$^6$ is hydrogen, —F, —Cl, —CN, —CH$_3$, substituted or unsubstituted cyclopropyl, substituted or unsubstituted oxetanyl, substituted or unsubstituted azetinyl, substituted or unsubstituted thietane 1,1-dioxide, or substituted or unsubstituted phenyl. In some embodiments, R$^4$, R$^5$, R$^7$, and R$^8$ are each independently hydrogen; and R$^6$ is hydrogen, —CN, substituted or unsubstituted oxetanyl, or substituted or unsubstituted phenyl. In some embodiments, R$^4$, R$^5$, R$^6$, R$^7$, and R$^8$ are each independently hydrogen. In some embodiments, R$^4$, R$^5$, R$^7$, and R$^8$ are each independently hydrogen; and R$^6$ is —CN. In some embodiments, R$^4$, R$^5$, R$^7$, and R$^8$ are each independently hydrogen; and R$^6$ hydrogen, —CN, substituted or unsubstituted oxetanyl, or substituted or unsubstituted phenyl. In some embodiments, R$^4$, R$^5$, R$^7$, and R$^8$ are each independently hydrogen; and R$^6$ is a substituted or unsubstituted oxetanyl. In some embodiments, R$^4$, R$^5$, R$^7$, and R$^8$ are each independently hydrogen; and R$^6$ is a substituted or unsubstituted phenyl.

In some embodiments, R$^{10}$ is hydrogen, deuterium, halogen, —CN, C$_1$-C$_6$ alkyl, C$_1$-C$_6$ deuteroalkyl, C$_1$-C$_6$ fluoroalkyl, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$. In some embodiments, R$^{10}$ is hydrogen, deuterium, —F, —Cl, —Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, —CF$_2$CF$_3$, —OH, —OCH$_3$, —OCH$_2$CH$_3$, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, or —N(CH$_3$)$_2$.

In some embodiments, R$^{10}$ is hydrogen, deuterium, halogen, —CN, C$_1$-C$_6$ alkyl, C$_1$-C$_6$ deuteroalkyl, C$_1$-C$_6$ fluoroalkyl. In some embodiments, R$^{10}$ is hydrogen, —F, —Cl, —Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, or —CF$_2$CF$_3$.

In some embodiments, R$^{10}$ is hydrogen, halogen, or —CN. In some embodiments, R$^{10}$ is hydrogen, —F, —Cl, —Br, or —CN. In some embodiments, R$^{10}$ is —F, —Cl, or —CN. In some embodiments, R$^{10}$ is —F or —Cl. In some embodiments, R$^{10}$ is hydrogen. In some embodiments, R$^{10}$ is deuterium. In some embodiments, R$^{10}$ is —F. In some embodiments, R$^{10}$ is —Cl. In some embodiments, R$^{10}$ is —CN.

In some embodiments, R$^{10}$ is C$_1$-C$_6$ alkyl, C$_1$-C$_6$ deuteroalkyl, C$_1$-C$_6$ fluoroalkyl. In some embodiments, R$^{10}$ is —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, or —CF$_2$CF$_3$. In some embodiments, R$^{10}$ is —CH$_3$, —CH$_2$CH$_3$, —CH(CH$_3$)$_2$, —CD$_3$, —CH$_2$F, —CHF$_2$, or —CF$_3$. In some embodiments, R$^{10}$ is —CH$_3$, —CD$_3$, —CH$_2$F, —CHF$_2$, or —CF$_3$.

In some embodiments, R$^{10}$ is —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$. In some embodiments, R$^{10}$ is —OH, —OCH$_3$, —OCH$_2$CH$_3$, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, or —N(CH$_3$)$_2$.

In some embodiments, R$^{12}$ is hydrogen, deuterium, halogen, —CN, C$_1$-C$_6$ alkyl, C$_1$-C$_6$ deuteroalkyl, C$_1$-C$_6$ fluoroalkyl, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$. In some embodiments, R$^{12}$ is hydrogen, deuterium, —F, —Cl, —Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, —CF$_2$CF$_3$, —OH, —OCH$_3$, —OCH$_2$CH$_3$, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, or —N(CH$_3$)$_2$.

In some embodiments, R$^{12}$ is hydrogen, deuterium, halogen, —CN, C$_1$-C$_6$ alkyl, C$_1$-C$_6$ deuteroalkyl, C$_1$-C$_6$ fluoroalkyl. In some embodiments, R$^{12}$ is hydrogen, —F, —Cl, —Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$D, —CHD$_2$, —CD$_3$, —CH$_2$CH$_2$D, —CH$_2$CHD$_2$, —CH$_2$CD$_3$, —CD$_2$CD$_3$, —CH$_2$F, —CHF$_2$, —CF$_3$, —CH$_2$CH$_2$F, —CH$_2$CHF$_2$, —CH$_2$CF$_3$, or —CF$_2$CF$_3$.

In some embodiments, $R^{12}$ is hydrogen, halogen, or —CN. In some embodiments, $R^{12}$ is hydrogen, —F, —Cl, —Br, or —CN. In some embodiments, $R^{12}$ is —F, —Cl, or —CN. In some embodiments, $R^{12}$ is —F or —$C_1$. In some embodiments, $R^{12}$ is hydrogen. In some embodiments, $R^{12}$ is deuterium. In some embodiments, $R^{12}$ is —F. In some embodiments, $R^{12}$ is —$C_1$. In some embodiments, $R^{12}$ is —CN.

In some embodiments, $R^{12}$ is $C_1$-$C_6$ alkyl, $C_1$-$C_6$ deuteroalkyl, $C_1$-$C_6$ fluoroalkyl. In some embodiments, $R^{12}$ is —$CH_3$, —$CH_2CH_3$, —$(CH_2)_2CH_3$, —$(CH_2)_3CH_3$, —CH$(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^{12}$ is —$CH_3$, —$CH_2CH_3$, —$CH(CH_3)_2$, —$CD_3$, —$CH_2F$, —$CHF_2$, or —$CF_3$. In some embodiments, $R^{12}$ is —$CH_3$, —$CD_3$, —$CH_2F$, —$CHF_2$, or —$CF_3$.

In some embodiments, $R^{12}$ is —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^{12}$ is —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^{13}$ is hydrogen, deuterium, halogen, —CN, $C_1$-$C_6$ alkyl, $C_1$-$C_6$ deuteroalkyl, $C_1$-$C_6$ fluoroalkyl, —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^{13}$ is hydrogen, deuterium, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, —$CF_2CF_3$, —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^{13}$ is hydrogen, deuterium, halogen, —CN, $C_1$-$C_6$ alkyl, $C_1$-$C_6$ deuteroalkyl, $C_1$-$C_6$ fluoroalkyl. In some embodiments, $R^{13}$ is hydrogen, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$.

In some embodiments, $R^{13}$ is hydrogen, halogen, or —CN. In some embodiments, $R^{13}$ is hydrogen, —F, —Cl, —Br, or —CN. In some embodiments, $R^{13}$ is —F, —Cl, or —CN. In some embodiments, $R^{13}$ is —F or —Cl. In some embodiments, $R^{13}$ is hydrogen. In some embodiments, $R^{13}$ is deuterium. In some embodiments, $R^{13}$ is —F. In some embodiments, $R^{13}$ is —Cl. In some embodiments, $R^{13}$ is —CN.

In some embodiments, $R^{13}$ is $C_1$-$C_6$ alkyl, $C_1$-$C_6$ deuteroalkyl, $C_1$-$C_6$ fluoroalkyl. In some embodiments, $R^{13}$ is —$CH_3$, —$CH_2CH_3$, —$(CH_2)_2CH_3$, —$(CH_2)_3CH_3$, —CH$(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^{13}$ is —$CH_3$, —$CH_2CH_3$, —$CH(CH_3)_2$, —$CD_3$, —$CH_2F$, —$CHF_2$, or —$CF_3$. In some embodiments, $R^{13}$ is —$CH_3$, —$CD_3$, —$CH_2F$, —$CHF_2$, or —$CF_3$.

In some embodiments, $R^{13}$ is —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^{13}$ is —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^{14}$ is hydrogen, deuterium, halogen, —CN, $C_1$-$C_6$ alkyl, $C_1$-$C_6$ deuteroalkyl, $C_1$-$C_6$ fluoroalkyl, —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^{14}$ is hydrogen, deuterium, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, —$CF_2CF_3$, —OH, —$OCH_3$, —$OCH_2CH_3$, —$OCF_3$, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In some embodiments, $R^{14}$ is hydrogen, deuterium, halogen, —CN, $C_1$-$C_6$ alkyl, $C_1$-$C_6$ deuteroalkyl, $C_1$-$C_6$ fluoroalkyl. In some embodiments, $R^{14}$ is hydrogen, —F, —Cl, —Br, —CN, —$CH_3$, —$CH_2CH_3$, —$(CH_2)_2CH_3$, —$(CH_2)_3CH_3$, —$CH(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$.

In some embodiments, $R^{14}$ is hydrogen, halogen, or —CN. In some embodiments, $R^{14}$ is hydrogen, —F, —Cl, —Br, or —CN. In some embodiments, $R^{14}$ is —F, —Cl, or —CN. In some embodiments, $R^{14}$ is —F or —Cl. In some embodiments, $R^{14}$ is hydrogen. In some embodiments, $R^{14}$ is deuterium. In some embodiments, $R^{14}$ is —F. In some embodiments, $R^{14}$ is —Cl. In some embodiments, $R^{14}$ is —CN.

In some embodiments, $R^{14}$ is $C_1$-$C_6$ alkyl, $C_1$-$C_6$ deuteroalkyl, $C_1$-$C_6$ fluoroalkyl. In some embodiments, $R^{14}$ is —$CH_3$, —$CH_2CH_3$, —$(CH_2)_2CH_3$, —$(CH_2)_3CH_3$, —CH$(CH_3)_2$, —$C(CH_3)_3$, —$CH_2D$, —$CHD_2$, —$CD_3$, —$CH_2CH_2D$, —$CH_2CHD_2$, —$CH_2CD_3$, —$CD_2CD_3$, —$CH_2F$, —$CHF_2$, —$CF_3$, —$CH_2CH_2F$, —$CH_2CHF_2$, —$CH_2CF_3$, or —$CF_2CF_3$. In some embodiments, $R^{14}$ is —$CH_3$, —$CH_2CH_3$, —$CH(CH_3)_2$, —$CD_3$, —$CH_2F$, —$CHF_2$, or —$CF_3$. In some embodiments, $R^{14}$ is —$CH_3$, —$CD_3$, —$CH_2F$, —$CHF_2$, or —$CF_3$.

In some embodiments, $R^{14}$ is —$OR^{16}$, —$C(=O)R^{16}$, —$CO_2R^{16}$, —$C(=O)N(R^{16})_2$, —$N(R^{16})_2$, or —$NR^{16}C(=O)R^{16}$. In some embodiments, $R^{14}$ is —OH, —$OCH_3$, —$OCH_2CH_3$, —$OCF_3$, —O-cyclopropyl, —O-cyclobutyl, —O-oxetanyl, —O-azetidinyl, —$CO_2H$, —$CO_2CH_3$, —$CO_2CH_2CH_3$, —$C(=O)NH_2$, —$C(=O)NHCH_3$, —$C(=O)N(CH_3)_2$, —$NH_2$, —$NHCH_3$, or —$N(CH_3)_2$.

In another aspect, provided herein is a compound having the structure of Formula (XX):

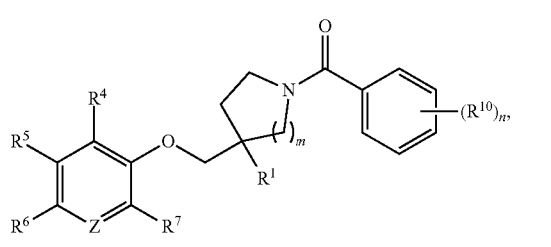

Formula (XX)

or a pharmaceutically acceptable salt, or solvate thereof;
wherein:
R¹ is

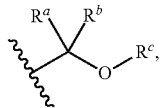

—C(O)NR$^d$R$^e$, —N(R$^f$)$_2$, substituted or unsubstituted monocyclic heterocycle, or substituted or unsubstituted monocyclic carbocycle, wherein if R¹ is a substituted monocyclic heterocycle, then it is substituted with one or more instances of R$^9$;

R$^a$ is hydrogen, deuterium, C$_1$-C$_6$ alkyl, C$_1$-C$_6$ deuteroalkyl, C$_1$-C$_6$ fluoroalkyl;

R$^b$ is hydrogen, deuterium, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, or substituted or unsubstituted C$_2$-C$_6$ heterocycloalkyl;

or R$^a$ and R$^b$ are taken together with the carbon atom to which they are attached to form a ring C that is a substituted or unsubstituted C$_3$-C$_6$cycloalkyl, or substituted or unsubstituted C$_2$-C$_6$ heterocycloalkyl, wherein if the ring C is substituted then it is substituted with one or more R$^{11}$; and R$^c$ is hydrogen, C$_1$-C$_6$ alkyl, or R$^g$;

or R$^a$ and R$^b$ are taken together with the carbon atom to which they are attached to form a carbonyl (C=O); and R$^c$ is C$_3$-C$_6$ alkyl or R$^g$;

R$^d$ is —CN, C$_1$-C$_6$ alkyl, C$_1$-C$_6$ deuteroalkyl, C$_1$-C$_6$ fluoroalkyl, C$_{1-6}$ alkoxy, substituted or unsubstituted C$_3$-C$_6$ cycloalkyl, substituted or unsubstituted C$_2$-C$_6$ heterocycloalkyl, —OH, —OR$^{1d}$, —SOR$^{1d}$, or —SO$_2$R$^{1d}$; wherein R$^{1d}$ is substituted or unsubstituted C$_1$-C$_6$ alkyl, substituted or unsubstituted C$_3$-C$_6$ cycloalkyl, substituted or unsubstituted 3- to 6-membered heterocycloalkyl, substituted or unsubstituted phenyl, or substituted or unsubstituted 5- to 6-membered heteroaryl; wherein if R$^{1d}$ is substituted then it is substituted with one or more R$^{14}$;

R$^e$ is hydrogen, C$_1$-C$_6$ alkyl, C$_1$-C$_6$ deuteroalkyl, C$_1$-C$_6$ fluoroalkyl, C$_{1-6}$ alkoxy, substituted or unsubstituted C$_3$-C$_6$ cycloalkyl, or substituted or unsubstituted C$_2$-C$_6$ heterocycloalkyl;

or R$^d$ and R$^e$ are taken together with the N atom to which they are attached to form a substituted or unsubstituted C$_2$-C$_6$ heterocycloalkyl;

each R$^f$ is independently hydrogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, or substituted or unsubstituted C$_2$-C$_6$heterocycloalkyl;

or both R$^f$ are taken together with the N atom to which they are attached to form a substituted or unsubstituted C$_2$-C$_6$heterocycloalkyl;

R$^g$ is C$_1$-C$_6$ deuteroalkyl, C$_1$-C$_6$ fluoroalkyl, substituted or unsubstituted C$_1$-C$_6$ heteroalkyl, substituted or unsubstituted C$_3$-C$_6$ cycloalkyl, substituted or unsubstituted C$_2$-C$_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted C$_3$-C$_6$ cycloalkyl), -alkyl-(substituted or unsubstituted C$_2$-C$_6$ heterocycloalkyl), —C(=O)R$^{16}$, —C(=O)—OR$^{16}$, —C(=O)N(R$^{16}$)$_2$, —(C(R$^{17}$)$_2$O)$_p$—R$^{15}$, —(CH$_2$CH$_2$O)$_q$—R$^{15}$, or —(C(R$^{17}$)$_2$)$_p$—OR$^{15}$;

Z is N or CR$^8$;

R$^4$, R$^5$, R$^7$, and R$^8$ are each independently hydrogen, halogen, —CN, C$_1$-C$_6$ alkyl, C$_1$-C$_6$ deuteroalkyl, C$_1$-C$_6$ fluoroalkyl, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$;

R$^6$ is hydrogen, halogen, —CN, C$_1$-C$_6$ alkyl, C$_1$-C$_6$ deuteroalkyl, C$_1$-C$_6$ fluoroalkyl, —OR$^{16}$, —C(=O)R$^{16}$, —CO$_2$R$^{16}$, —C(=O)N(R$^{16}$)$_2$, —N(R$^{16}$)$_2$, —NR$^{16}$C(=O)R$^{16}$, substituted or unsubstituted C$_3$-C$_6$ cycloalkyl, substituted or unsubstituted C$_2$-C$_6$heterocycloalkyl, substituted or unsubstituted phenyl, or substituted or unsubstituted heteroaryl; wherein if R$^6$ is substituted then it is substituted with one or more R$^{13}$;

each R$^9$, R$^{10}$, R$^{11}$, R$^{13}$, and R$^{14}$ is independently hydrogen, deuterium, halogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, substituted or unsubstituted C$_2$-C$_6$ heterocycloalkyl, —CN, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$;

R$^{15}$ is hydrogen, substituted or unsubstituted alkyl, substituted or unsubstituted heteroalkyl, substituted or unsubstituted C$_2$-C$_{10}$ heterocycloalkyl, —C(=O)R$^{16}$, —C(=O)—OR$^{16}$, or —C(=O)N(R$^{16}$)$_2$;

each R$^{16}$ is independently hydrogen, C$_1$-C$_6$ alkyl, C$_1$-C$_6$ deuteroalkyl, C$_1$-C$_6$ fluoroalkyl, substituted or unsubstituted C$_3$-C$_6$ cycloalkyl, substituted or unsubstituted C$_2$-C$_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted C$_3$-C$_6$cycloalkyl), -alkyl-(substituted or unsubstituted C$_2$-C$_6$ heterocycloalkyl);

or both R$^{16}$ are taken together with the N atom to which they are attached to form a substituted or unsubstituted C$_2$-C$_6$ heterocycloalkyl;

each R$^{17}$ is independently hydrogen or C$_1$-C$_6$ alkyl;

m is 1 or 2;

n is 0, 1, 2, 3, or 4;

p is 1, 2, 3, 4, or 5; and q is 1, 2, 3, 4, or 5.

In some embodiments:

R¹ is

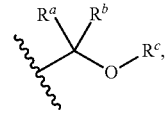

—C(O)NR$^d$R$^e$, or substituted or unsubstituted monocyclic heterocycle; wherein if R¹ is a substituted monocyclic heterocycle, then it is substituted with one or more instances of R$^9$;

R$^a$ and R$^b$ are taken together with the carbon atom to which they are attached to form a carbonyl (C=O); and R$^c$ is C$_3$-C$_6$ alkyl or R$^g$;

R$^d$ is —CN, C$_1$-C$_6$ alkyl, C$_1$-C$_6$ fluoroalkyl, —OH, —OR$^{1d}$, or —SO$_2$R$^{1d}$; and R$^e$ is hydrogen or —CH$_3$.

In some embodiments, R$^6$ is a substituted or unsubstituted heteroaryl phenyl. In some embodiments, R$^6$ is a substituted or unsubstituted heteroaryl. In some embodiments, $R^6$ is a substituted or unsubstituted pyridinyl, substituted or unsubstituted pyrazinyl, substituted or unsubstituted pyridazinyl, or substituted or unsubstituted pyrimidinyl. In some embodiments, $R^6$ is a substituted or unsubstituted pyridone or a substituted or unsubstituted pyrimidone. In some embodiments, $R^6$ is unsubstituted. In some embodiments, $R^6$ is substituted with one or more $R^{13}$.

In some embodiments, $R^6$ is substituted or unsubstituted phenyl, or substituted or unsubstituted heteroaryl, wherein if $R^6$ is substituted then it is substituted with one or more $R^{13}$.

In some embodiments:
$R^6$ is substituted or unsubstituted phenyl, substituted or unsubstituted pyridinyl, substituted or unsubstituted pyrimidinyl; wherein if $R^6$ is substituted then it is substituted with one or more $R^3$;
Z is N or $CR^8$;
$R^4$, $R^5$, $R^7$, $R^8$, $R^9$, $R^{10}$, and $R^{13}$ are each independently hydrogen, halogen, —CN, $C_1$-$C_6$ alkyl, $C_1$-$C_6$ fluoroalkyl, or $OR^{16}$.

In some embodiments:
Z is $CR^8$;
$R^4$, $R^5$, $R^7$, and $R^8$ are hydrogen;
$R^6$ is substituted phenyl; and
$R^{13}$ is halogen, —CN, $C_1$-$C_6$ alkyl, $C_1$-$C_6$ fluoroalkyl, or $OCH_3$.

In some embodiments, $R^1$ is —C(O)$OR^c$ or —C(O)$NR^dR^e$. In some embodiments, $R^1$ is —N($R^f$)$_2$. In some embodiments, $R^1$ is substituted or unsubstituted monocyclic heterocycle. In some embodiments, $R^1$ is —C(O)OH. In some embodiments, $R^1$ is —C(O)$OCH_3$ or —C(O)$OCH_2CH_3$. In some embodiments, $R^1$ is —C(O)$OR^c$. In some embodiments, $R^1$ is —C(O)O($C_1$-$C_6$ haloalkyl), —C(O)O($C_3$-$C_6$ alkyl), —C(O)O($C_3$-$C_6$ cycloalkyl), or —C(O)O($C_6$ aryl). In some embodiments, $R^1$ is —C(O)O(4- to 6-membered heterocycloalkyl) or —C(O)O(5- to 6-membered heteroaryl).

In some embodiments, $R^1$ is —C(O)$NH_2$. In some embodiments, $R^1$ is —C(O)$NR^dR^e$. In some embodiments, $R^1$ is —CN. In some embodiments, $R^1$ is —C(O)NHCN. In some embodiments, $R^1$ is —C(O)$NHCH_3$. In some embodiments, $R^1$ is —C(O)$N(CH_3)_2$. In some embodiments, $R^1$ is —C(O)NHOH, —C(O)$NHOCH_3$, —C(O)$N(CH_3)OH$, or —C(O)$N(CH_3)OCH_3$. In some embodiments, $R^1$ is —C(O)NHOH or —C(O)$NHOCH_3$. In some embodiments, $R^1$ is —C(O)NHOH or —C(O)$N(CH_3)OH$.

In some embodiments, $R^1$ is —C(O)$NHSO_2R^{1d}$. In some embodiments, $R^{1d}$ is substituted or unsubstituted $C_1$-$C_6$ alkyl, substituted or unsubstituted $C_3$-$C_6$ cycloalkyl, substituted or unsubstituted 3- to 6-membered heterocycloalkyl, substituted or unsubstituted phenyl, or substituted or unsubstituted 5- to 6-membered heteroaryl; wherein if $R^{1d}$ is substituted then it is substituted with one or more $R^{14}$. In some embodiments, $R^{1d}$ is substituted or unsubstituted $C_1$-$C_6$ alkyl. In some embodiments, $R^{1d}$ is substituted or unsubstituted methyl, wherein if $R^{1d}$ is substituted, then it is substituted with one, two, or three $R^{14}$. In some embodiments, $R^{14}$ is fluorine. In some embodiments, $R^{14}$ is —$C_1$-$C_6$ alkyl. In some embodiments, $R^{14}$ is —$OCH_3$. In some embodiments, $R^{1d}$ is —$CH_3$, —$CH_2CH_3$, —$CH_2CF_3$, —$CH_2OCH_3$, —$CH_2F$, —$CHF_2$, —$CH(CH_3)_2$, —$CHF_2$, —$C(CH_3)_3$, or —$CF_3$. In some embodiments, $R^1$ is —C(O)$NHSO_2CH_3$, —C(O)$NHSO_2CH_2CH_3$, —C(O)$NHSO_2CH_2CF_3$, —C(O)$NHSO_2CH_2OCH_3$, —C(O)$NHSO_2CH_2F$, —C(O)$NHSO_2CH(CH_3)_2$, —C(O)$NHSO_2CHF_2$, —C(O)$NHSO_2C(CH_3)_3$, or —C(O)$NHSO_2CF_3$. In some embodiments, $R^1$ is —C(O)$NHSO_2$($C_1$-$C_6$ alkyl). In some embodiments, $R^1$ is —C(O)$NHSO_2$(substituted or unsubstituted methyl).

In some embodiments, $R^{1d}$ is substituted or unsubstituted $C_3$-$C_6$ cycloalkyl. In some embodiments, $R^{1d}$ is substituted or unsubstituted cyclopropyl, substituted or unsubstituted cyclobutyl, substituted or unsubstituted cyclopentyl, or substituted or unsubstituted cyclohexyl. In some embodiments, $R^{1d}$ is substituted or unsubstituted cyclopropyl. In some embodiments, $R^1$ is —C(O)$NHSO_2$($C_3$-$C_6$ cycloalkyl). In some embodiments, $R^1$ is —C(O)$NHSO_2$(3- to 6-membered heterocycloalkyl). In some embodiments, $R^{1d}$ is oxetanyl, azetidinyl, tetrahydrofuranyl, or pyrrolidinyl. In some embodiments, $R^1$ is —C(O)$NHSO_2$(oxetanyl). In some embodiments, $R^{1d}$ is substituted or unsubstituted phenyl. In some embodiments, $R^1$ is —C(O)$NHSO_2$(phenyl). In some embodiments, $R^{1d}$ is substituted or unsubstituted 5- or 6-membered heteroaryl. In some embodiments, $R^{1d}$ is substituted or unsubstituted piperidinyl, or substituted or unsubstituted pyrimidinyl. In some embodiments, $R^1$ is —C(O)$NHSO_2$(phenyl).

In some embodiments, the compound has the structure of Formula XXI:

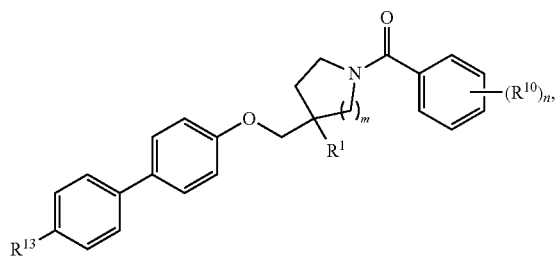

Formula XXI or a pharmaceutically acceptable salt thereof; wherein:
$R^1$ is —C(O)$OR^c$ or —C(O)$NR^dR^e$;
$R^c$ is $C_3$-$C_6$ alkyl or $R^g$;
$R^d$ is —CN, $C_1$-$C_6$ alkyl, $C_1$-$C_6$ fluoroalkyl, —OH, —$OR^{1d}$, or —$SO_2R^{1d}$;
$R^{1d}$ is substituted or unsubstituted $C_1$-$C_6$ alkyl, substituted or unsubstituted $C_3$-$C_6$ cycloalkyl, substituted or unsubstituted 3- to 6-membered heterocycloalkyl, or substituted or unsubstituted phenyl; wherein if $R^{1d}$ is substituted then it is substituted with one or more $R^{14}$;
$R^e$ is hydrogen or —$CH_3$;
$R^g$ is $C_1$-$C_6$ deuteroalkyl, $C_1$-$C_6$ fluoroalkyl, substituted or unsubstituted $C_1$-$C_6$ heteroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl;
$R^{10}$ is hydrogen, halogen, —CN, $C_1$-$C_6$ alkyl, $C_1$-$C_6$ fluoroalkyl, or $OR^{16}$;
$R^{13}$ is hydrogen, deuterium, halogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, —CN, —$OR^{16}$, —C(=O)$R^{16}$, —$CO_2R^{16}$, —C(=O)N($R^{16}$)$_2$, —N($R^{16}$)$_2$, or —$NR^{16}$C(=O)$R^{16}$;
$R^{14}$ is hydrogen, halogen, $C_1$-$C_6$ alkyl, —CN, or —$OR^{16}$;
each $R^{16}$ is independently hydrogen, $C_1$-$C_6$ alkyl, $C_1$-$C_6$ deuteroalkyl, $C_1$-$C_6$ fluoroalkyl, or substituted or unsubstituted $C_3$-$C_6$ cycloalkyl;
m is 1 or 2; and
n is 0, 1, 2, 3, or 4.

In some embodiments, the compound of Formula (XX) has the following structure of Formula (XXI'):

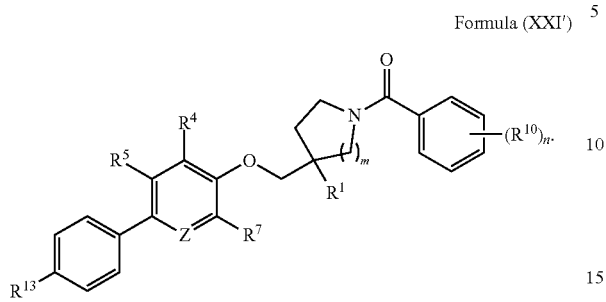

Formula (XXI')

or a pharmaceutically acceptable salt, or solvate thereof.

In some embodiments, the compound of Formula (XX) has the following structure of Formula (XXI"):

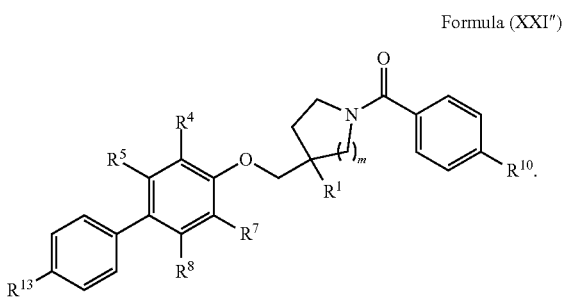

Formula (XXI")

or a pharmaceutically acceptable salt, or solvate thereof.

In some embodiments, the compound of Formula (XX) has the following structure of Formula (XXI'''):

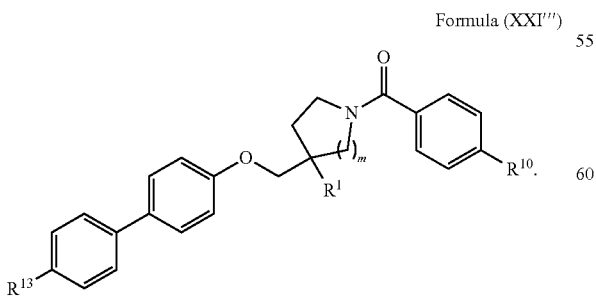

Formula (XXI''')

or a pharmaceutically acceptable salt, or solvate thereof.

In some embodiments, the compound has the structure of Formula XXII:

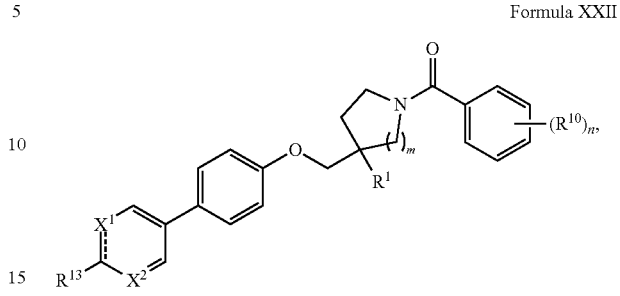

Formula XXII or a pharmaceutically acceptable salt thereof;

wherein $X^1$ and $X^2$ are each independently $CR^{13}$ or N.

In some embodiments:

$R^{10}$, $R^{13}$, and $R^{14}$ are each independently hydrogen, halogen, —CN, $C_1$-$C_6$ alkyl, $C_1$-$C_6$ fluoroalkyl, or $OR^{16}$; and $R^{16}$ is hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl.

In some embodiments: $R^1$ is —CN, —C(O)NHCH$_3$, —C(O)NHCH$_2$CF$_3$, —C(O)NHCN, —C(O)NHOH, —C(O)N(CH$_3$)OH, —C(O)NHOCH$_3$, —C(O)NHS(O)$_2$CH$_3$, —C(O)NHS(O)$_2$CF$_3$, —C(O)NHS(O)$_2$CH$_2$CH$_3$, —C(O)NHS(O)$_2$CH$_2$CF$_3$, —C(O)NHS(O)$_2$CH$_2$OCH$_3$, —C(O)NHS(O)$_2$—CH(CH$_3$)$_2$, —C(O)NHS(O)$_2$C(CH$_3$)$_2$, —C(O)NHS(O)$_2$cyclopropyl, or —C(O)NHS(O)$_2$phenyl.

In some embodiments, $R^{10}$ is —CN, —F, or —OCH$_3$; $R^{13}$ is —CN, —F, or —OCH$_3$; and n is 1.

In some embodiments, the compound has one of the following structures:

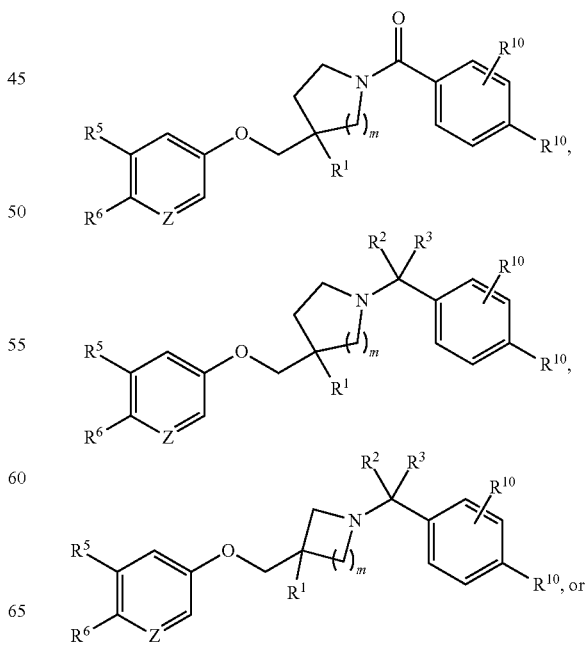

75
-continued

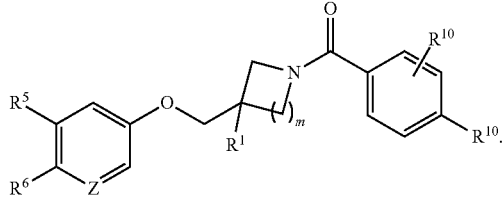

In some embodiments, the compound has one of the following structures:

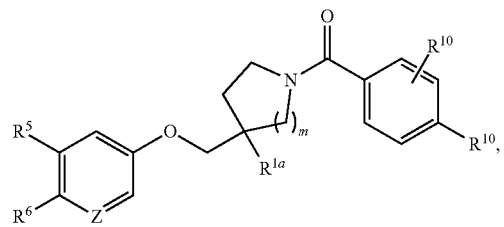

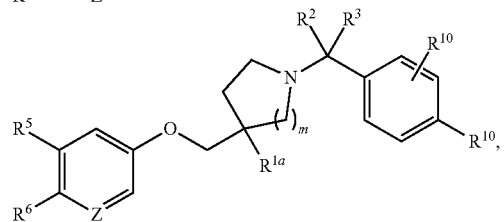

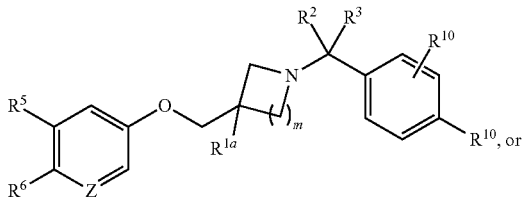

76
-continued

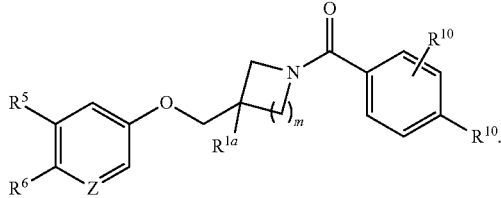

In some embodiments, $R^5$ is hydrogen; $R^6$ is substituted or unsubstituted $C_3$-$C_6$ cycloalkyl, substituted or unsubstituted $C_2$-$C_6$ heterocycloalkyl, substituted or unsubstituted phenyl, or substituted or unsubstituted heteroaryl, wherein if $R^6$ is substituted then it is substituted with one or more $R^{13}$; or $R^5$ and $R^6$ are taken together, with the intervening atoms to which they are attached, to form a fused substituted or unsubstituted ring D that is a fused substituted or unsubstituted phenyl, a fused substituted or unsubstituted pyridinyl, or a fused substituted or unsubstituted cyclohexyl, wherein if ring D is substituted then it is substituted with one or more $R^{14}$. In some embodiments, $R^5$ is hydrogen; $R^6$ is substituted or unsubstituted phenyl, or substituted or unsubstituted 6-membered heteroaryl containing 1 or 2 N atoms, wherein if $R^6$ is substituted then it is substituted with one or more $R^{13}$; or $R^5$ and $R^6$ are taken together, with the intervening atoms to which they are attached, to form a fused substituted or unsubstituted ring D that is a fused substituted or unsubstituted phenyl, or a fused substituted or unsubstituted pyridinyl, wherein if ring D is substituted then it is substituted with one or more $R^{14}$.

Any combination of the groups described above for the various variables is contemplated herein. Throughout the specification, groups and substituents thereof are chosen by one skilled in the field to provide stable moieties and compounds.

Exemplary compounds include the following compounds in Tables 1, 2, 3, and 4:

TABLE 1

| Compound no. | Structure | Name |
| --- | --- | --- |
| 1-1 | 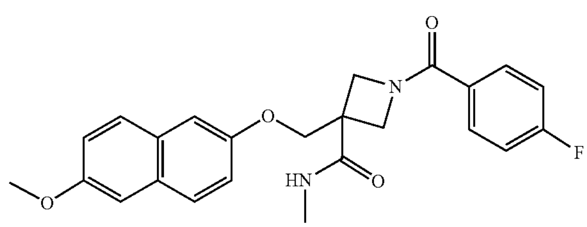 [SMILES: CNC(=O)C1(COc2ccc3cc(OC)ccc3c2)CN(C(=O)c2ccc(F)cc2)C1] | 1-(4-fluorobenzoyl)-3-(((6-methoxynaphthalen-2-yl)oxy)methyl)-N-methylazetidine-3-carboxamide |
| 1-2 | 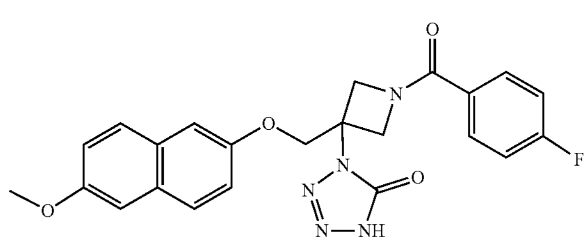 [SMILES: COc1ccc2cc(OCC3(n4nn[nH]c4=O)CN(C(=O)c4ccc(F)cc4)C3)ccc2c1] | 1-(1-(4-fluorobenzoyl)-3-(((6-methoxynaphthalen-2-yl)oxy)methyl)azetidin-3-yl)-1,4-dihydro-5H-tetrazol-5-one |

TABLE 1-continued

| Compound no. | Structure | Name |
|---|---|---|
| 1-3 | 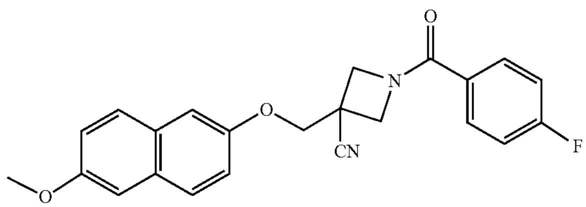 [SMILES: COc1ccc2cc(OCC3(C#N)CN(C(=O)c4ccc(F)cc4)C3)ccc2c1] | 1-(4-fluorobenzoyl)-3-(((6-methoxynaphthalen-2-yl)oxy)methyl)azetidine-3-carbonitrile |

In some embodiments, provided herein is a pharmaceutically acceptable salt of a compound that is described in Table 1.

TABLE 2

| Compound no. | Structure | Name |
|---|---|---|
| 2-1 | 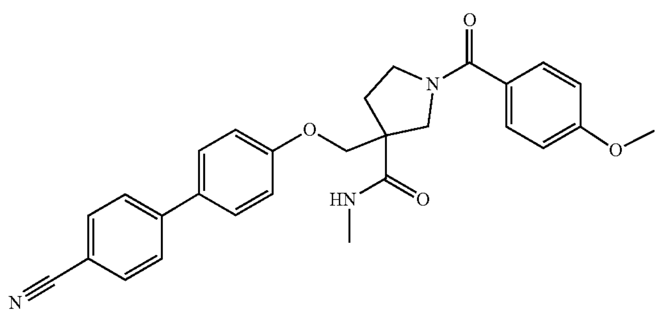 [SMILES: CNC(=O)C1(COc2ccc(-c3ccc(C#N)cc3)cc2)CCN(C(=O)c2ccc(OC)cc2)C1] | 3-(((4'-cyano-[1,1'-biphenyl]-4-yl)oxy)methyl)-1-(4-methoxybenzoyl)-N-methylpyrrolidine-3-carboxamide |
| 2-2 | 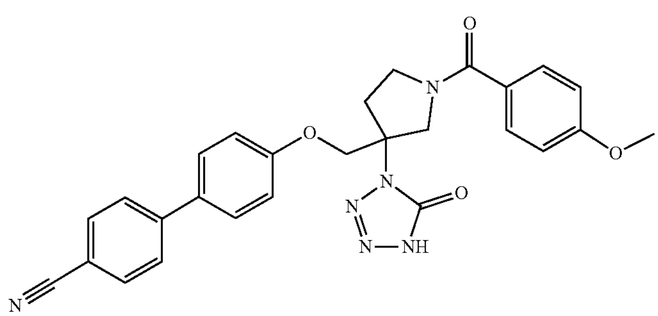 [SMILES: COc1ccc(C(=O)N2CCC(COc3ccc(-c4ccc(C#N)cc4)cc3)(n3nn[nH]c3=O)C2)cc1] | 4'-((1-(4-methoxybenzoyl)-3-(5-oxo-4,5-dihydro-1H-tetrazol-1-yl)pyrrolidin-3-yl)methoxy)-[1,1'-biphenyl]-4-carbonitrile |
| 2-3 | 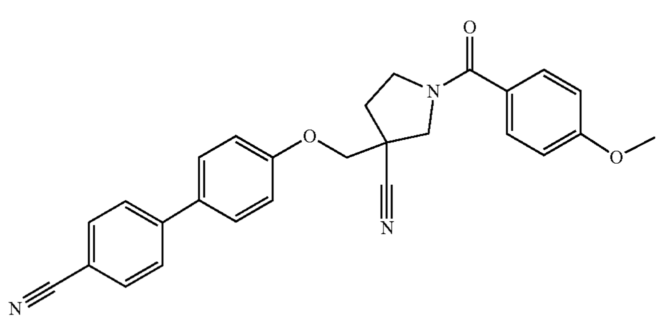 [SMILES: COc1ccc(C(=O)N2CCC(C#N)(COc3ccc(-c4ccc(C#N)cc4)cc3)C2)cc1] | 3-(((4'-cyano-[1,1'-biphenyl]-4-yl)oxy)methyl)-1-(4-methoxybenzoyl)pyrrolidine-3-carbonitrile |

TABLE 2-continued

| Compound no. | Structure | Name |
|---|---|---|
| 2-4 | 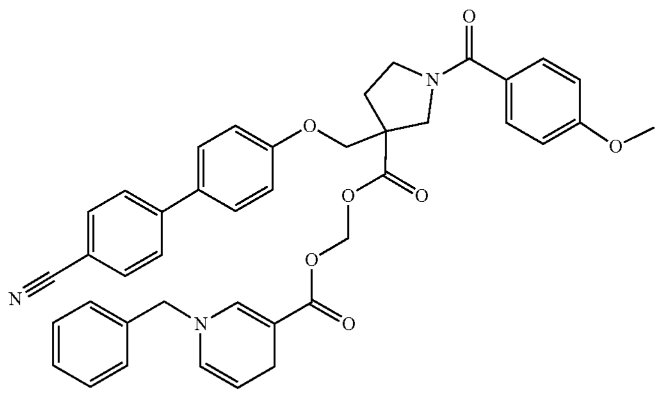 [SMILES: COc1ccc(C(=O)N2CCC(COc3ccc(-c4ccc(C#N)cc4)cc3)(C(=O)OCOC(=O)C3=CN(Cc4ccccc4)C=CC3)C2)cc1] | ((3-(((4'-cyano-[1,1'-biphenyl]-4-yl)oxy)methyl)-1-(4-methoxybenzoyl)pyrrolidine-3-carbonyl)oxy)methyl 1-benzyl-1,4-dihydropyridine-3-carboxylate |

In some embodiments, provided herein is a pharmaceutically acceptable salt of a compound that is described in Table 2.

TABLE 3

| Compound no. | Structure | Name |
|---|---|---|
| 3-1 | 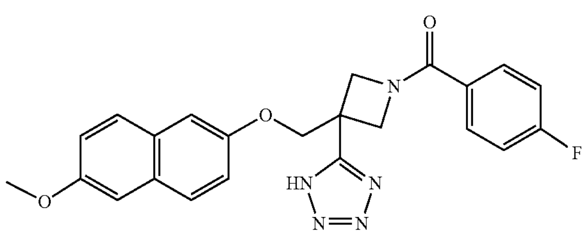 [SMILES: COc1ccc2cc(OCC3(c4nnn[nH]4)CN(C(=O)c4ccc(F)cc4)C3)ccc2c1] | (4-fluorophenyl)(3-(((6-methoxynaphthalen-2-yl)oxy)methyl)-3-(1H-tetrazol-5-yl)azetidin-1-yl)methanone |
| 3-2 | 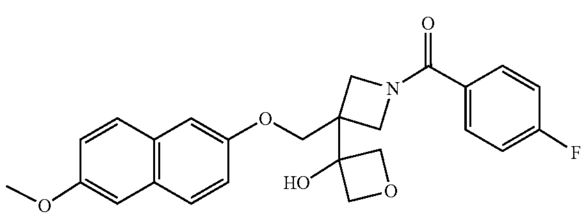 [SMILES: COc1ccc2cc(OCC3(C4(O)COC4)CN(C(=O)c4ccc(F)cc4)C3)ccc2c1] | (4-fluorophenyl)(3-(3-hydroxyoxetan-3-yl)-3-(((6-methoxynaphthalen-2-yl)oxy)methyl)azetidin-1-yl)methanone |
| 3-3 | 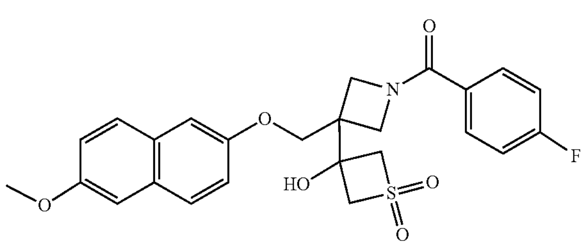 [SMILES: COc1ccc2cc(OCC3(C4(O)CS(=O)(=O)C4)CN(C(=O)c4ccc(F)cc4)C3)ccc2c1] | (4-fluorophenyl)(3-(3-hydroxy-1,1-dioxidothietan-3-yl)-3-(((6-methoxynaphthalen-2-yl)oxy)methyl)azetidin-1-yl)methanone |
| 3-4 | 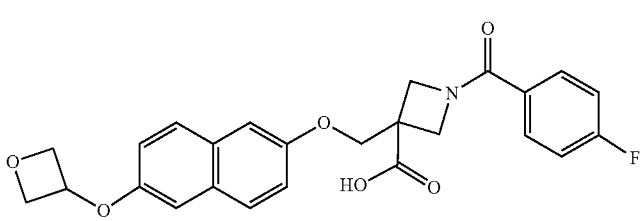 [SMILES: O=C(c1ccc(F)cc1)N1CC(COc2ccc3cc(OC4COC4)ccc3c2)(C(=O)O)C1] | 1-(4-fluorobenzoyl)-3-(((6-(oxetan-3-yloxy)naphthalen-2-yl)oxy)methyl)azetidine-3-carboxylic acid |

TABLE 3-continued

| Compound no. | Structure | Name |
|---|---|---|
| 3-5 | 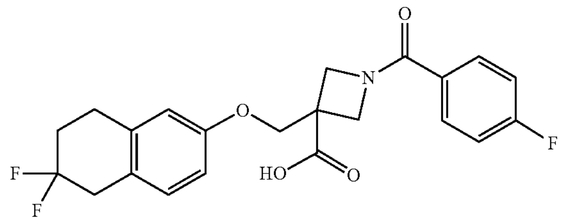 [SMILES: O=C(c1ccc(F)cc1)N1CC(COc2ccc3c(c2)CCC(F)(F)C3)(C(=O)O)C1] | 3-(((6,6-difluoro-5,6,7,8-tetrahydronaphthalen-2-yl)oxy)methyl)-1-(4-fluorobenzoyl)azetidine-3-carboxylic acid |
| 3-6 | 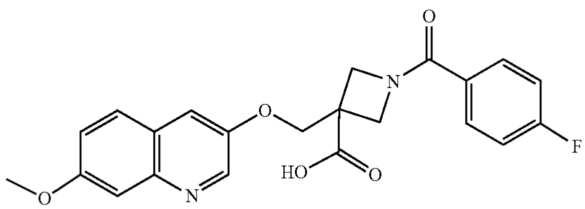 [SMILES: COc1ccc2cc(OCC3(C(=O)O)CN(C(=O)c4ccc(F)cc4)C3)cnc2c1] | 1-(4-fluorobenzoyl)-3-(((7-methoxyquinolin-3-yl)oxy)methyl)azetidine-3-carboxylic acid |
| 3-7 | 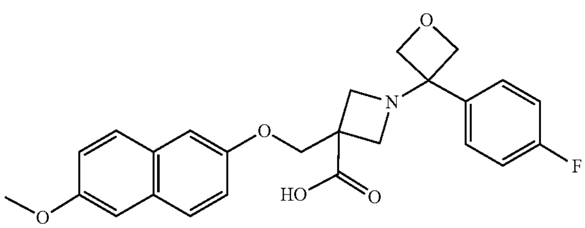 [SMILES: COc1ccc2cc(OCC3(C(=O)O)CN(C4(c5ccc(F)cc5)COC4)C3)ccc2c1] | 1-(3-(4-fluorophenyl)oxetan-3-yl)-3-(((6-methoxynaphthalen-2-yl)oxy)methyl)azetidine-3-carboxylic acid |
| 3-8 | 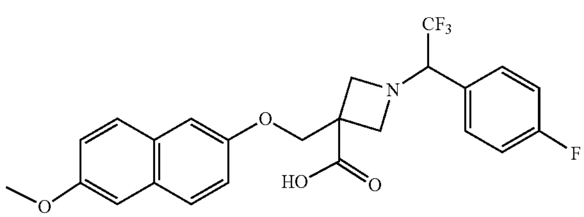 [SMILES: COc1ccc2cc(OCC3(C(=O)O)CN(C(c4ccc(F)cc4)C(F)(F)F)C3)ccc2c1] | 3-(((6-methoxynaphthalen-2-yl)oxy)methyl)-1-(2,2,2-trifluoro-1-(4-fluorophenyl)ethyl)azetidine-3-carboxylic acid |
| 3-9 | 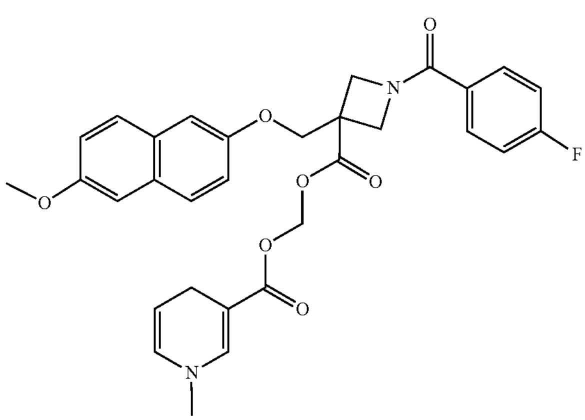 [SMILES: COc1ccc2cc(OCC3(C(=O)OCOC(=O)C4=CN(C)C=CC4)CN(C(=O)c4ccc(F)cc4)C3)ccc2c1] | ((1-(4-fluorobenzoyl)-3-(((6-methoxynaphthalen-2-yl)oxy)methyl)azetidine-3-carbonyl)oxy)methyl 1-methyl-1,4-dihydropyridine-3-carboxylate |

TABLE 3-continued

| Compound no. | Structure | Name |
|---|---|---|
| 3-10 | 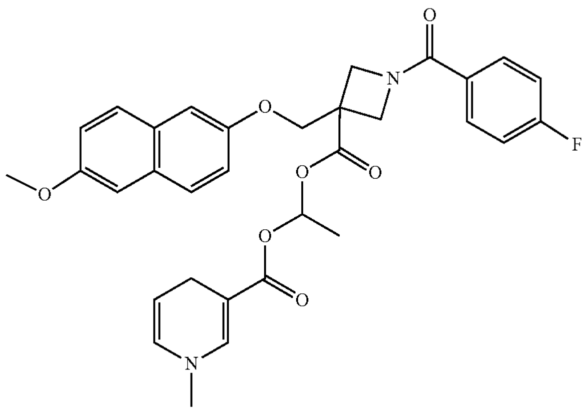 [SMILES: COc1ccc2cc(OCC3(C(=O)OC(C)OC(=O)C4=CN(C)C=CC4)CN(C(=O)c4ccc(F)cc4)C3)ccc2c1] | 1-((1-(4-fluorobenzoyl)-3-(((6-methoxynaphthalen-2-yl)oxy)methyl)azetidine-3-carbonyl)oxy)ethyl 1-methyl-1,4-dihydropyridine-3-carboxylate |
| 3-11 | 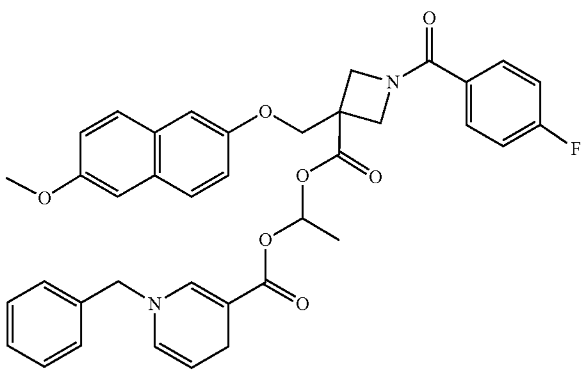 [SMILES: COc1ccc2cc(OCC3(C(=O)OC(C)OC(=O)C4=CN(Cc5ccccc5)C=CC4)CN(C(=O)c4ccc(F)cc4)C3)ccc2c1] | 1-((1-(4-fluorobenzoyl)-3-(((6-methoxynaphthalen-2-yl)oxy)methyl)azetidine-3-carbonyl)oxy)ethyl 1-benzyl-1,4-dihydropyridine-3-carboxylate |
| 3-12 | 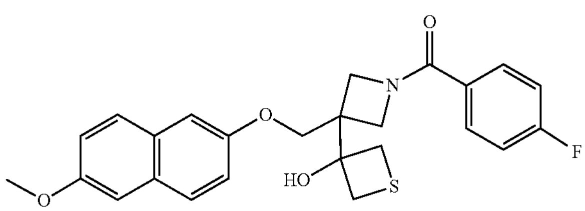 [SMILES: COc1ccc2cc(OCC3(C4(O)CSC4)CN(C(=O)c4ccc(F)cc4)C3)ccc2c1] | (4-fluorophenyl)(3-(3-hydroxythietan-3-yl)-3-(((6-methoxynaphthalen-2-yl)oxy)methyl)azetidin-1-yl)methanone |
| 3-13 | 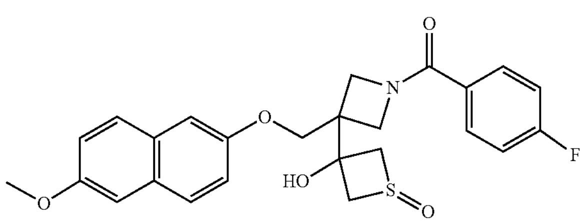 [SMILES: COc1ccc2cc(OCC3(C4(O)CS(=O)C4)CN(C(=O)c4ccc(F)cc4)C3)ccc2c1] | (4-fluorophenyl)(3-(3-hydroxy-1-oxidothietan-3-yl)-3-(((6-methoxynaphthalen-2-yl)oxy)methyl)azetidin-1-yl)methanone |
| 3-14 | 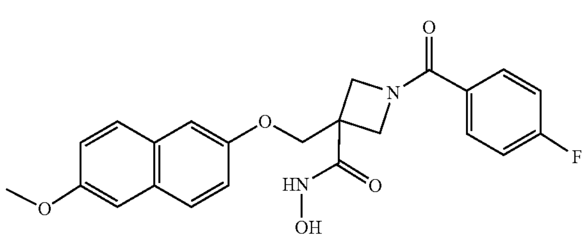 [SMILES: COc1ccc2cc(OCC3(C(=O)NO)CN(C(=O)c4ccc(F)cc4)C3)ccc2c1] | 1-(4-fluorobenzoyl)-N-hydroxy-3-(((6-methoxynaphthalen-2-yl)oxy)methyl)azetidine-3-carboxamide |

TABLE 3-continued

| Compound no. | Structure | Name |
|---|---|---|
| 3-15 | 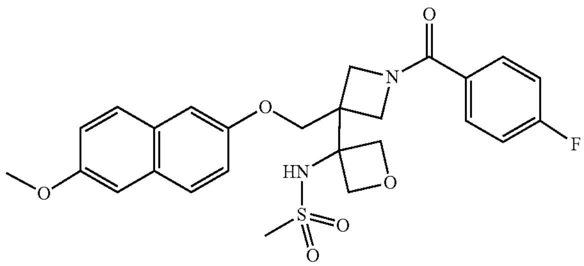 [SMILES: COc1ccc2cc(OCC3(C4(NS(C)(=O)=O)COC4)CN(C(=O)c4ccc(F)cc4)C3)ccc2c1] | N-(3-(1-(4-fluorobenzoyl)-3-((((6-methoxynaphthalen-2-yl)oxy)methyl)azetidin-3-yl)oxetan-3-yl)methanesulfonamide |
| 3-16 | 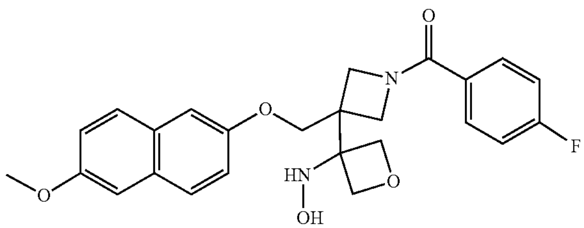 [SMILES: COc1ccc2cc(OCC3(C4(NO)COC4)CN(C(=O)c4ccc(F)cc4)C3)ccc2c1] | (4-fluorophenyl)(3-(3-(hydroxyamino)oxetan-3-yl)-3-(((6-methoxynaphthalen-2-yl)oxy)methyl)azetidin-1-yl)methanone |
| 3-17 | 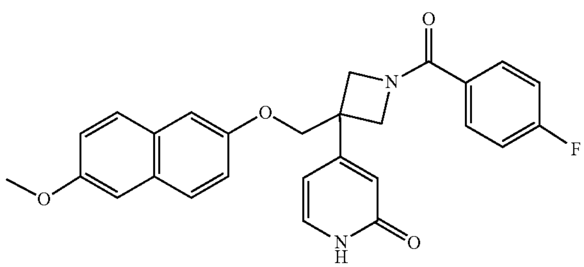 [SMILES: COc1ccc2cc(OCC3(c4cc[nH]c(=O)c4)CN(C(=O)c4ccc(F)cc4)C3)ccc2c1] | 4-(1-(4-fluorobenzoyl)-3-(((6-methoxynaphthalen-2-yl)oxy)methyl)azetidin-3-yl)pyridin-2(1H)-one |
| 3-18 | 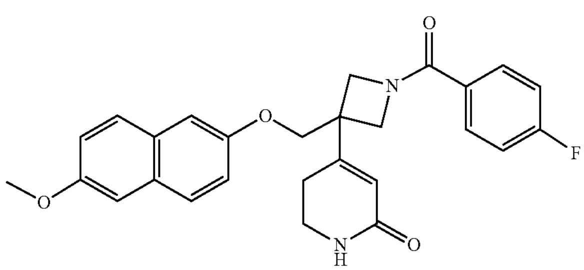 [SMILES: COc1ccc2cc(OCC3(C4=CC(=O)NCC4)CN(C(=O)c4ccc(F)cc4)C3)ccc2c1] | 4-(1-(4-fluorobenzoyl)-3-(((6-methoxynaphthalen-2-yl)oxy)methyl)azetidin-3-yl)-5,6-dihydropyridin-2(1H)-one |
| 3-19 | 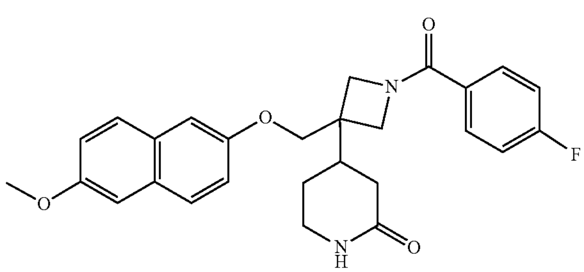 [SMILES: COc1ccc2cc(OCC3(C4CCNC(=O)C4)CN(C(=O)c4ccc(F)cc4)C3)ccc2c1] | 4-(1-(4-fluorobenzoyl)-3-(((6-methoxynaphthalen-2-yl)oxy)methyl)azetidin-3-yl)piperidin-2-one |

In some embodiments, provided herein is a pharmaceutically acceptable salt of a compound that is described in Table 3.

TABLE 4

| Compound no. | Structure | Name |
|---|---|---|
| 4-1 | 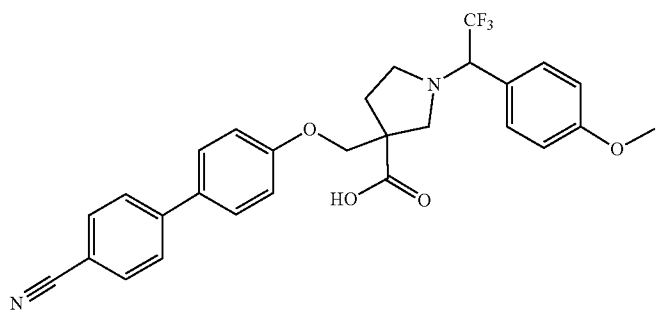 [SMILES: COc1ccc(C(N2CCC(COc3ccc(-c4ccc(C#N)cc4)cc3)(C(=O)O)C2)C(F)(F)F)cc1] | 3-(((4'-cyano-[1,1'-biphenyl]-4-yl)oxy)methyl)-1-(2,2,2-trifluoro-1-(4-methoxyphenyl)ethyl)pyrrolidine-3-carboxylic acid |
| 4-2 | 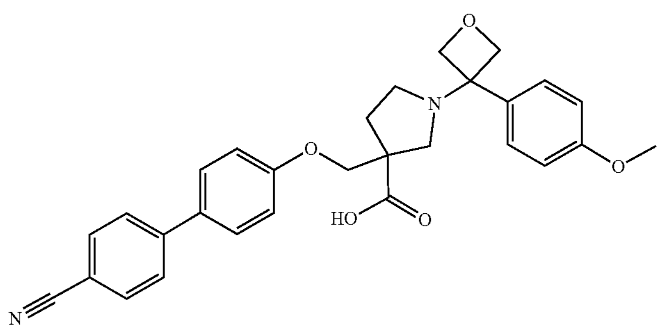 [SMILES: COc1ccc(C2(N3CCC(COc4ccc(-c5ccc(C#N)cc5)cc4)(C(=O)O)C3)COC2)cc1] | 3-(((4'-cyano-[1,1'-biphenyl]-4-yl)oxy)methyl)-1-(3-(4-methoxyphenyl)oxetan-3-yl)pyrrolidine-3-carboxylic acid |
| 4-3 | 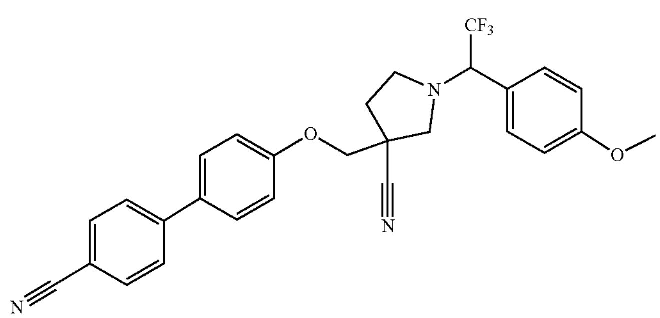 [SMILES: COc1ccc(C(N2CCC(C#N)(COc3ccc(-c4ccc(C#N)cc4)cc3)C2)C(F)(F)F)cc1] | 3-(((4'-cyano-[1,1'-biphenyl]-4-yl)oxy)methyl)-1-(2,2,2-trifluoro-1-(4-methoxyphenyl)ethyl)pyrrolidine-3-carbonitrile |
| 4-4 | 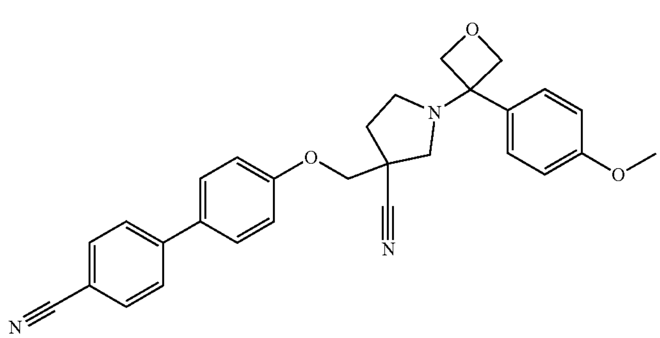 [SMILES: COc1ccc(C2(N3CCC(C#N)(COc4ccc(-c5ccc(C#N)cc5)cc4)C3)COC2)cc1] | 3-(((4'-cyano-[1,1'-biphenyl]-4-yl)oxy)methyl)-1-(3-(4-methoxyphenyl)oxetan-3-yl)pyrrolidine-3-carbonitrile |

TABLE 4-continued

| Compound no. | Structure | Name |
|---|---|---|
| 4-5 | 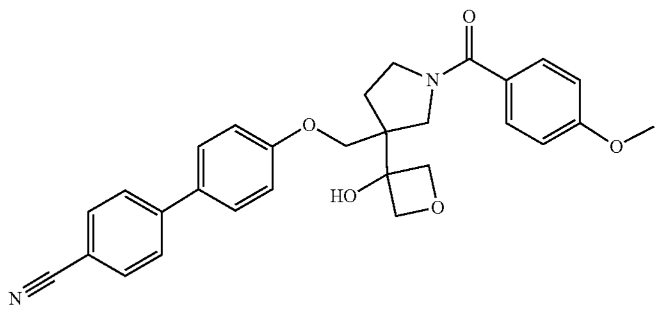 [SMILES: COc1ccc(C(=O)N2CCC(COc3ccc(-c4ccc(C#N)cc4)cc3)(C3(O)COC3)C2)cc1] | 4'-((3-(3-hydroxyoxetan-3-yl)-1-(4-methoxybenzoyl)pyrrolidin-3-yl)methoxy)-[1,1'-biphenyl]-4-carbonitrile |
| 4-6 | 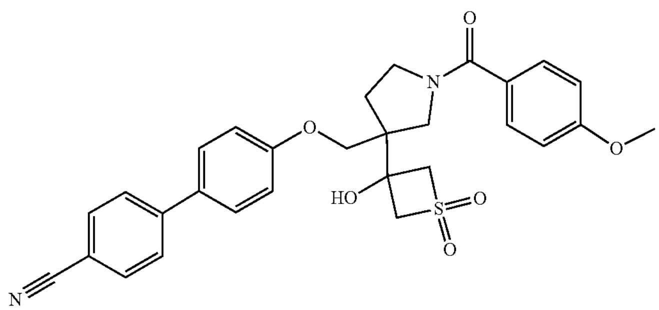 [SMILES: COc1ccc(C(=O)N2CCC(COc3ccc(-c4ccc(C#N)cc4)cc3)(C3(O)CS(=O)(=O)C3)C2)cc1] | 4'-((3-(3-hydroxy-1,1-dioxidothietan-3-yl)-1-(4-methoxybenzoyl)pyrrolidin-3-yl)methoxy)-[1,1'-biphenyl]-4-carbonitrile |
| 4-7 | 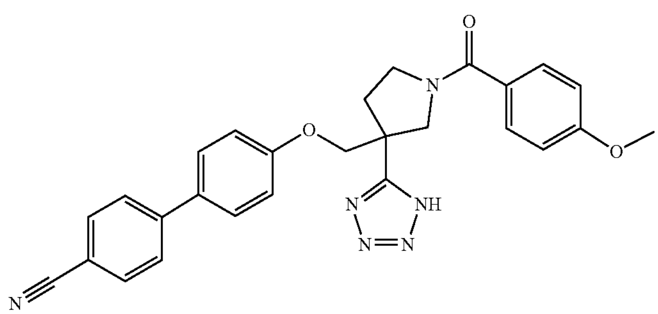 [SMILES: COc1ccc(C(=O)N2CCC(COc3ccc(-c4ccc(C#N)cc4)cc3)(c3nnn[nH]3)C2)cc1] | 4'-((1-(4-methoxybenzoyl)-3-(1H-tetrazol-5-yl)pyrrolidin-3-yl)methoxy)-[1,1'-biphenyl]-4-carbonitrile |
| 4-8 | 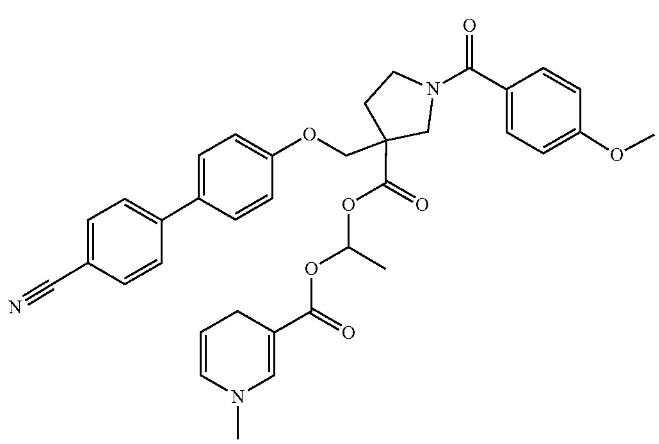 [SMILES: COc1ccc(C(=O)N2CCC(COc3ccc(-c4ccc(C#N)cc4)cc3)(C(=O)OC(C)OC(=O)C3=CN(C)C=CC3)C2)cc1] | 1-((3-(((4'-cyano-[1,1'-biphenyl]-4-yl)oxy)methyl)-1-(4-methoxybenzoyl)pyrrolidine-3-carbonyl)oxy)ethyl 1-methyl-1,4-dihydropyridine-3-carboxylate |

TABLE 4-continued

| Compound no. | Structure | Name |
|---|---|---|
| 4-9 | 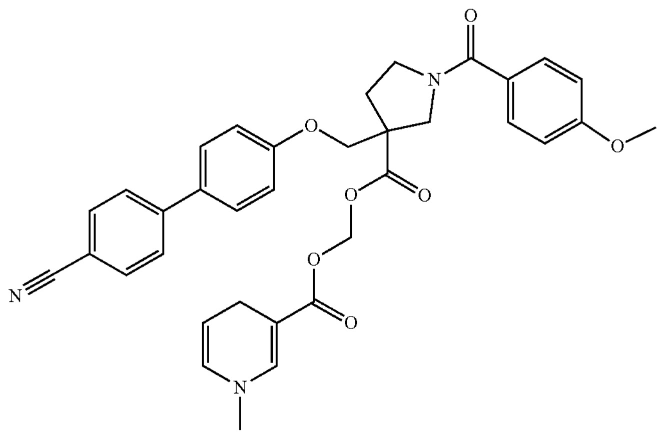 [SMILES: COc1ccc(C(=O)N2CCC(COc3ccc(-c4ccc(C#N)cc4)cc3)(C(=O)OCOC(=O)C3=CN(C)C=CC3)C2)cc1] | ((3-(((4'-cyano-[1,1'-biphenyl]-4-yl)oxy)methyl)-1-(4-methoxybenzoyl)pyrrolidine-3-carbonyl)oxy)methyl 1-methyl-1,4-dihydropyridine-3-carboxylate |
| 4-10 | 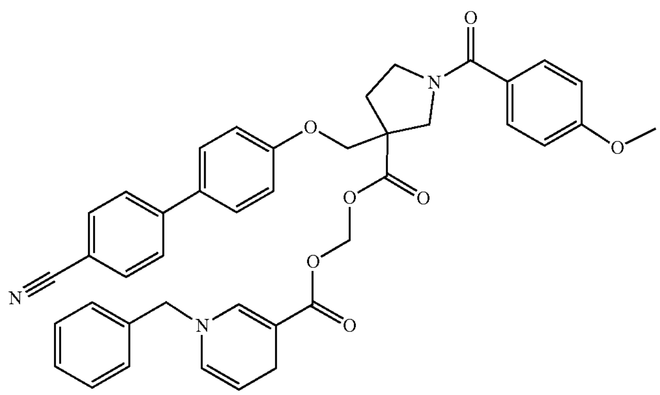 [SMILES: COc1ccc(C(=O)N2CCC(COc3ccc(-c4ccc(C#N)cc4)cc3)(C(=O)OCOC(=O)C3=CN(Cc4ccccc4)C=CC3)C2)cc1] | ((3-(((4'-cyano-[1,1'-biphenyl]-4-yl)oxy)methyl)-1-(4-methoxybenzoyl)pyrrolidine-3-carbonyl)oxy)methyl 1-benzyl-1,4-dihydropyridine-3-carboxylate |
| 4-11 | 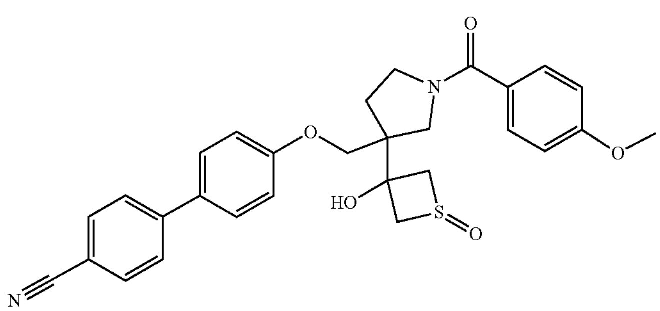 [SMILES: COc1ccc(C(=O)N2CCC(COc3ccc(-c4ccc(C#N)cc4)cc3)(C3(O)CS(=O)C3)C2)cc1] | 4'-((3-(3-hydroxy-1-oxidothietan-3-yl)-1-(4-methoxybenzoyl)pyrrolidin-3-yl)methoxy)-[1,1'-biphenyl]-4-carbonitrile |
| 4-12 | 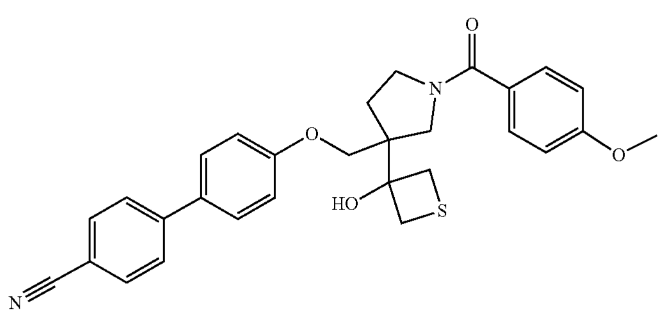 [SMILES: COc1ccc(C(=O)N2CCC(COc3ccc(-c4ccc(C#N)cc4)cc3)(C3(O)CSC3)C2)cc1] | 4'-((3-(3-hydroxythietan-3-yl)-1-(4-methoxybenzoyl)pyrrolidin-3-yl)methoxy)-[1,1'-biphenyl]-4-carbonitrile |

TABLE 4-continued

| Compound no. | Structure | Name |
|---|---|---|
| 4-13 | 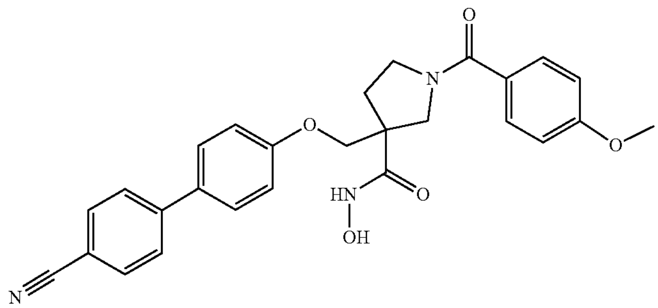 [SMILES: COc1ccc(C(=O)N2CCC(COc3ccc(-c4ccc(C#N)cc4)cc3)(C(=O)NO)C2)cc1] | 3-(((4'-cyano-[1,1'-biphenyl]-4-yl)oxy)methyl)-N-hydroxy-1-(4-methoxybenzoyl)pyrrolidine-3-carboxamide |
| 4-14 | 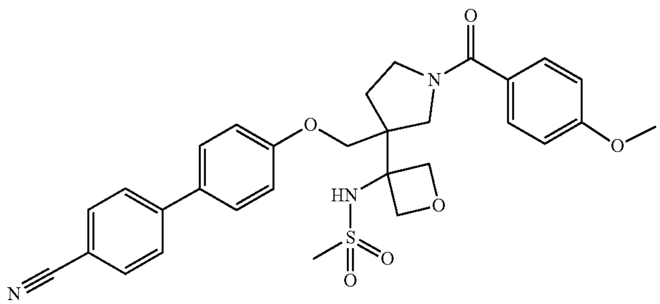 [SMILES: COc1ccc(C(=O)N2CCC(COc3ccc(-c4ccc(C#N)cc4)cc3)(C3(NS(C)(=O)=O)COC3)C2)cc1] | N-(3-(3-(((4'-cyano-[1,1'-biphenyl]-4-yl)oxy)methyl)-1-(4-methoxybenzoyl)pyrrolidin-3-yl)oxetan-3-yl)methanesulfonamide |
| 4-15 | 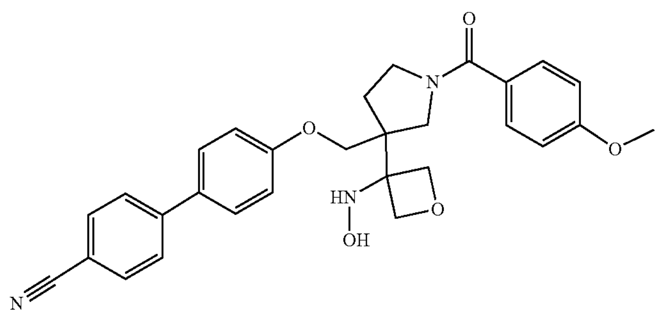 [SMILES: COc1ccc(C(=O)N2CCC(COc3ccc(-c4ccc(C#N)cc4)cc3)(C3(NO)COC3)C2)cc1] | 4'-((3-(3-(hydroxyamino)oxetan-3-yl)-1-(4-methoxybenzoyl)pyrrolidin-3-yl)methoxy)-[1,1'-biphenyl]-4-carbonitrile |
| 4-16 | 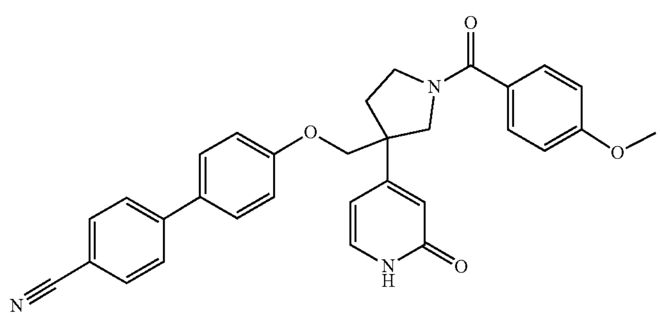 [SMILES: COc1ccc(C(=O)N2CCC(COc3ccc(-c4ccc(C#N)cc4)cc3)(c3cc[nH]c(=O)c3)C2)cc1] | 4'-((1-(4-methoxybenzoyl)-3-(2-oxo-1,2-dihydropyridin-4-yl)pyrrolidin-3-yl)methoxy)-[1,1'-biphenyl]-4-carbonitrile |
| 4-17 | 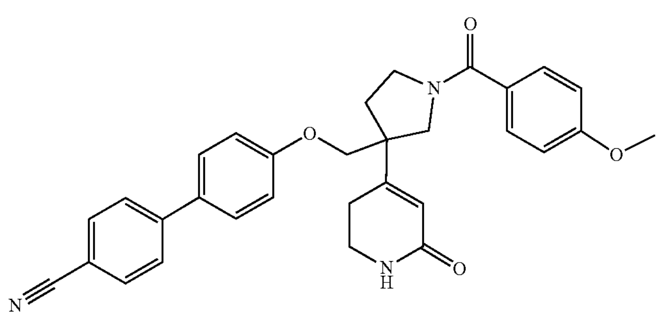 [SMILES: COc1ccc(C(=O)N2CCC(COc3ccc(-c4ccc(C#N)cc4)cc3)(C3=CC(=O)NCC3)C2)cc1] | 4'-((1-(4-methoxybenzoyl)-3-(6-oxo-1,2,3,6-tetrahydropyridin-4-yl)pyrrolidin-3-yl)methoxy)-[1,1'-biphenyl]-4-carbonitrile |

TABLE 4-continued

| Compound no. | Structure | Name |
|---|---|---|
| 4-18 | 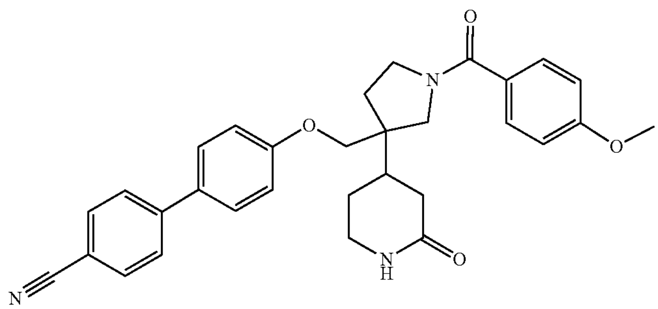 [SMILES: COc1ccc(C(=O)N2CCC(COc3ccc(-c4ccc(C#N)cc4)cc3)(C3CCNC(=O)C3)C2)cc1] | 4'-((1-(4-methoxybenzoyl)-3-(2-oxopiperidin-4-yl)pyrrolidin-3-yl)methoxy)-[1,1'-biphenyl]-4-carbonitrile |
| 4-19 | 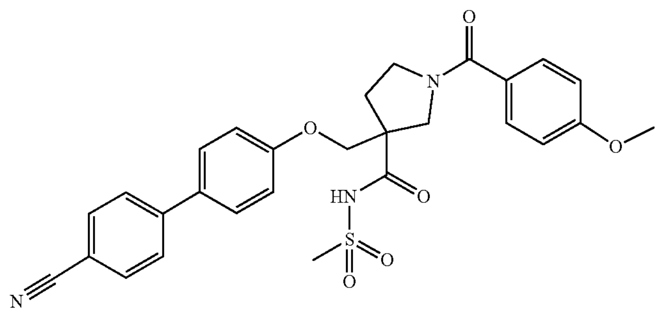 [SMILES: COc1ccc(C(=O)N2CCC(COc3ccc(-c4ccc(C#N)cc4)cc3)(C(=O)NS(C)(=O)=O)C2)cc1] | 3-(((4'-cyano-[1,1'-biphenyl]-4-yl)oxy)methyl)-1-(4-methoxybenzoyl)-N-(methylsulfonyl)pyrrolidine-3-carboxamide |
| 4-20 | 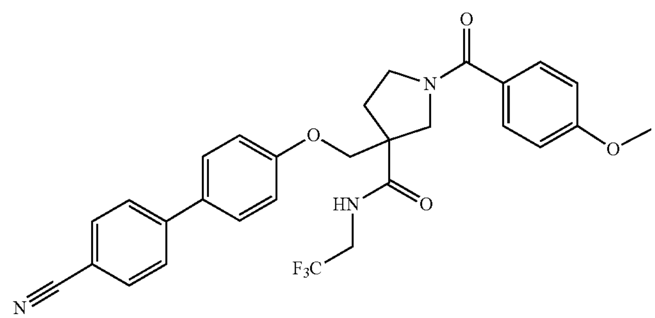 [SMILES: COc1ccc(C(=O)N2CCC(COc3ccc(-c4ccc(C#N)cc4)cc3)(C(=O)NCC(F)(F)F)C2)cc1] | 3-(((4'-cyano-[1,1'-biphenyl]-4-yl)oxy)methyl)-1-(4-methoxybenzoyl)-N-(2,2,2-trifluoroethyl)pyrrolidine-3-carboxamide |
| 4-21 | 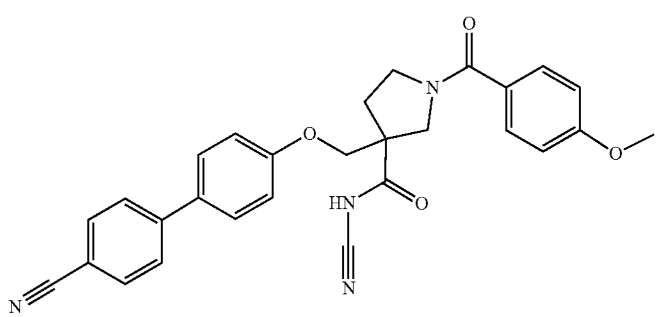 [SMILES: COc1ccc(C(=O)N2CCC(COc3ccc(-c4ccc(C#N)cc4)cc3)(C(=O)NC#N)C2)cc1] | N-cyano-3-(((4'-cyano-[1,1'-biphenyl]-4-yl)oxy)methyl)-1-(4-methoxybenzoyl)pyrrolidine-3-carboxamide |
| 4-22 | 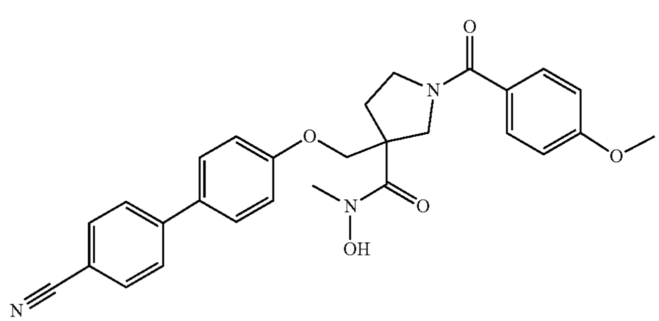 [SMILES: COc1ccc(C(=O)N2CCC(COc3ccc(-c4ccc(C#N)cc4)cc3)(C(=O)N(C)O)C2)cc1] | 3-(((4'-cyano-[1,1'-biphenyl]-4-yl)oxy)methyl)-N-hydroxy-1-(4-methoxybenzoyl)-N-methylpyrrolidine-3-carboxamide |

TABLE 4-continued

| Compound no. | Structure | Name |
|---|---|---|
| 4-23 | 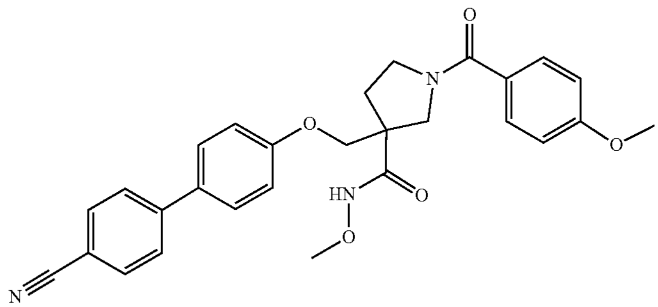 [SMILES: CONC(=O)C1(COc2ccc(-c3ccc(C#N)cc3)cc2)CCN(C(=O)c2ccc(OC)cc2)C1] | 3-(((4'-cyano-[1,1'-biphenyl]-4-yl)oxy)methyl)-N-methoxy-1-(4-methoxybenzoyl)pyrrolidine-3-carboxamide |
| 4-24 | 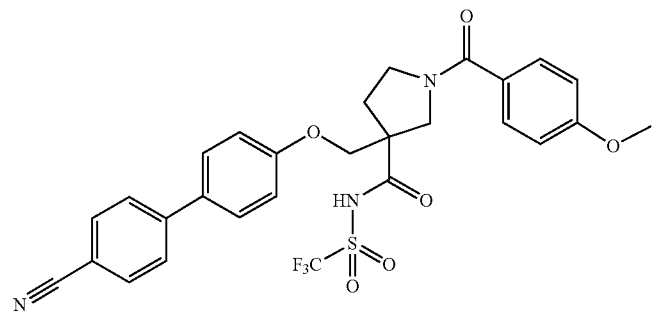 [SMILES: COc1ccc(C(=O)N2CCC(COc3ccc(-c4ccc(C#N)cc4)cc3)(C(=O)NS(=O)(=O)C(F)(F)F)C2)cc1] | 3-[({4'-cyano-[1,1'-biphenyl]-4-yl}oxy)methyl]-1-(4-methoxybenzoyl)-N-trifluoromethanesulfonylpyrrolidine-3-carboxamide |
| 4-25 | 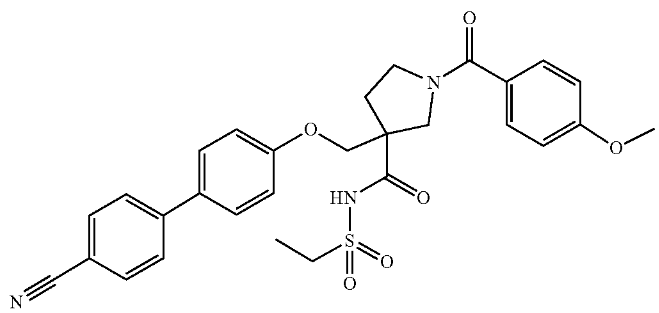 [SMILES: CCS(=O)(=O)NC(=O)C1(COc2ccc(-c3ccc(C#N)cc3)cc2)CCN(C(=O)c2ccc(OC)cc2)C1] | 3-[({4'-cyano-[1,1'-biphenyl]-4-yl}oxy)methyl]-N-(ethanesulfonyl)-1-(4-methoxybenzoyl)pyrrolidine-3-carboxamide |
| 4-26 | 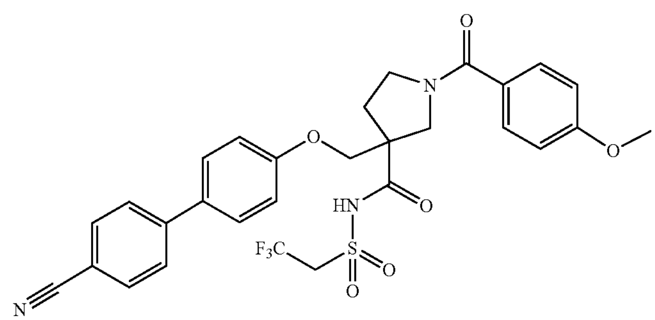 [SMILES: COc1ccc(C(=O)N2CCC(COc3ccc(-c4ccc(C#N)cc4)cc3)(C(=O)NS(=O)(=O)CC(F)(F)F)C2)cc1] | 3-[({4'-cyano-[1,1'-biphenyl]-4-yl}oxy)methyl]-1-(4-methoxybenzoyl)-N-(2,2,2-trifluoroethanesulfonyl)pyrrolidine-3-carboxamide |
| 4-27 | 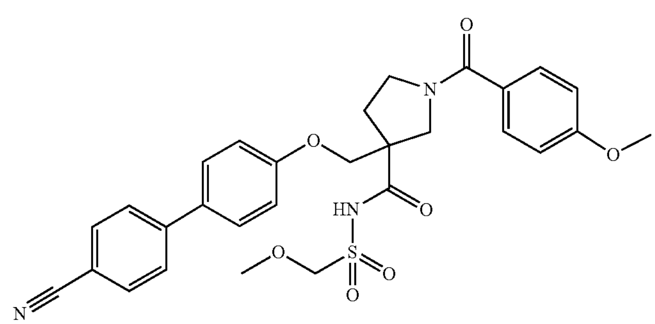 [SMILES: COCS(=O)(=O)NC(=O)C1(COc2ccc(-c3ccc(C#N)cc3)cc2)CCN(C(=O)c2ccc(OC)cc2)C1] | 3-[({4'-cyano-[1,1'-biphenyl]-4-yl}oxy)methyl]-1-(4-methoxybenzoyl)-N-methoxymethanesulfonylpyrrolidine-3-carboxamide |

TABLE 4-continued

| Compound no. | Structure | Name |
|---|---|---|
| 4-28 | 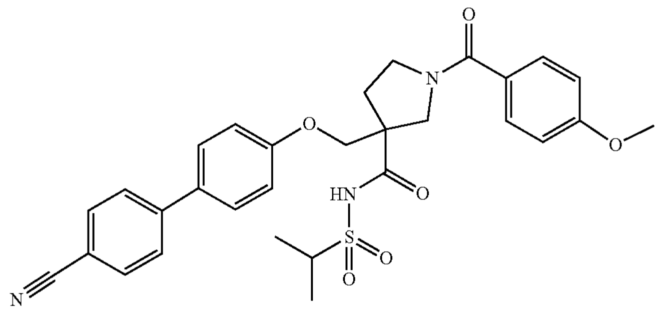 [SMILES: COc1ccc(C(=O)N2CCC(COc3ccc(-c4ccc(C#N)cc4)cc3)(C(=O)NS(=O)(=O)C(C)C)C2)cc1] | 3-[({4'-cyano-[1,1'-biphenyl]-4-yl}oxy)methyl]-1-(4-methoxybenzoyl)-N-(propane-2-sulfonyl)pyrrolidine-3-carboxamide |
| 4-29 | 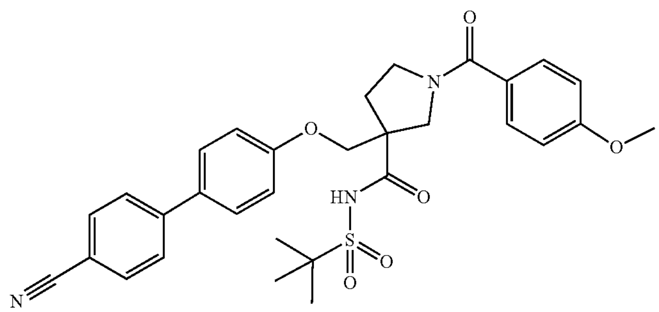 [SMILES: COc1ccc(C(=O)N2CCC(COc3ccc(-c4ccc(C#N)cc4)cc3)(C(=O)NS(=O)(=O)C(C)(C)C)C2)cc1] | 3-[({4'-cyano-[1,1'-biphenyl]-4-yl}oxy)methyl]-1-(4-methoxybenzoyl)-N-(2-methylpropane-2-sulfonyl)pyrrolidine-3-carboxamide |
| 4-30 | 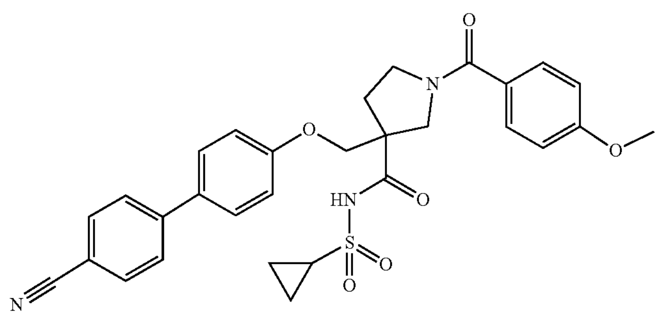 [SMILES: COc1ccc(C(=O)N2CCC(COc3ccc(-c4ccc(C#N)cc4)cc3)(C(=O)NS(=O)(=O)C3CC3)C2)cc1] | 3-[({4'-cyano-[1,1'-biphenyl]-4-yl}oxy)methyl]-N-(cyclopropanesulfonyl)-1-(4-methoxybenzoyl)pyrrolidine-3-carboxamide |
| 4-31 | 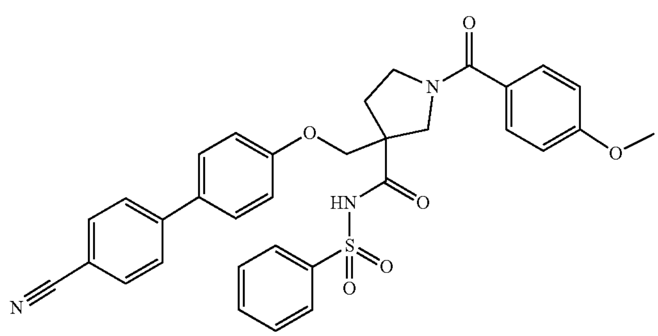 [SMILES: COc1ccc(C(=O)N2CCC(COc3ccc(-c4ccc(C#N)cc4)cc3)(C(=O)NS(=O)(=O)c3ccccc3)C2)cc1] | N-(benzenesulfonyl)-3-[({4'-cyano-[1,1'-biphenyl]-4-yl}oxy)methyl]-1-(4-methoxybenzoyl)pyrrolidine-3-carboxamide |
| 4-32 | 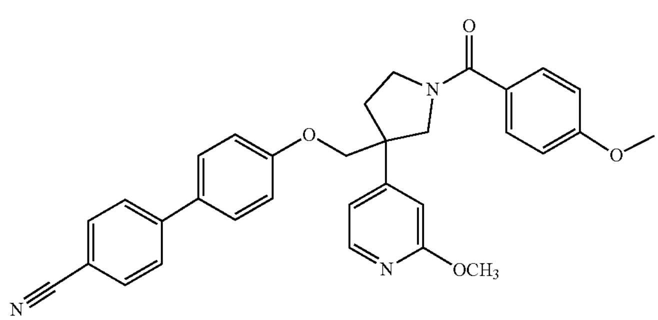 [SMILES: COc1ccc(C(=O)N2CCC(COc3ccc(-c4ccc(C#N)cc4)cc3)(c3ccnc(OC)c3)C2)cc1] | 4'-{[1-(4-methoxybenzoyl)-3-(2-methoxypyridin-4-yl)pyrrolidin-3-yl]methoxy}-[1,1'-biphenyl]-4-carbonitrile |

TABLE 4-continued

| Compound no. | Structure | Name |
|---|---|---|
| 4-33 | 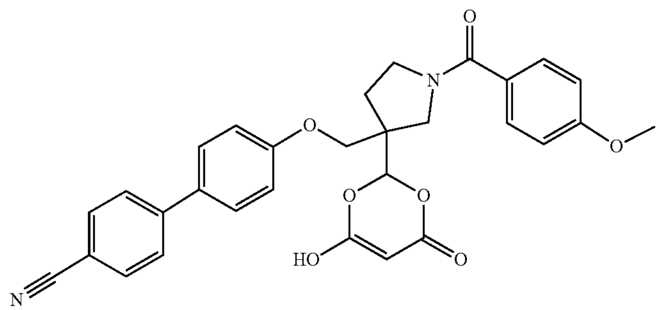 [SMILES: COc1ccc(C(=O)N2CCC(COc3ccc(-c4ccc(C#N)cc4)cc3)(C3OC(=O)C=C(O)O3)C2)cc1] | 4'-((3-(6-hydroxy-4-oxo-4H-1,3-dioxin-2-yl)-1-(4-methoxybenzoyl)pyrrolidin-3-yl)methoxy)-[1,1'-biphenyl]-4-carbonitrile |
| 4-34 | 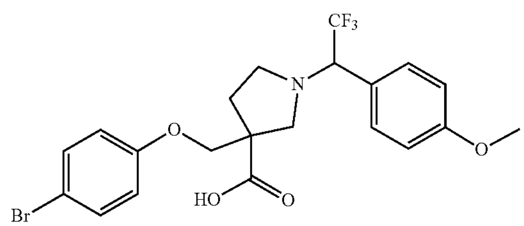 [SMILES: COc1ccc(C(N2CCC(COc3ccc(Br)cc3)(C(=O)O)C2)C(F)(F)F)cc1] | 1-[1-(4-bromophenyl)-2,2,2-trifluoroethyl]-3-[({4'-cyano-[1,1'-biphenyl]-4-yl}oxy)methyl]pyrrolidine-3-carboxylic acid |

In some embodiments, provided herein is a pharmaceutically acceptable salt of a compound that is described in Table 4.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zurich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible, and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. In some instances, a prodrug may pass through membranes (e.g., cell membranes, the intestinal lumen, the blood brain barrier, and the like) whereas the active agent would not. In some instances, a charged or highly polar moiety is masked with a more permeable group which can be cleaved in vivo. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. In some embodiments, the prodrug is enzymatically metabolized to the active form in vivo via an esterase, protease, peptidase, hydrolase, etc. In some embodiments, the prodrug transforms into the active form of the compound independent of a metabolizing enzyme (e.g., via hydrolysis or pH-dependent decomposition).

Prodrugs of the compounds described herein include, but are not limited to, esters, ethers (e.g., oxymethyl ethers), carbonates, thiocarbonates, carbamates, anhydrides, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A.

Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a carboxyl group is used to provide an ester or amide (i.e., the prodrug), which is then metabolized in vivo to provide a carboxylic acid group. In some embodiments, compounds described herein are prepared as alkyl ester prodrugs. In some embodiments, compounds described herein are prepared as oxymethyl ether or polyoxymethylene dimethyl ether prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

In some embodiments, compounds of the present disclosure provide enhanced pharmacokinetic or pharmacodynamic profiles compared to other known EP2 antagonists. For example, a compound described herein may increase the bioavailability, volume of distribution, absorption, half-life, duration of action, receptor occupancy, cellular permeability, blood-brain barrier permeability, plasma stability, metabolic stability, excretion, or toxicity profile compared to the EP2 antagonists currently available. In some embodiments, a compound is formulated as a prodrug, wherein the active metabolite is cleaved in vivo after reaching the target cell or tissue. In other embodiments, a compound is not cleaved in vivo.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)═CR$_2$, wherein R refers to the remaining portions of the alkenyl group, which may be the same or different. In some embodiments, R is H or an alkyl. Non-limiting examples of an alkenyl group include —CH═CH$_2$, —C(CH$_3$)═CH$_2$, —CH═CHCH$_3$, —C(CH$_3$)═CHCH$_3$, and —CH$_2$CH═CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C^{13}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (═O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclcic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-10 atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$ heterocycloalkyl. In another aspect, a heterocycloalkyl is a $C_2$-$C_6$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist.

The terms "administer," "administering", "administration," and the like, as used herein, refer to the methods that may be used to enable delivery of compounds or compositions to the desired site of biological action. These methods include, but are not limited to, oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, with respect to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound described herein, or a pharmaceutically acceptable salt thereof, and a co-agent, are both administered to a patient simultaneously in the form of a single entity or dosage. The term "non-fixed combination" means that the active ingredients, e.g., a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be performed by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Synthesis of Compounds

Compounds described herein are synthesized using standard synthetic techniques or using methods known in the art in combination with methods described herein.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

In some embodiments, the preparation of an EP2 inhibitor as described herein begins with the sequence of steps shown in General Scheme A.

General Scheme A

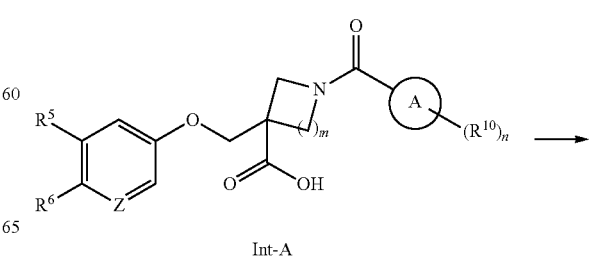

Int-A

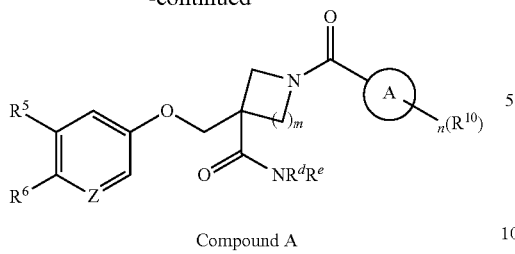

Compound A

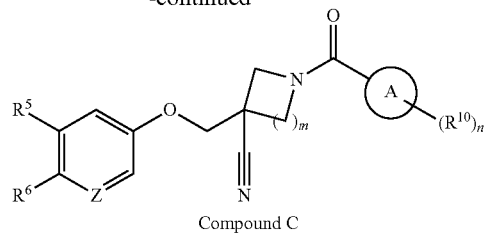

Compound C

In some embodiments, intermediates of the formula of Int-A are treated with a base and a suitable acid chloride or activated ester, which upon treatment with a suitable nucleophile, become amides of the formula of Compound A.

General Scheme B

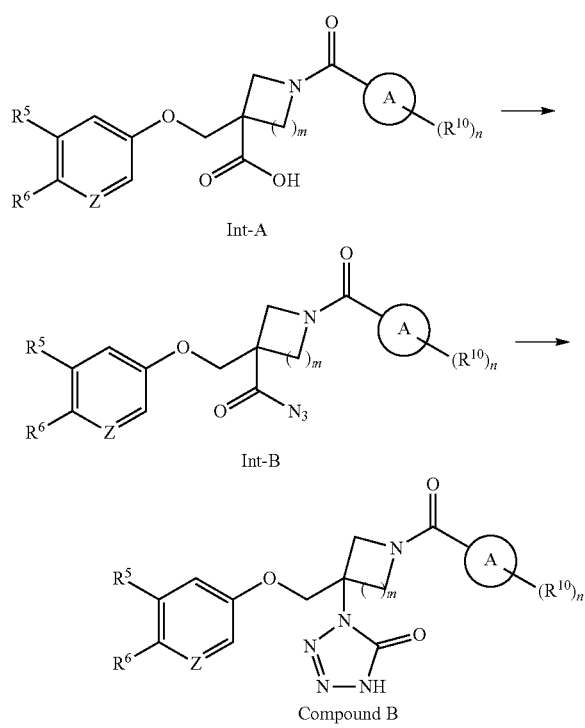

In some embodiments, intermediates of the formula of Int-A are treated with a base and a suitable azide reagent to generate acyl azide intermediates Int-B, which upon treatment with heat and a second azide, undergo a rearrangement reaction to give compounds of the formula of Compound B.

General Scheme C

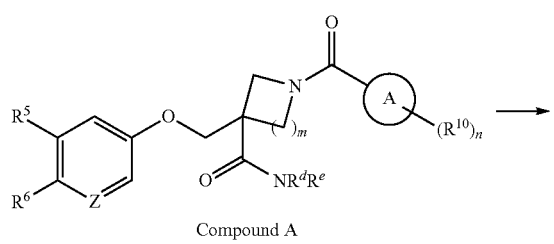

Compound A

In some embodiments, intermediates of the formula of Compound A, are treated with pyridine and a suitable anhydride to produce compounds of the formula of Compound C. In some embodiments, $R^d$ and $R^e$ are each H. Exemplary anhydrides for use in Scheme C include but are not limited to trifluoroacetic anhydride.

In some embodiments, compounds described herein are synthesized as outlined in the Examples.

Methods of Dosing and Treatment Regimens

In one embodiment, the compounds of Formula (I) are used in the preparation of medicaments for the treatment or prevention of diseases or conditions that would benefit from or by the reduction or inhibition of EP2 activity. In addition, a method for treating any of the diseases or conditions described herein in a mammal in need of such treatment, involves administration of pharmaceutical compositions that include at least one compound of Formula (I) or Formula (X), or a pharmaceutically acceptable salt, active metabolite, prodrug, or solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

In certain instances, it is appropriate to administer at least one compound of Formula (I) or Formula (X) in combination with another therapeutic agent. In one specific embodiment, a compound of Formula (I) or Formula (X) is co-administered with a second therapeutic agent, wherein the compound of Formula (I) or Formula (X) and the second therapeutic agent modulate different aspects of the disease or condition being treated, thereby providing a greater overall benefit than administration of either therapeutic agent alone.

155.9, 154.7, 130.6, 129.7 (d, J=41 Hz), 128.2, 118.8, 115.6 (d), 107.7, 106.2, 70.5, 58.0, 55.2, 53.9, 43.6, 26.2.

Example 2: Preparation of 1-(1-(4-fluorobenzoyl)-3-(((6-methoxynaphthalen-2-yl)oxy)methyl)azetidin-3-yl)-1,4-dihydro-5H-tetrazol-5-one (Compound 1-2)

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

EXAMPLES

The following examples are provided for illustrative purposes only and not to limit the scope of the claims provided herein.

Example 1: Preparation of 1-(4-fluorobenzoyl)-3-(((6-methoxynaphthalen-2-yl)oxy)methyl)-N-methylazetidine-3-carboxamide (Compound 1-1)

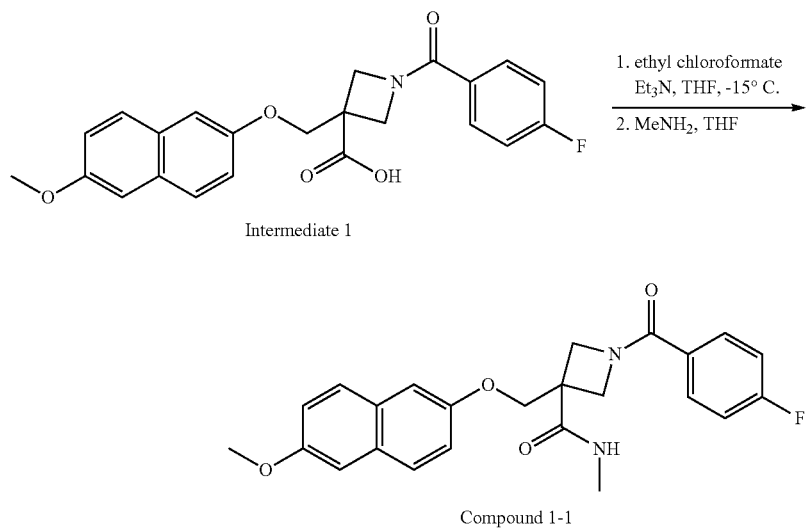

Intermediate 1

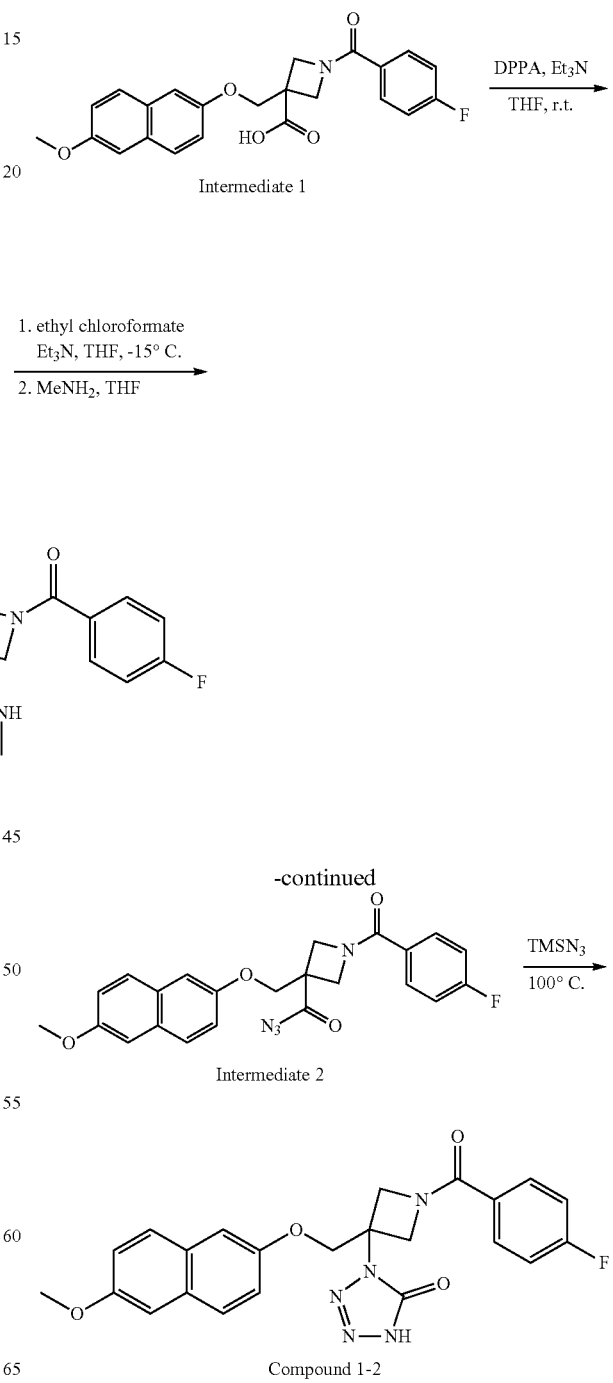

Compound 1-1

1-(4-fluorobenzoyl)-3-(((6-methoxynaphthalen-2-yl)oxy)methyl)-N-methylazetidine-3-carboxamide (Compound 1-1): To a mixture of Intermediate 1 (350 mg, 0.86 mmol) in anhydrous THF (1.0 mL) at ca. −15° C. was added Et$_3$N (104 mg, 1.0 mmol) and ethyl chloroformate (187 mg, 0.86 mmol), stirring at −10 to −15° C. for 2 h. To the stirring solution was added MeNH$_2$, 2M in THF (0.86 mL, 1.7 mmol). The mixture was allowed to warm to rt and stirred for 12 h, then H$_2$O (10 mL) added and the mixture was extracted with DCM (10 mL×4). The combined organic layers were dried over Na$_2$SO$_4$, filtered, concentrated under reduced pressure and the residue was purified by column chromatography on silica gel (n-heptane/ethyl acetate, 20/1 to 0/1) to give Compound 1-1 (28 mg, 8%) as a solid. LCMS (ESI): m/z [M+H] calc'd for C$_{24}$H$_{23}$FN$_2$O$_4$ 422.2; found 423.1; $^1$H NMR (400 MHz, DMSO-d$_6$) δ 8.10 (d, J=4.4 Hz, 1H), 7.70-7.76 (m, 4H), 7.29 (t, J=9.2 Hz, 4H), 7.08-7.14 (m, 2H), 4.59 (s, 2H), 4.24-4.30 (m, 2H), 4.10 (d, J=10.0 Hz, 1H), 3.83 (s, 3H), 2.66 (d, J=4.4 Hz, 3H); $^{19}$F NMR (377 MHz, DMSO-d$_6$) δ −109.2; $^{13}$C NMR (100 MHz, DMSO-d$_6$) δ 171.4, 168.3, 164.9 (d, J=247 Hz),

Step 1: Synthesis of 1-(4-fluorobenzoyl)-3-(((6-methoxynaphthalen-2-yl)oxy)methyl)azetidine-3-carbonyl azide (Intermediate 2)

1-(4-fluorobenzoyl)-3-(((6-methoxynaphthalen-2-yl)oxy)methyl)azetidine-3-carbonyl azide (Intermediate 2): To a mixture of Intermediate 1 (300 mg, 0.73 mmol) in THF (1 mL) at 0-5° C. under an atmosphere of $N_2$ was added $Et_3N$ (459 mL, 3.30 mmol) and DPPA (429 mL, 1.98 mmol). The mixture was warmed to rt and stirred for 16 h, then $H_2O$ (5 mL) added and the mixture extracted with DCM (4 mL×3). The combined organic layers were dried over anhydrous $Na_2SO_4$, filtered and the filtrate concentrated under reduced pressure to give Intermediate 2 (300 mg, 94%) as an oil, which was used directly in the step directly without further purification. LCMS (ESI): m/z [M+H] calc'd for $C_{23}H_{19}FN_4O_4$ 434.1; found 435.1.

Step 2: Synthesis of 1-(1-(4-fluorobenzoyl)-3-(((6-methoxynaphthalen-2-yl)oxy)methyl)azetidin-3-yl)-1,4-dihydro-5H-tetrazol-5-one (Compound 1-2)

1-(1-(4-fluorobenzoyl)-3-(((6-methoxynaphthalen-2-yl)oxy)methyl)azetidin-3-yl)-1,4-dihydro-5H-tetrazol-5-one (Compound 1-2): A mixture of Intermediate 2 (150 mg, 0.35 mmol) and $TMSN_3$ (273 mL, 2.1 mmol) was heated to 95-100° C. and stirred for 12 h. The mixture was concentrated under reduced pressure and the residue was purified by preparative HPLC to give Compound 1-2 (20 mg, 7%) as a solid. LCMS (ESI): m/z [M−H] calc'd for $C_{23}H_{20}FN_5O_4$ 449.2; found 448.2; $^1$H NMR (400 MHz, DMSO-$d_6$) δ 7.70-7.79 (m, 4H), 7.26-7.33 (m, 4H), 7.08-7.14 (m, 2H), 4.96-5.00 (m, 1H), 4.68 (d, J=10.0 Hz, 2H), 4.45 (s, 2H), 4.43-4.46 (m, 1H), 3.83 (s, 3H); $^{19}$F NMR (377 MHz, DMSO-$d_6$) δ −108.9.

Example 3. Preparation of 1-(4-fluorobenzoyl)-3-(((6-methoxynaphthalen-2-yl)oxy)methyl)azetidine-3-carbonitrile (Compound 1-3)

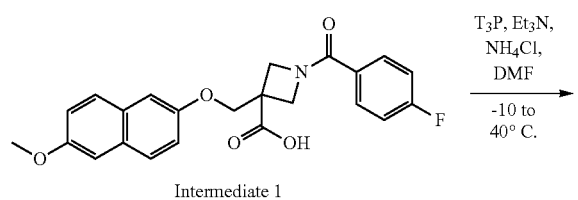

Intermediate 1

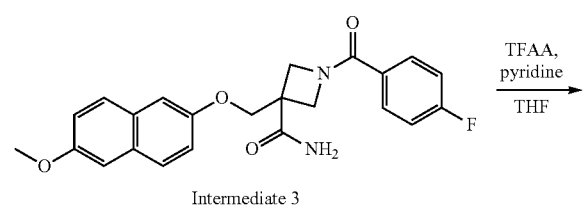

Intermediate 3

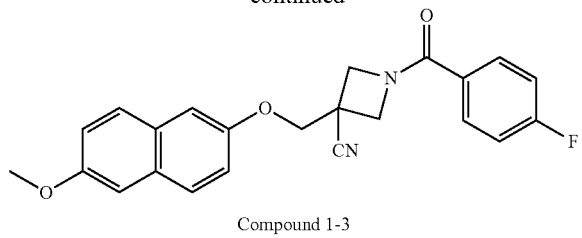

Compound 1-3

Step 1. Synthesis of 1-(4-fluorobenzoyl)-3-(((6-methoxynaphthalen-2-yl)oxy)methyl)azetidine-3-carboxamide (Intermediate 3)

1-(4-fluorobenzoyl)-3-(((6-methoxynaphthalen-2-yl)oxy)methyl)azetidine-3-carboxamide (Intermediate 3): To a mixture of Intermediate 1 (150 mg, 0.37 mmol) in DMF (1 mL) at −10-0° C. was added $Et_3N$ (128 mL, 0.92 mmol) and T3P, 50% solution (436 mL, 0.73 mmol). The mixture was warmed to rt and stirred for 30 min then $NH_4Cl$ (39 mg, 0.73 mmol) in DMF was added. The mixture was stirred at rt for 12 h, then $H_2O$ (2 mL) added and the mixture extracted with EtOAc (2 mL×3). The combined organic layers were washed with brine solution (2 mL×3), dried over anhydrous $Na_2SO_4$, filtered and the filtrate was concentrated under reduced pressure to give Intermediate 3 (100 mg, 67%) as a solid, which was used directly in the next step directly without further purification. LCMS (ESI): m/z [M+H] calc'd for $C_{23}H_{21}FN_2O_4$ 408.2; found 409.0.

Step 2. Synthesis of 1-(4-fluorobenzoyl)-3-(((6-methoxynaphthalen-2-yl)oxy)methyl)azetidine-3-carbonitrile (Compound 1-3)

1-(4-fluorobenzoyl)-3-(((6-methoxynaphthalen-2-yl)oxy)methyl)azetidine-3-carbonitrile (Compound 1-3): To a mixture of Intermediate 3 (100 mg, 0.25 mmol) in THF (1 mL) at rt was added pyridine (51 mL, 0.64 mmol) and trifluoroacetic acid anhydride (TFAA) (87 mL, 0.64 mmol. The mixture was stirred at rt for 12 h, then $H_2O$ (5 mL) added and the mixture was extracted with EtOAc (4 mL×3). The combined organic layers were dried over $Na_2SO_4$ and filtered, the filtrate was concentrated under reduced pressure and the residue was purified by preparative HPLC to give Compound 1-3 (26 mg, 27%) as a solid. LCMS (ESI): m/z [M+H] calc'd for $C_{23}H_{19}FN_2O_3$ 390.1; found 391.1; $^1$H NMR (400 MHz, DMSO-$d_6$) δ 7.78-7.71 (m, 4H), 7.27-7.34 (m, 4H), 7.11-7.16 (m, 2H), 4.83 (d, J=8.4 Hz, 1H), 4.55 (s, 2H), 4.42-4.50 (m, 2H), 4.27 (d, J=8.4 Hz, 1H), 3.84 (s, 3H); $^{19}$F NMR (377 MHz, DMSO-$d_6$) δ −107.8.

Example 4. Preparation of racemic 3-(((4'-cyano-[1,1'-biphenyl]-4-yl)oxy)methyl)-1-(4-methoxybenzoyl)-N-methylpyrrolidine-3-carboxamide (Compound 2-1)

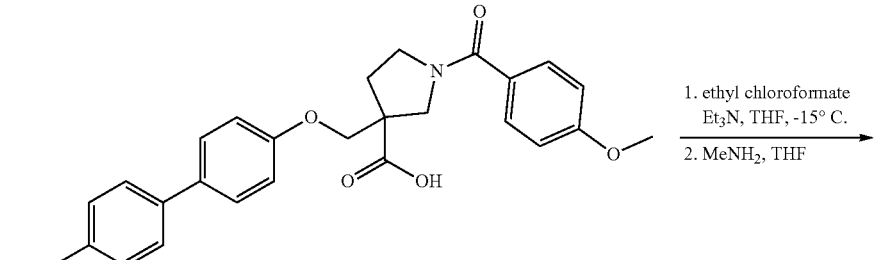

Intermediate 4

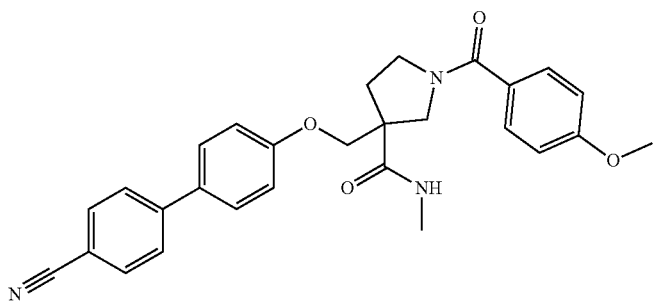

Compound 2-1

Racemic 3-(((4'-cyano-[1,1'-biphenyl]-4-yl)oxy)methyl)-1-(4-methoxybenzoyl)-N-methylpyrrolidine-3-carboxamide (Compound 2-1): To a mixture of (±) 3-(((4'-cyano-[1,1'-biphenyl]-4-yl)oxy)methyl)-1-(4-methoxybenzoyl)pyrrolidine-3-carboxylic acid Intermediate 4 (600 mg, 1.3 mmol) in anhydrous THF (3.6 mL) at ca. −15° C. was added Et$_3$N (398 mg, 3.9 mmol) and ethyl chloroformate (569 mg, 5.2 mmol). The mixture was stirred at -15° C. for 3 h, then methylamine, 2M (5.24 mL, 10.5 mmol) was added. The mixture was allowed to warm to rt and stirred for 12 h, then H$_2$O (10 mL) added and extracted with DCM (10 mL×4). The combined organic layers were dried over Na$_2$SO$_4$, filtered, concentrated under reduced pressure and the residue was purified by preparative-HPLC to give Compound 2-1 (15 mg, 3%) as a solid. LCMS (ESI): m/z [M+H] calc'd for C$_{28}$H$_{27}$N$_3$O$_4$ 469.2; found 470.1.

Example 5. Preparation of racemic 4'-((1-(4-methoxybenzoyl)-3-(5-oxo-4,5-dihydro-1H-tetrazol-1-yl)pyrrolidin-3-yl)methoxy)-[1,1'-biphenyl]-4-carbonitrile (Compound 2-2)

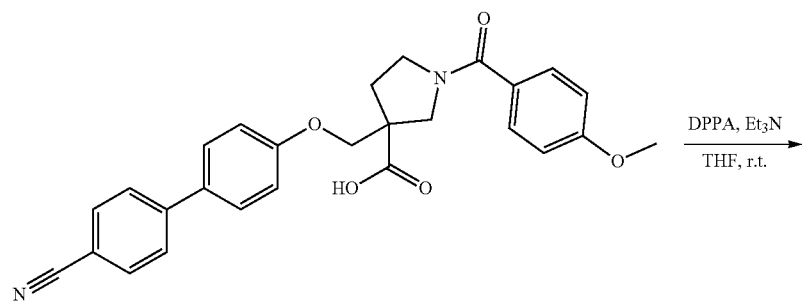

Intermediate 4

-continued

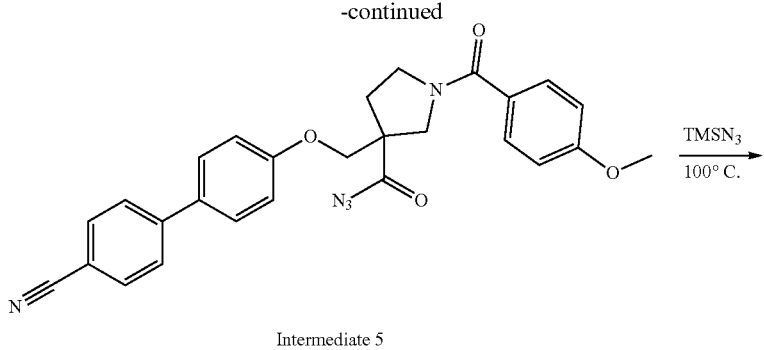

Intermediate 5

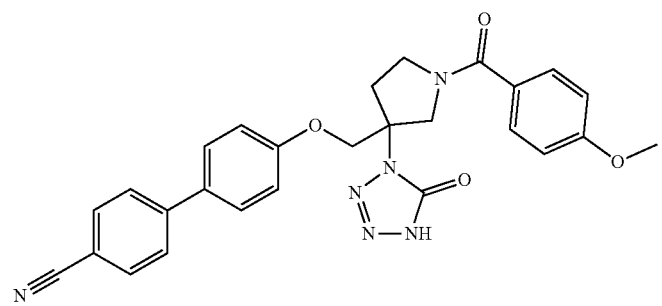

Compound 2-2

Step 1. Synthesis of (±) 3-(((4'-cyano-[1,1'-biphenyl]-4-yl)oxy)methyl)-1-(4-methoxybenzoyl)pyrrolidine-3-carbonyl azide (Intermediate 5)

To a mixture of (±) 3-(((4'-cyano-[1,1'-biphenyl]-4-yl)oxy)methyl)-1-(4-methoxybenzoyl)pyrrolidine-3-carboxylic acid Intermediate 4 (0.6 g, 1.3 mmol) in THF (6 mL) at 0-5° C. under an atmosphere of $N_2$ was added $Et_3N$ (598 mg, 5.9 mmol) and DPPA (977 mg, 3.6 mmol). The mixture was warmed to rt and stirred for 16 h, then $H_2O$ (20 mL) added and the mixture was extracted with DCM (20 mL×3). The combined organic layers were dried over $Na_2SO_4$, filtered and the filtrate was concentrated under reduced pressure to give (±) 3-(((4'-cyano-[1,1'-biphenyl]-4-yl)oxy)methyl)-1-(4-methoxybenzoyl)pyrrolidine-3-carbonyl azide (600 mg, 95%) as an oil, that was used directly in next step directly without further purification. LCMS (ESI): m/z [M+H] calc'd for $C_{27}H_{23}N_5O_4$ 481.2; found 482.0.

Step 2. Synthesis of (±) 4'-((1-(4-methoxybenzoyl)-3-(5-oxo-4,5-dihydro-1H-tetrazol-1-yl)pyrrolidin-3-yl)methoxy)-[1,1'-biphenyl]-4-carbonitrile (Compound 2-2)

(±) 4'-((1-(4-methoxybenzoyl)-3-(5-oxo-4,5-dihydro-1H-tetrazol-1-yl)pyrrolidin-3-yl)methoxy)-[1,1'-biphenyl]-4-carbonitrile (Compound 2-2): A mixture of (±) 3-(((4'-cyano-[1,1'-biphenyl]-4-yl)oxy)methyl)-1-(4-methoxybenzoyl)pyrrolidine-3-carbonyl azide Intermediate 5 (0.6 g, 1.3 mmol) and $TMSN_3$ (983 mL, 7.5 mmol) was heated to 95° C. and stirred for 16 h. The mixture was purified directly by preparative-HPLC to give Compound 2-2 (40 mg, 6%) as a solid. LCMS (ESI): m/z [M+H] calc'd for $C_{27}H_{24}N_6O_4$ 496.2; found 497.1; $^1$H NMR (400 MHz, $CDCl_3$) δ 8.59-8.98 (m, 1H), 7.68 (d, J=8.0 Hz, 2H), 7.59 (d, J=8.0 Hz, 2H), 7.53 (d, J=8.4 Hz, 2H), 7.48 (d, J=8.0 Hz, 2H), 6.90-6.92 (m, 4H), 4.67-4.70 (m, 1H), 4.27-4.26 (m, 2H), 4.02-4.08 (m, 1H), 3.78-3.90 (m, 5H), 3.09 (br. s, 1H), 2.49-2.57 (m, 1H).

Example 6. Preparation of racemic 3-(((4'-cyano-[1,1'-biphenyl]-4-yl)oxy)methyl)-1-(4-methoxybenzoyl)pyrrolidine-3-carbonitrile (Compound 2-3)

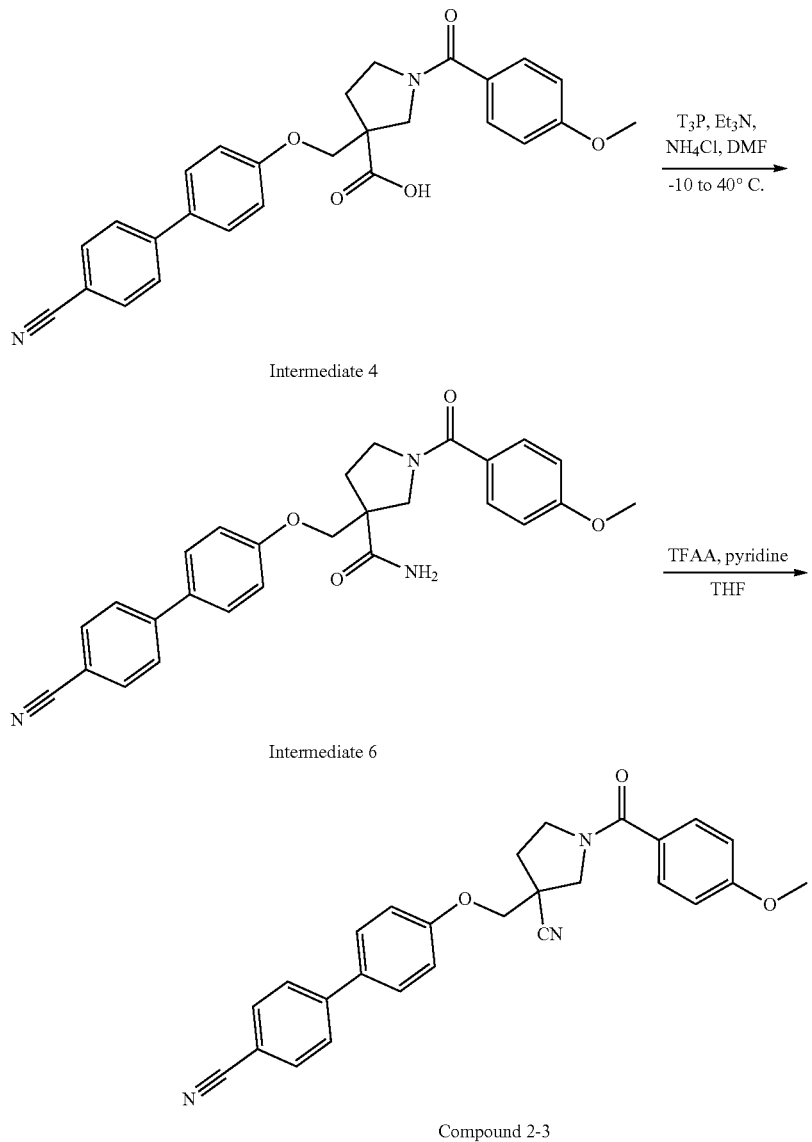

Step 1. Synthesis of 3-(((4'-cyano-[1,1'-biphenyl]-4-yl)oxy)methyl)-1-(4-methoxybenzoyl)pyrrolidine-3-carboxamide (Intermediate 6)

3-(((4'-cyano-[1,1'-biphenyl]-4-yl)oxy)methyl)-1-(4-methoxybenzoyl)pyrrolidine-3-carboxamide (Intermediate 6): To a mixture of (±) 3-(((4'-cyano-[1,1'-biphenyl]-4-yl)oxy)methyl)-1-(4-methoxybenzoyl)pyrrolidine-3-carboxylic acid Intermediate 4 (0.6 g, 1.3 mmol) in DMF (6 mL) at −10° C. was added Et$_3$N (332 mg, 3.3 mmol) and T3P, 50% solution (1.56 mL, 2.6 mmol). The mixture was warmed to rt and stirred for 0.5 h, then NH$_4$Cl (141 mg, 2.6 mmol) in DMF was added and the mixture was warmed to 40° C. and stirred for 12 h. H$_2$O (10 mL) was added and the mixture was extracted with EtOAc (10 mL×3). The combined organic layers were washed with brine (10 mL×2), dried over anhydrous Na$_2$SO$_4$, filtered and the filtrate was concentrated under reduced pressure to give 3-(((4'-cyano-[1,1'-biphenyl]-4-yl)oxy)methyl)-1-(4-methoxybenzoyl)pyrrolidine-3-carboxamide (500 mg, 84%) as an oil that was used directly in the next step without further purification. LCMS (ESI): m/z [M+H] calc'd for $C_{27}H_{25}N_3O_4$ 455.2; found 456.0.

Step 2. Synthesis of (±) 3-(((4'-cyano-[1,1'-biphenyl]-4-yl)oxy)methyl)-1-(4-methoxybenzoyl)pyrrolidine-3-carbonitrile (Compound 2-2)

(±) 3-(((4'-cyano-[1,1'-biphenyl]-4-yl)oxy)methyl)-1-(4-methoxybenzoyl)pyrrolidine-3-carbonitrile (Compound 2-2): To a mixture of (±) 3-(((4'-cyano-[1,1'-biphenyl]-4-yl)oxy)methyl)-1-(4-methoxybenzoyl)pyrrolidine-3-carboxamide Intermediate 6 (500 mg, 1.1 mmol) in THF (3 mL) at rt was added pyridine (226 mg, 2.9 mmol) and TFAA (599 mg, 2.9 mmol). The mixture was stirred at rt for 12 h, then H$_2$O (5 mL) was added and the mixture was extracted with EtOAc (4 mL×3). The combined organic layers were dried over Na$_2$SO$_4$, filtered, the filtrate was concentrated under reduced pressure and the residue was purified by preparative-HPLC to give (±) 3-(((4'-cyano-[1,1'-biphenyl]-4-yl)oxy)methyl)-1-(4-methoxybenzoyl)pyrrolidine-3-carbonitrile Compound 2-3 (40 mg, 8%) as a solid; $^1$H NMR (400 MHz, CDCl$_3$) δ 7.72 (d, J=8.4 Hz, 2H), 7.66 (d, J=8.4 Hz, 2H), 7.56 (m, 4H), 7.03 (d, J=7.2 Hz, 2H), 6.94 (d, J=8.8 Hz, 2H), 4.13-4.19 (m, 3H), 3.86-3.94 (m, 3H), 3.86 (s, 3H), 2.50-2.55 (m, 1H), 2.33-2.34 (m, 1H).

Example 7: Preparation of 3-[({4'-cyano-[1,1'-biphenyl]-4-yl}oxy)methyl]-N-(ethanesulfonyl)-1-(4-methoxybenzoyl)pyrrolidine-3-carboxamide (Compound 4-25)

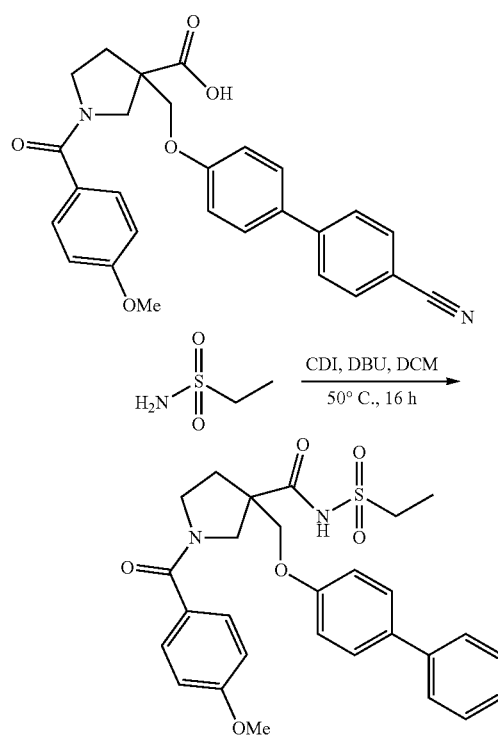

To a mixture of 3-[({4'-cyano-[1,1'-biphenyl]-4-yl}oxy)methyl]-1-(4-methoxybenzoyl)pyrrolidine-3-carboxylic acid (80 mg, 0.18 mmol) in DCM (2 mL) was added CDI (113 mg, 0.70 mmol). The mixture was stirred at 50° C. for 4 h. To the mixture was added ethanesulfonamide (95 mg, 0.88 mmol) and DBU (106 mg, 0.70 mmol). The mixture was stirred at 50° C. for 16 h. The mixture was concentrated under reduced pressure and the residue was purified by preparative-HPLC with the following conditions (Column: XBridge Shield RP18 OBD Column, 30*150 mm, 5 μm; Mobile Phase A: Water (10 mmol/L NH$_4$HCO$_3$), Mobile Phase B: ACN; Flow rate: 60 mL/min; Gradient: 21% B to 41% B in 7 min, 41% B; Wave Length: 254 nm; RT1(min): 5.55; Number Of Runs: 0) to afford 3-[({4'-cyano-[1,1'-biphenyl]-4-yl}oxy)methyl]-N-(ethanesulfonyl)-1-(4-methoxybenzoyl)pyrrolidine-3-carboxamide (29.5 mg, 31%) as a solid. LC/MS: mass calcd. For C$_{29}$H$_{29}$N$_3$O$_6$S: 547.1, found: 548.1 [M+H]$^+$; $^1$H NMR (300 MHz, CD$_3$OD) δ 7.77-7.80 (m, 4H), 7.50-7.69 (m, 4H), 6.99-7.14 (m, 4H), 4.09-4.45 (m, 3H), 3.85 (d, J=3.0 Hz, 3H), 3.60-3.79 (m, 3H), 3.20 (br, 2H), 2.40-2.52 (m, 1H), 2.02-2.17 (m, 1H), 1.10-1.28 (m, 3H) [note: HNMR was influenced by rotamers, which can be widely observed in this series of targets].

Example 8: Preparation of N-cyano-3-(((4'-cyano-[1,1'-biphenyl]-4-yl)oxy)methyl)-1-(4-methoxybenzoyl)pyrrolidine-3-carboxamide (Compound 4-21)

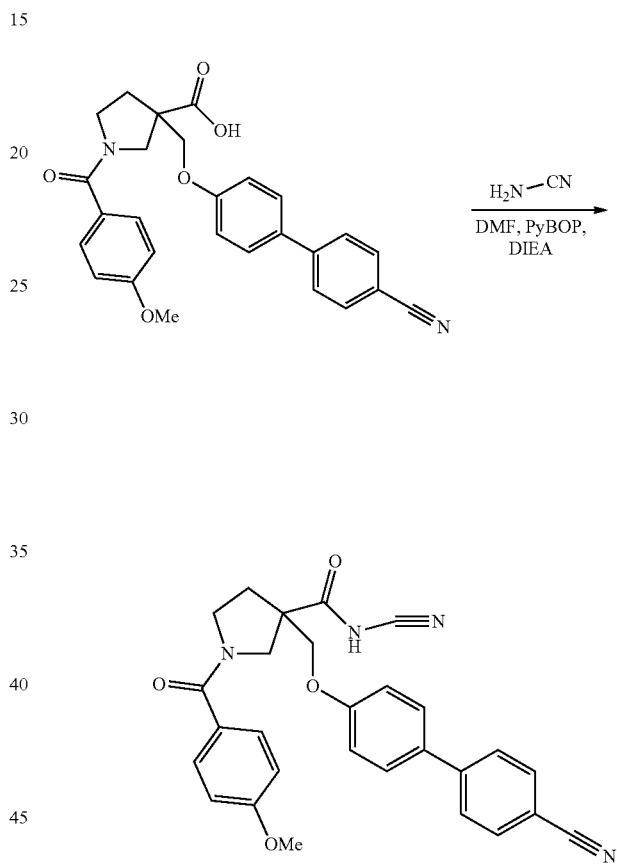

To a mixture of 3-[({4'-cyano-[1,1'-biphenyl]-4-yl}oxy)methyl]-1-(4-methoxybenzoyl)pyrrolidine-3-carboxylic acid (50 mg, 0.11 mmol) in DMF (1 mL) was added cyanamide (5 mg, 0.11 mmol), PyBOP (86 mg, 0.17 mmol) and DIPEA (28 mg, 0.22 mmol). The mixture was stirred at rt for 12 h, then filtered. The filtrate was purified directly by preparative-HPLC with following conditions (Column: Xselect CSH C18 OBD Column 30*150 mm 5 μm, n; Mobile Phase A: Water(0.05% HCl), Mobile Phase B: ACN; Flow rate: 60 mL/min; Gradient: 49% B to 69% B in 7 min, 69% B; Wave Length: 254 nm; RT1(min): 5.45; Number Of Runs: 0) to afford N-cyano-3-[({4'-cyano-[1,1'-biphenyl]-4-yl}oxy)methyl]-1-(4-methoxybenzoyl)pyrrolidine-3-carboxamide (8.2 mg, 15%) as a solid. LC/MS: mass calcd. For C$_{28}$H$_{24}$N$_4$O$_4$: 480.1, found: 481.1 [M+H]$^+$; $^1$H NMR (300 MHz, CD$_3$OD) δ 7.79 (s, 4H), 7.64-7.70 (m, 2H), 7.54 (d, J=7.8 Hz, 2H), 6.96-7.18 (m, 4H), 4.15-4.37 (m, 3H), 3.85 (s, 3H), 3.61-3.82 (m, 3H), 2.40-2.55 (m, 1H), 2.26 (br, 1H).

Example 9: Preparation of 3-[({4'-cyano-[1,1'-biphenyl]-4-yl}oxy)methyl]-1-(4-methoxybenzoyl)-N-(2,2,2-trifluoroethanesulfonyl)pyrrolidine-3-carboxamide (Compound 4-26)

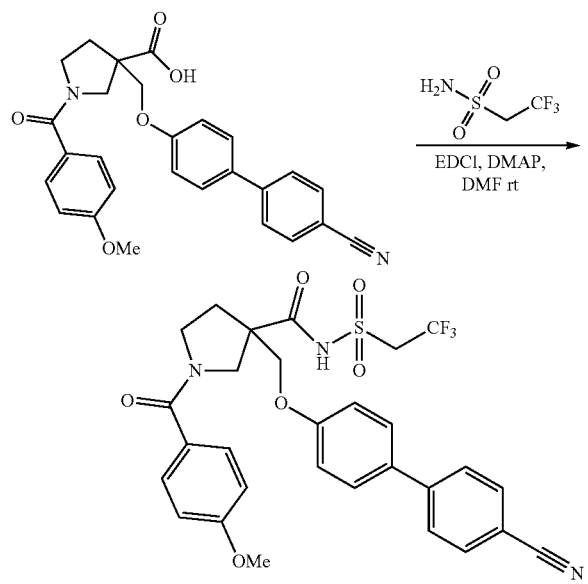

To a mixture of 3-[({4'-cyano-[1,1'-biphenyl]-4-yl}oxy)methyl]-1-(4-methoxybenzoyl)pyrrolidine-3-carboxylic acid (100 mg, 0.22 mmol) and 2,2,2-trifluoroethanesulfonamide (70 mg, 0.44 mmol) in DMF (2 mL) was added EDCI (63 mg, 0.33 mmol) and DMAP (13 mg, 0.11 mmol). The mixture was stirred at rt for 2 h, then purified directly by preparative-HPLC with the following conditions (Column: XBridge Prep OBD $C_{18}$ Column, 30*150 mm, 5 μm; Mobile Phase A: Water (10 mmol/L $NH_4HCO_3$+0.1% $NH_3$—$H_2O$), Mobile Phase B: ACN; Flow rate: 60 mL/min; Gradient: 26% B to 56% B in 7 min, 56% B; Wave Length: 254 nm; RT1(min): 6; Number Of Runs: 0) to afford 3-[({4'-cyano-[1,1'-biphenyl]-4-yl}oxy)methyl]-1-(4-methoxybenzoyl)-N-(2,2,2-trifluoroethanesulfonyl)pyrrolidine-3-carboxamide (26.6 mg, 20%) as a solid. LC/MS: mass calcd. For $C_{29}H_{26}F_3N_3O_6S$: 601.1, found: 602.0 $[M+H]^+$; $^1H$ NMR (300 MHz, $CD_3OD$) δ 7.70-7.80 (m, 4H), 7.50-7.70 (m, 4H), 6.94-7.15 (m, 4H), 4.00-4.45 (m, 5H), 3.85 (d, J=6.0 Hz, 3H), 3.62-3.80 (m, 3H), 2.48-2.60 (m, 1H), 2.01-2.16 (m, 1H) $^{19}F$ NMR (282 MHz, Methanol-$d_4$) δ −63.4.

The compounds of Table 5 can be prepared according to the preceding examples ("Ex. No.") described herein.

TABLE 5

| ID No. | Structure | $^1$H-NMR | MS (M + H)$^+$ | Ex. No. |
|---|---|---|---|---|
| 4-19 | 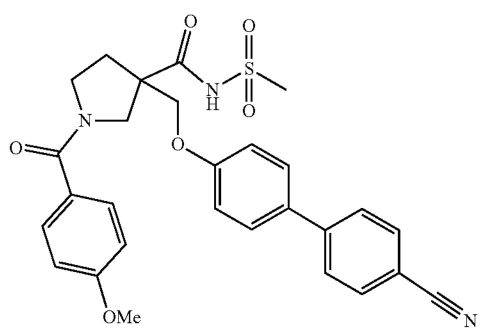 [SMILES: COc1ccc(C(=O)N2CCC(COc3ccc(-c4ccc(C#N)cc4)cc3)(C(=O)NS(C)(=O)=O)C2)cc1] | $^1$H NMR (400 MHz, DMSO-$d_6$) δ 7.82-7.88 (m, 4H), 7.67-7.73 (m, 2H), 7.47-7.51 (m, 2H), 6.95-7.09 (m, 4H), 6.91 (s, 1H), 3.93-4.28 (m, 3H), 3.79 (s, 3H), 3.43-3.57 (m, 3H), 2.62-2.72 (m, 3H), 2.25-2.33 (m, 1H), 1.88-1.97 (m, 1H), 1.62-1.68 (m, 1H). | 534.0 | 7 |
| 4-27 | 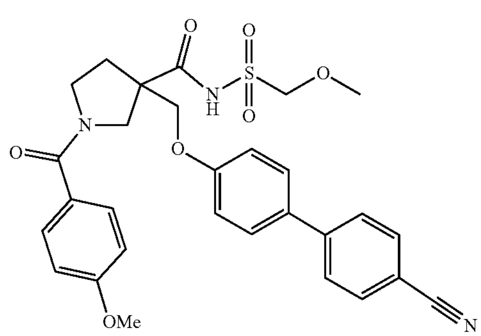 [SMILES: COCS(=O)(=O)NC(=O)C1(COc2ccc(-c3ccc(C#N)cc3)cc2)CCN(C(=O)c2ccc(OC)cc2)C1] | $^1$H NMR (300 MHz, $CD_3OD$) δ 7.71-7.78 (m, 4H), 7.50-7.70 (m, 4H), 6.94-7.14 (m, 4H), 4.51-4.62 (m, 2H), 4.09-4.59 (m, 3H), 3.85 (d, J = 3.0 Hz, 3H), 3.63-3.81 (m, 3H), 3.50-3.60 (m, 3H), 2.50-2.60 (m, 1H), 2.10-2.20 (m, 1H). | 564.1 | 7 |

TABLE 5-continued

| ID No. | Structure | ¹H-NMR | MS (M + H)⁺ | Ex. No. |
|---|---|---|---|---|
| 4-28 | 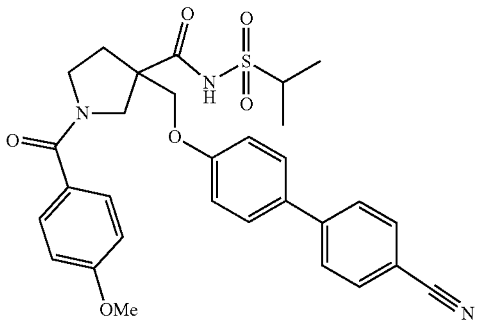 [SMILES: COc1ccc(C(=O)N2CCC(COc3ccc(-c4ccc(C#N)cc4)cc3)(C(=O)NS(=O)(=O)C(C)C)C2)cc1] | ¹H NMR (300 MHz, CD₃OD) δ 7.72-7.83 (m, 4H), 7.55-7.64 (m, 4H), 6.94-7.15 (m, 4H), 4.09-4.48 (m, 3H), 3.85 (d, J = 3.0 Hz, 3H), 3.63-3.79 (m, 4H), 2.41-2.51 (m, 1H), 2.01-2.19 (m, 1H), 1.15-1.33 (m, 6H). | 562.1 | 7 |
| 4-29 | 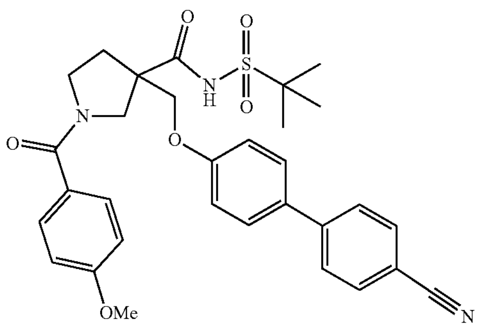 [SMILES: COc1ccc(C(=O)N2CCC(COc3ccc(-c4ccc(C#N)cc4)cc3)(C(=O)NS(=O)(=O)C(C)(C)C)C2)cc1] | ¹H NMR (300 MHz, CD₃OD) δ 7.72-7.83 (m, 4H), 7.60-7.70 (m, 2H), 7.50-7.53 (m, 2H), 6.94-7.14 (m, 4H), 4.10-4.45 (m, 3H), 3.85 (s, 3H), 3.61-3.75 (m, 3H), 2.42-2.54 (m, 1H), 2.01-2.20 (m, 1H), 1.32-1.39 (m, 9H). | 576.2 | 7 |
| 4-30 | 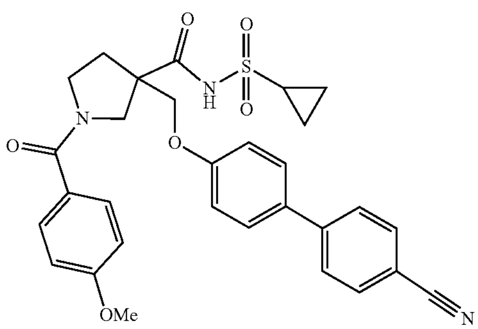 [SMILES: COc1ccc(C(=O)N2CCC(COc3ccc(-c4ccc(C#N)cc4)cc3)(C(=O)NS(=O)(=O)C3CC3)C2)cc1] | ¹H NMR (300 MHz, CD₃OD) δ 7.71-7.77 (m, 4H), 7.50-7.69 (m, 4H), 6.94-7.15 (m, 4H), 4.08-4.38 (m, 3H), 3.85 (d, J = 3.0 Hz, 3H), 3.62-3.80 (m, 3H), 2.86 (br, 1H), 2.40-2.52 (m, 1H), 2.01-2.19 (m, 1H), 0.95-1.02 (m, 2H), 0.70-0.82 (m, 2H). | 560.1 | 7 |
| 4-31 | 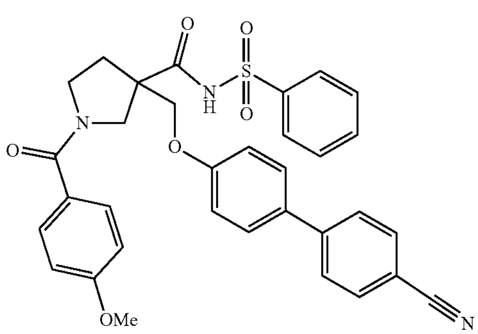 [SMILES: COc1ccc(C(=O)N2CCC(COc3ccc(-c4ccc(C#N)cc4)cc3)(C(=O)NS(=O)(=O)c3ccccc3)C2)cc1] | ¹H NMR (300 MHz, CD₃OD) δ 7.82-7.97 (m, 2H), 7.74-7.80 (m, 4H), 7.52-7.69 (m, 3H), 7.37-7.52 (m, 4H), 6.86-7.02 (m, 4H), 4.12-4.40 (m, 3H), 3.84 (d, J = 3.0 Hz, 3H), 3.60-3.76 (m, 3H), 2.34-2.48 (m, 1H), 2.00-2.18 (m, 1H). | 596.1 | 7 |

TABLE 5-continued

| ID No. | Structure | ¹H-NMR | MS (M + H)⁺ | Ex. No. |
|---|---|---|---|---|
| 4-13 | 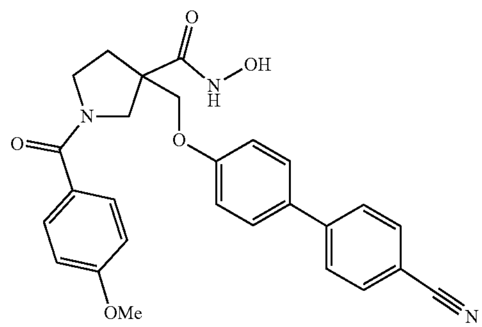 [SMILES: COc1ccc(C(=O)N2CCC(COc3ccc(-c4ccc(C#N)cc4)cc3)(C(=O)NO)C2)cc1] | ¹H NMR (400 MHz, DMSO-d₆) δ 10.74 (s, 1H), 8.92 (s, 1H), 7.85-7.90 (m, 4H), 7.70-7.75 (m, 2H), 7.49-7.53 (m, 2H), 6.95-7.09 (m, 4H), 4.09-4.26 (m, 2H), 3.95-3.98 (m, 1H), 3.80 (s, 3H), 3.58-3.68 (m, 3H), 2.09-2.30 (m, 2H). | 472.2 | 8 |
| 4-20 | 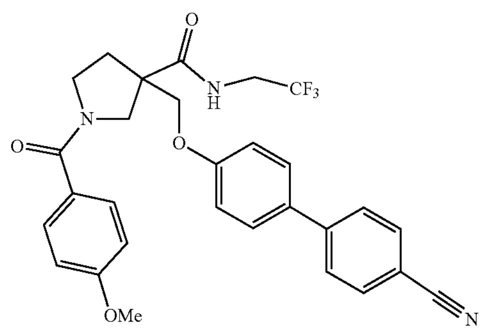 [SMILES: COc1ccc(C(=O)N2CCC(COc3ccc(-c4ccc(C#N)cc4)cc3)(C(=O)NCC(F)(F)F)C2)cc1] | ¹H NMR (400 MHz, CDCl₃) δ 7.72-7.75 (m, 2H), 7.65-7.77 (m, 2H), 7.51-7.61 (m, 4H), 7.01-7.04 (m, 2H), 6.93 (d, J = 8 Hz, 2H), 4.12-4.30 (m, 3H), 3.97-4.02 (m, 2H), 3.80-3.88 (m, 6H), 2.47-2.58 (m, 1H), 2.10-2.32 (m, 1H). ¹⁹F NMR (376 MHz, DMSO-d₆) δ −70.6. | 538.1 | 8 |
| 4-22 | 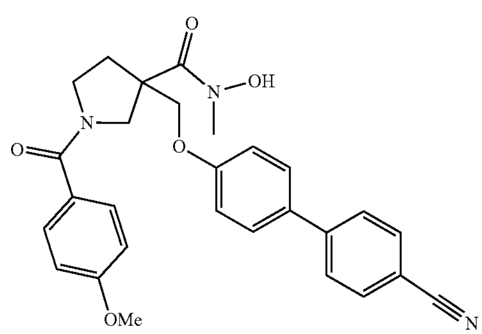 [SMILES: COc1ccc(C(=O)N2CCC(COc3ccc(-c4ccc(C#N)cc4)cc3)(C(=O)N(C)O)C2)cc1] | ¹H NMR (400 MHz, DMSO-d₆) δ 10.02-10.08 (m, 1H), 7.85-7.90 (m, 4H), 7.68-7.71 (m, 2H), 7.47-7.52 (m, 2H), 6.95-7.09 (m, 4H), 4.19-4.44 (m, 2H), 3.95-4.05 (m, 1H), 3.80 (s, 3H), 3.62-3.64 (m, 2H), 3.47-3.53 (m, 1H), 3.11-3.15 (m, 3H), 2.38-2.46 (m, 1H), 2.08-2.17 (m, 1H). | 486.2 | 8 |
| 4-23 | 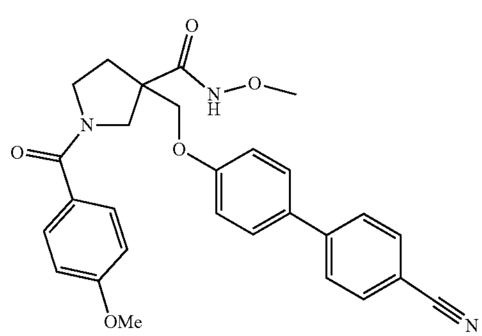 [SMILES: CONC(=O)C1(COc2ccc(-c3ccc(C#N)cc3)cc2)CCN(C(=O)c2ccc(OC)cc2)C1] | ¹H NMR (400 MHz, DMSO-d₆) δ 11.31-11.33 (m, 1H), 7.85-7.90 (m, 4H), 7.69-7.75 (m, 2H), 7.46-7.54 (m, 2H), 6.96-7.13 (m, 4H), 4.10-4.27 (m, 2H), 3.88-3.97 (m, 1H), 3.80 (s, 3H), 3.52-3.64 (m, 6H), 2.29-2.34 (m, 1H), 2.08-2.11 (m, 1H). | 486.1 | 8 |

TABLE 5-continued

| ID No. | Structure | ¹H-NMR | MS (M + H)⁺ | Ex. No. |
|---|---|---|---|---|
| 4-24 | 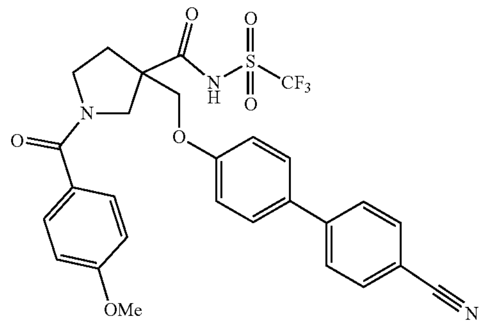 | ¹H NMR (400 MHz, DMSO-$d_6$) δ 7.83-7.89 (m, 4H), 7.67-7.73 (m,2H), 7.48 (t, J = 7.2 Hz, 2H), 6.95-7.07 (m, 5H), 3.91-4.3 (m, 3H), 3.79 (s, 3H), 3.46-3.60 (m, 3H), 2.25-2.27 (m, 1H), 1.91-2.01 (m, 1H). ¹⁹F (376 MHz, DMSO-$d_6$) δ −77.2. | 588.0 | 9 |

Example 9: Preparation of Methoxymethanesulfonamide

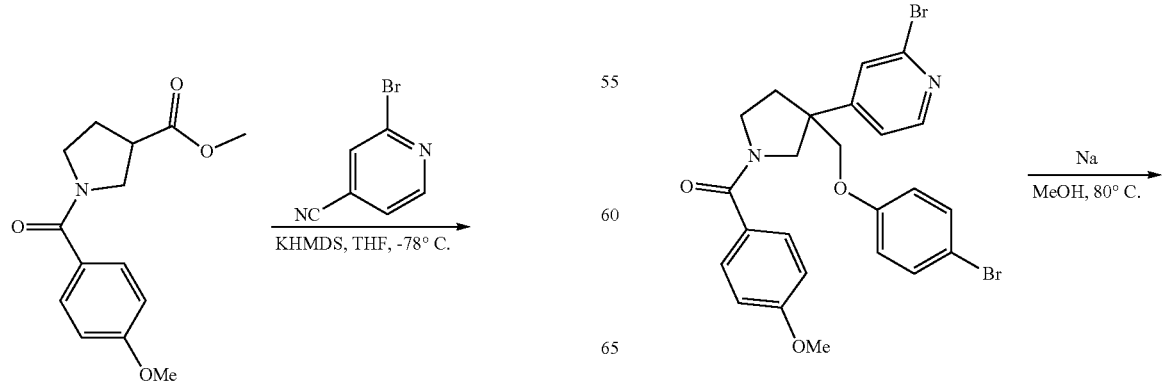

To a stirred mixture of chloromethanesulfonamide (500 mg, 3.86 mmol) in MeOH (5 mL) was added Ag₂CO₃ (5.32 g, 19.3 mmol). The resulting mixture was heated to 100° C. and stirred overnight, then filtered, and the filter cake was washed with MeOH (3×5 mL). The filtrate was concentrated under reduced pressure to afford methoxymethanesulfonamide (30 mg, 6%) as an oil. The crude product was used for next step in the synthesis of Compound 4-27 without further purification.

Example 10: Preparation of 4'-{[1-(4-methoxybenzoyl)-3-(2-methoxypyridin-4-yl)pyrrolidin-3-yl]methoxy}-[1,1'-biphenyl]-4-carbonitrile (Compound 4-32)

Step 1: Synthesis of methyl 3-(2-bromopyridin-4-yl)-1-(4-methoxybenzoyl)pyrrolidine-3-carboxylate

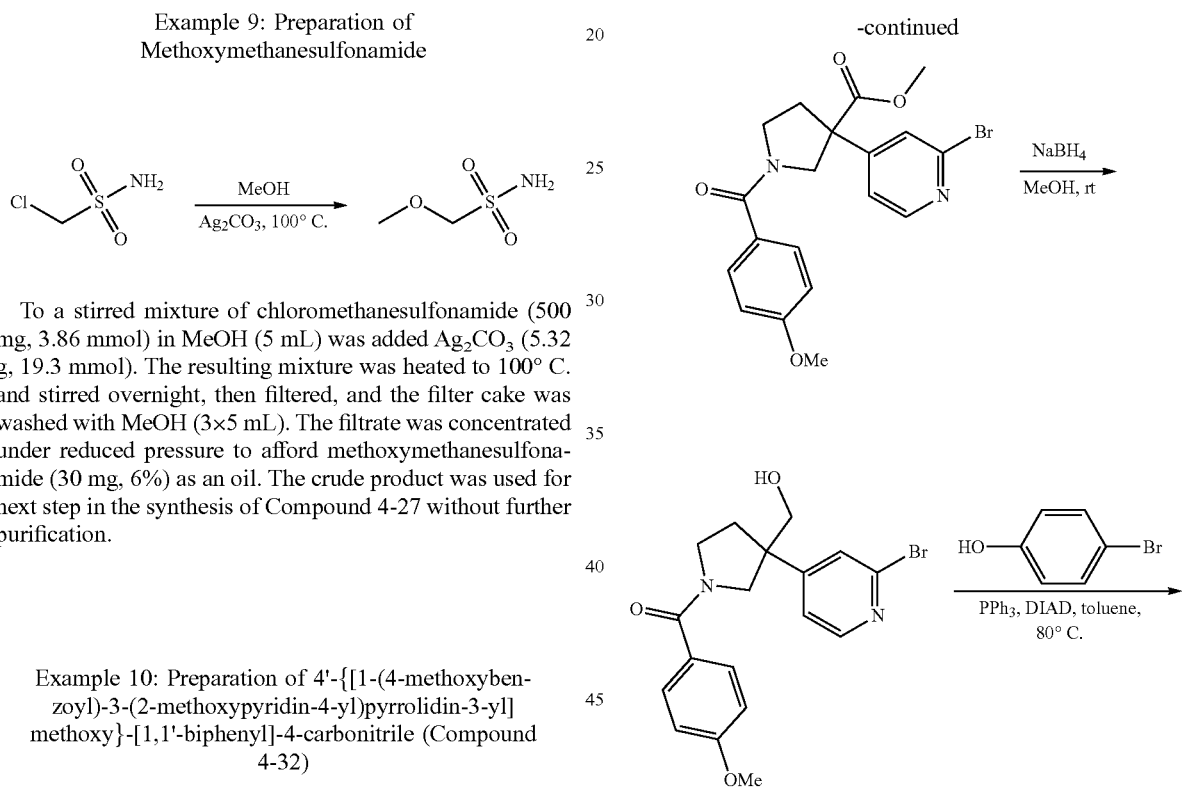

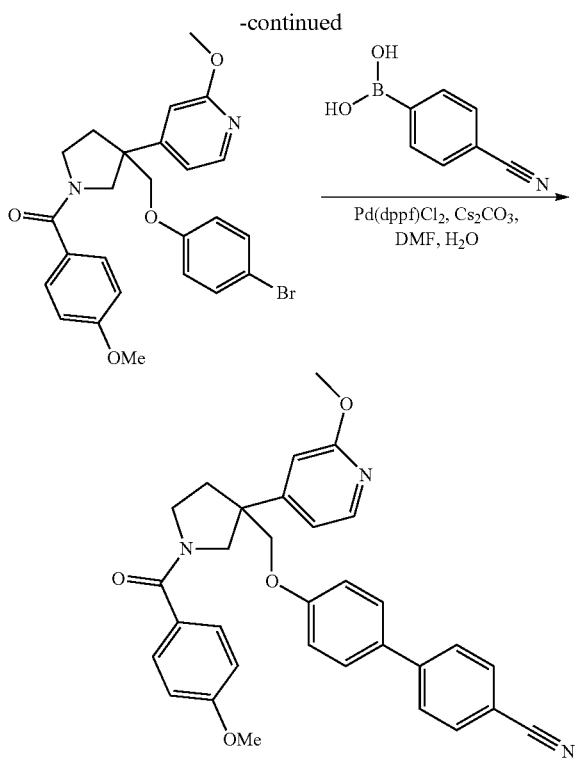

To a mixture of methyl 1-(4-methoxybenzoyl)pyrrolidine-3-carboxylate (500 mg, 1.9 mmol) and 2-bromopyridine-4-carbonitrile (420 mg, 2.28 mmol) in THF (10 mL) at −78° C. under an atmosphere of N₂ was added 1M KHMDS in THF (2.8 mL, 2.8 mmol) slowly. The mixture was warmed to rt and stirred for 2 h. The mixture was quenched by aq. NH₄Cl (15 mL) and extracted with DCM (10 mL×3). The combined organic layers were washed with brine (30 mL) and dried over MgSO₄. After filtration, the filtrate was concentrated under reduced pressure to afford methyl 3-(2-bromopyridin-4-yl)-1-(4-methoxybenzoyl)pyrrolidine-3-carboxylate (500 mg, crude) as a solid. The crude product was used for next step without further purification.

Step 2: Synthesis of [3-(2-bromopyridin-4-yl)-1-(4-methoxybenzoyl)pyrrolidin-3-yl]methanol To a mixture of methyl 3-(2-bromopyridin-4-yl)-1-(4-methoxybenzoyl)pyrrolidine-3-carboxylate (500 mg, 1.19 mmol) in MeOH (10 mL) was added NaBH₄ (135 mg, 3.58 mmol). The mixture was stirred at rt for 1 h, then purified by reverse flash chromatography with the following conditions: column, C18 silica gel; mobile phase, MeCN in Water (0.05% TFA), 20% to 70% gradient in 30 min; detector, UV 254 nm to afford [3-(2-bromopyridin-4-yl)-1-(4-methoxybenzoyl)pyrrolidin-3-yl]methanol (400 mg, 86%) as a solid.

Step 3: Synthesis of 2-bromo-4-[3-(4-bromophenoxymethyl)-1-(4-methoxybenzoyl)pyrrolidin-3-yl]pyridine To a mixture of [3-(2-bromopyridin-4-yl)-1-(4-methoxybenzoyl)pyrrolidin-3-yl]methanol (200 mg, 0.51 mmol), 4-bromophenol (97 mg, 0.56 mmol) and PPh₃ (335 mg, 1.28 mmol) in toluene (3 mL) under an atmosphere of N₂ was added DIAD (258 mg, 1.28 mmol). The mixture was heated to 80° C. and stirred for 2 h, then concentrated under reduced pressure and the residue was purified by reverse flash chromatography with the following conditions: column, C₁₈ silica gel; mobile phase, MeCN in Water (0.05% TFA), 20% to 80% gradient in 30 min; detector, UV 254 nm to afford 2-bromo-4-[3-(4-bromophenoxymethyl)-1-(4-methoxybenzoyl)pyrrolidin-3-yl]pyridine (100 mg, 36%) as a solid.

Step 4: Synthesis of 4-[3-(4-bromophenoxymethyl)-1-(4-methoxybenzoyl)pyrrolidin-3-yl]-2-methoxypyridine Na (85 mg, 3.7 mmol) was added to dry MeOH (2 mL) and was stirred at rt for 10 min. To the solution was added 2-bromo-4-[3-(4-bromophenoxymethyl)-1-(4-methoxybenzoyl)pyrrolidin-3-yl]pyridine (100 mg, 0.18 mmol). The mixture was heated to 80° C. and stirred for 4 h, then concentrated under reduced pressure and the residue was purified by reverse flash chromatography with the following conditions: column, C18 silica gel; mobile phase, MeCN in Water (0.05% TFA), 20% to 70% gradient in 30 min; detector, UV 254 nm to afford 4-[3-(4-bromophenoxymethyl)-1-(4-methoxybenzoyl)pyrrolidin-3-yl]-2-methoxypyridine (40 mg, 44%) as an oil.

Step 5: Synthesis of 4'-{[1-(4-methoxybenzoyl)-3-(2-methoxypyridin-4-yl)pyrrolidin-3-yl]methoxy}-[1,1'-biphenyl]-4-carbonitrile (Compound 4-32)

To a mixture of 4-[3-(4-bromophenoxymethyl)-1-(4-methoxybenzoyl)pyrrolidin-3-yl]-2-methoxypyridine (40 mg, 0.08 mmol) and 4-cyanophenylboronic acid (11 mg, 0.08 mmol) in DMF (2 mL) and H₂O (0.4 mL) under an atmosphere of N₂ was added Cs₂CO₃ (52 mg, 0.160 mmol) and Pd(dppf)Cl₂ (5 mg, 0.008 mmol). The mixture was heated to 80° C. and stirred for 3 h, then filtered, and the filtrate was purified by preparative-HPLC with the following conditions (Column: XBridge Prep Phenyl OBD Column, 19*150 mm, 5 μm; Mobile Phase A: Water(10 mmol/L NH₄HCO₃+0.1% NH₃·H₂O), Mobile Phase B: ACN; Flow rate: 25 mL/min; Gradient: 52% B to 82% B in 7 min, 82% B; Wave Length: 254 nm; RT1(min): 5; Number Of Runs: 0) to afford 4'-{[1-(4-methoxybenzoyl)-3-(2-methoxypyridin-4-yl)pyrrolidin-3-yl]methoxy}-[1,1'-biphenyl]-4-carbonitrile (6.8 mg, 16%) as a solid. LC/MS: mass calcd. For C₃₂H₂₉N₃O₄: 519.2, found: 520.2[M+H]⁺; ¹H NMR (300 MHz, CD₃OD) δ 8.05-8.12 (m, 1H), 7.76 (s, 4H), 7.50-7.67 (m, 4H), 6.75-7.14 (m, 6H), 4.08-4.38 (m, 3H), 3.95-4.00 (m, 1H), 3.83-3.95 (m, 7H), 3.68-3.71 (m, 1H), 2.51-2.60 (m, 1H), 2.34-2.51 (m, 1H).

Example 11: Preparation of 4'-{[1-(4-methoxybenzoyl)-3-(2-oxo-1H-pyridin-4-yl)pyrrolidin-3-yl]methoxy}-[1,1'-biphenyl]-4-carbonitrile (Compound 4-16)

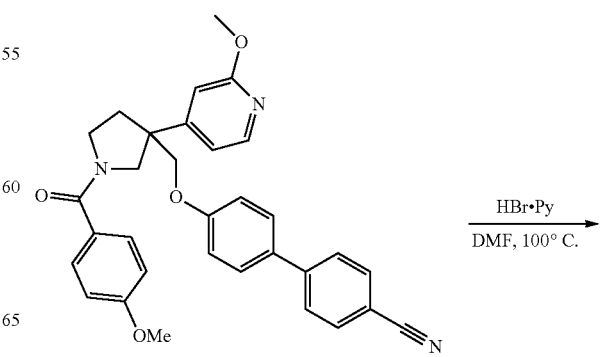

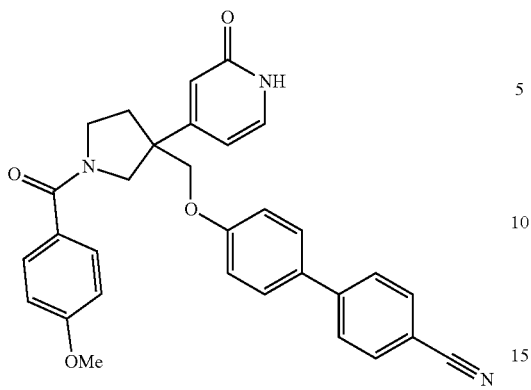

To a mixture of 4'-{[1-(4-methoxybenzoyl)-3-(2-methoxypyridin-4-yl)pyrrolidin-3-yl]methoxy}-[1,1'-biphenyl]-4-carbonitrile (30 mg, 0.06 mmol) in DMF (1 mL) was added pyridine hydrobromide (55 mg, 0.35 mmol). The mixture was heated to 100° C. and stirred for 2 h, then purified by preparative-HPLC with the following conditions (Column: XBridge Prep Phenyl OBD Column, 19*250 mm, 5 μm; Mobile Phase A: Water(10 mmol/L NH$_4$HCO3+0.1% NH$_3$·H$_2$O), Mobile Phase B: ACN; Flow rate: 25 mL/min; Gradient: 40% B to 70% B in 7 min, 70% B; Wave Length: 254 nm; RT1(min): 6; Number Of Runs: 0) to afford 4'-{[1-(4-methoxybenzoyl)-3-(2-oxo-1H-pyridin-4-yl)pyrrolidin-3-yl]methoxy}-[1,1'-biphenyl]-4-carbonitrile (13.6 mg, 47%) as a solid. LC/MS: mass calcd. For C$_{31}$H$_{27}$N$_3$O$_4$: 505.2, found: 506.2 [M+H]$^+$; $^1$H NMR (300 MHz, CD$_3$OD) δ 7.77 (s, 4H), 7.59-7.69 (m, 4H), 7.38-7.44 (m, 1H), 6.93-7.12 (m, 4H), 6.50-6.60 (m, 1H), 6.42-6.52 (m, 1H), 4.24-4.39 (m, 1H), 4.03-4.18 (m, 2H), 3.90-3.98 (m, 1H), 3.86 (s, 4H), 3.62-3.71 (m, 1H), 2.49-3.59 (m, 1H), 2.21-2.37 (m, 1H).

Example 12: Preparation of 1-[1-(4-bromophenyl)-2,2,2-trifluoroethyl]-3-[({4'-cyano-[1,1'-biphenyl]-4-yl}oxy)methyl]pyrrolidine-3-carboxylic acid (Compound 4-34)

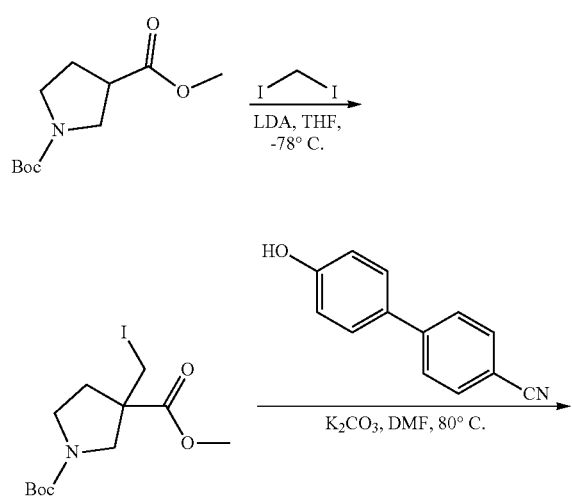

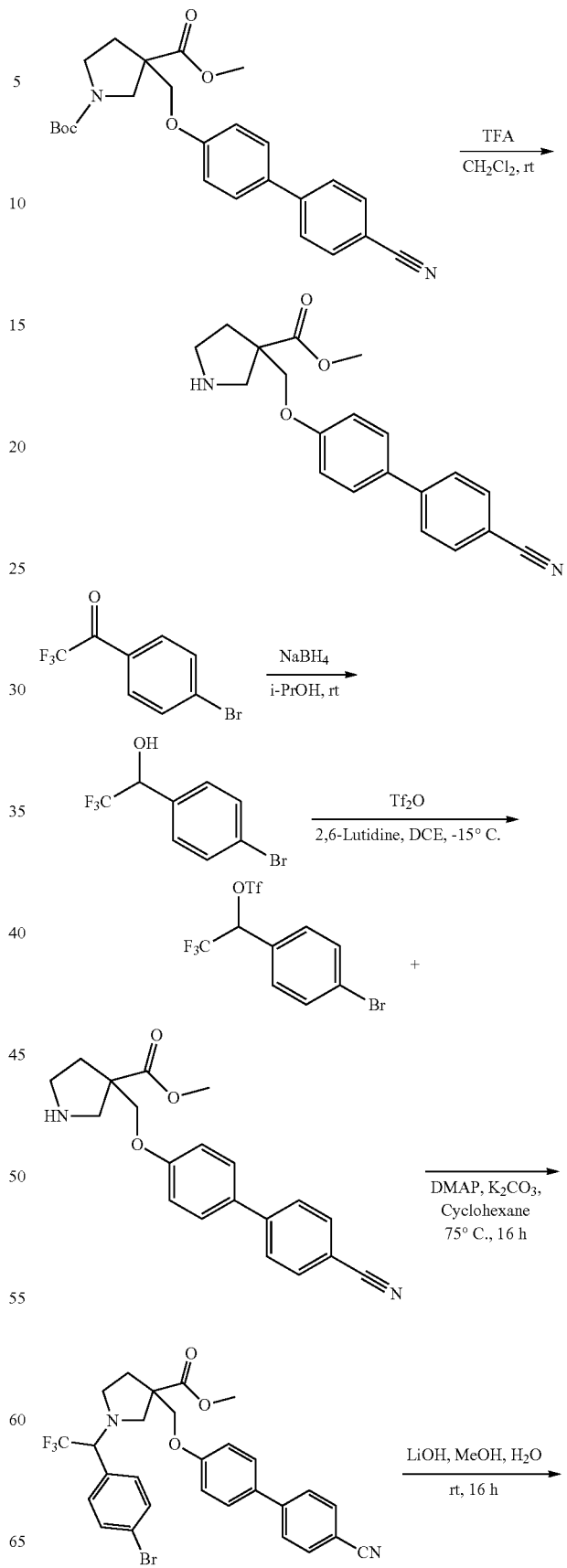

-continued

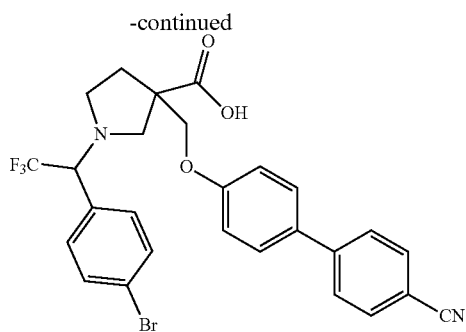

Step 1: Synthesis of 1-tert-butyl 3-methyl 3-(iodomethyl)pyrrolidine-1,3-dicarboxylate To a mixture of 1-tert-butyl 3-methyl pyrrolidine-1,3-dicarboxylate (2.0 g, 8.7 mmol) in THF (100 mL) at −78° C. under an atmosphere of $N_2$ was added 2M LDA in THF (6.5 mL, 13.0 mmol) dropwise. The mixture was stirred at −78° C. for 1 h, the $CH_2I_2$ (3.04 g, 11.3 mmol) was added at −78° C. The mixture was warmed to rt and stirred for 1 h, then $H_2O$ (100 mL) added and the mixture was extracted by EtOAc (80 mL×3). The combined organic layers were washed with brine, dried over $Na_2SO_4$, filtered and concentrated to afford 1-tert-butyl 3-methyl 3-(iodomethyl)pyrrolidine-1,3-dicarboxylate (2 g, 62%) as an oil.

Step 2: Synthesis of 1-tert-butyl 3-methyl 3-[({4'-cyano-[1,1'-biphenyl]-4-yl}oxy)methyl]pyrrolidine-1,3-dicarboxylate To a mixture of 1-tert-butyl 3-methyl 3-(iodomethyl)pyrrolidine-1,3-dicarboxylate (2.0 g, 5.4 mmol) and 4'-hydroxy-[1,1'-biphenyl]-4-carbonitrile (1.59 g, 8.125 mmol) in DMF (50 mL) was added $K_2CO_3$ (1.5 g, 10.86 mmol). The mixture was heated to 80° C. and stirred for 16 h. The mixture was filtered, and the filter cake was washed with EtOAc (50 mL). The filtrate was washed with $H_2O$ (100 mL) and the aqueous layer extracted with EtOAc (80 mL×3). The combined organic layers were washed with brine (150 mL), dried over $Na_2SO_4$, filtered and concentrated to afford 1-tert-butyl 3-methyl 3-[({4'-cyano-[1,1'-biphenyl]-4-yl}oxy)methyl]pyrrolidine-1,3-dicarboxylate (2.0 g, 85%) as an oil.

Step 3: Synthesis of Methyl 3-[({4'-cyano-[1,1'-biphenyl]-4-yl}oxy)methyl]pyrrolidine-3-carboxylate To a mixture of 1-tert-butyl 3-methyl 3-[({4'-cyano-[1,1'-biphenyl]-4-yl}oxy)methyl]pyrrolidine-1,3-dicarboxylate (3.0 g, 6.9 mmol) in DCM (50 mL) was added TFA (10 mL). The mixture was stirred at rt for 1 h, then concentrated under reduced pressure and the residue was purified by reverse column chromatography with the following conditions: column, C18 silica gel; mobile phase, MeCN in Water (0.05% TFA), 30% to 80% gradient in 30 min; detector, UV 254 nm to afford methyl 3-[({4'-cyano-[1,1'-biphenyl]-4-yl}oxy)methyl]pyrrolidine-3-carboxylate (1.2 g, 52%) as an oil.

Step 4: Synthesis of 1-(4-bromophenyl)-2,2,2-trifluoroethanol

To a mixture of 1-(4-bromophenyl)-2,2,2-trifluoroethanone (500 mg, 2.0 mmol) in i-PrOH (10 mL) was added $NaBH_4$ (150 mg, 3.95 mmol). The mixture was quenched with 1M HCl (15 mL) and extracted with MTBE (10 mL×3). The combined organic layers were dried over $Na_2SO_4$, filtered and concentrated to afford 1-(4-bromophenyl)-2,2,2-trifluoroethanol (200 mg, 40%) as an oil.

Step 5: Synthesis of 1-(4-bromophenyl)-2,2,2-trifluoroethyl trifluoromethanesulfonate To a mixture of 1-(4-bromophenyl)-2,2,2-trifluoroethanol (30 mg, 0.12 mmol) and 2,6-lutidine (18 mg, 0.18 mmol) in DCE (1 mL) at −15° C. was added $Tf_2O$ (50 mg, 0.18 mmol). The mixture was warmed to rt and stirred for 1 h, then diluted with DCM (5 mL) and washed with $H_2O$ (5 mL), 1M HCl (5 mL) and brine (5 mL). The organic layer was dried over $Na_2SO_4$, filtered and concentrated under reduced pressure to afford 1-(4-bromophenyl)-2,2,2-trifluoroethyl trifluoromethanesulfonate (30 mg, 66%) as an oil.

Step 6: Synthesis of methyl 1-[1-(4-bromophenyl)-2,2,2-trifluoroethyl]-3-[({4'-cyano-[1,1'-biphenyl]-4-yl}oxy)methyl]pyrrolidine-3-carboxylate To a mixture of methyl 3-[({4'-cyano-[1,1'-biphenyl]-4-yl}oxy)methyl]pyrrolidine-3-carboxylate (200 mg, 0.6 mmol) and 1-(4-bromophenyl)-2,2,2-trifluoroethyl trifluoromethanesulfonate (690 mg, 1.79 mmol) in cyclohexane (5 mL) was added DMAP (72 mg, 0.6 mmol) and $K_2CO_3$ (164 mg, 1.19 mmol). The mixture was warmed to 75° C. and stirred for 16 h, then diluted with DCM (10 mL) and washed with brine (10 mL), dried over $Na_2SO_4$, filtered and concentrated under reduced pressure. The residue was purified by reverse flash chromatography with the following conditions: column, C18 silica gel; mobile phase, MeCN in Water (0.05% TFA), 50% to 100% gradient in 20 min; detector, UV 254 nm to afford methyl 1-[1-(4-bromophenyl)-2,2,2-trifluoroethyl]-3-[({4'-cyano-[1,1'-biphenyl]-4-yl}oxy)methyl]pyrrolidine-3-carboxylate (40 mg, 12%) as an oil.

Step 7: Synthesis of 1-[1-(4-bromophenyl)-2,2,2-trifluoroethyl]-3-[({4'-cyano-[1,1'-biphenyl]-4-yl}oxy)methyl]pyrrolidine-3-carboxylic acid (Compound 4-34)

To a mixture of methyl 1-[1-(4-bromophenyl)-2,2,2-trifluoroethyl]-3-[({4'-cyano-[1,1'-biphenyl]-4-yl}oxy)methyl]pyrrolidine-3-carboxylate (30 mg, 0.05 mmol) in MeOH (1 mL) was added 2 M aq. LiOH (0.5 mL). The mixture was stirred at rt for 16 h, then concentrated under reduced pressure and the residue was purified by preparative-HPLC with the following conditions (Column: Xselect CSH C18 OBD Column 30*150 mm 5 μm, n; Mobile Phase A: Water(0.1% FA), Mobile Phase B: ACN; Flow rate: 60 mL/min; Gradient: 70% B to 90% B in 7 min, 90% B; Wave Length: 254 nm; RT1(min): 5.87; Number Of Runs: 0) to afford 1-[1-(4-bromophenyl)-2,2,2-trifluoroethyl]-3-[({4'-cyano-[1,1'-biphenyl]-4-yl}oxy)methyl]pyrrolidine-3-carboxylic acid (1.2 mg, 4%) as a solid. LC/MS: mass calcd. For $C_{27}H_{22}BrF_3N_2O_3$: 558.0, found: 559.0 [M+H]$^+$; $^1$H NMR (300 MHz, $CD_3OD$) δ 7.79 (d, J=3.0 Hz, 4H), 7.54-7.67 (m, 4H), 7.44-7.50 (m, 2H), 6.99-7.10 (m, 2H), 4.36-4.45 (m, 1H), 4.20-4.26 (m, 2H), 3.18-3.33 (m, 1H), 3.01-3.12 (m, 1H), 2.78-3.00 (m, 2H), 2.30-2.38 (m, 1H), 1.95-2.05 (m, 1H); $^{19}$F NMR (282 MHz, $CD_3OD$) δ −69.8.

Example 13: Preparation of 3-[({4'-cyano-[1,1'-biphenyl]-4-yl}oxy)methyl]-1-[2,2,2-trifluoro-1-(4-methoxyphenyl)ethyl]pyrrolidine-3-carboxylic acid; trifluoroacetic acid (Compound 4-1)

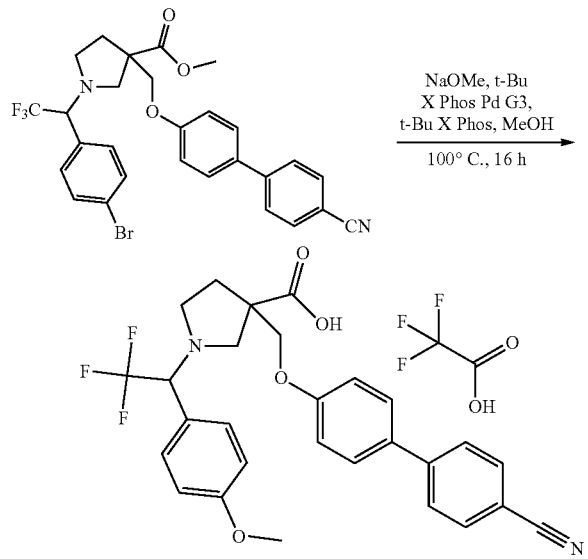

To a mixture of methyl 1-[1-(4-bromophenyl)-2,2,2-trifluoroethyl]-3-[({4'-cyano-[1,1'-biphenyl]-4-yl}oxy)methyl]pyrrolidine-3-carboxylate (25 mg, 0.044 mmol) in MeOH (1 mL) under an atmosphere of $N_2$ was added NaOMe (5 mg, 0.09 mmol), di-tert-butyl[2',4',6'-tris(propan-2-yl)-[1,1'-biphenyl]-2-yl]phosphane; {2'-amino-[1,1'-biphenyl]-2-yl}palladio methanesulfonate (4 mg, 0.004 mmol) and di-tert-butyl[2',4',6'-tris(propan-2-yl)-[1,1'-biphenyl]-2-yl]phosphane (2 mg, 0.004 mmol). The mixture was heated to 100° C. and stirred for 16 h, then filtered and the filtrate was concentrated under reduced pressure and the residue was purified by preparative-HPLC (Column: XBridge Prep OBD C18 Column, 19*250 mm, 5 μm; Mobile Phase A: Water (0.05% TFA), Mobile Phase B: ACN; Flow rate: 25 mL/min; Gradient: 50% B to 80% B in 7 min, 80% B; Wave Length: 254 nm; RT1(min): 6; Number Of Runs: 0) to afford 3-[({4'-cyano-[1,1'-biphenyl]-4-yl}oxy)methyl]-1-[2,2,2-trifluoro-1-(4-methoxyphenyl)ethyl]pyrrolidin-3-carboxylic acid; trifluoroacetic acid (2.6 mg, 10%) as a solid. LC/MS: mass calcd. For $C_{30}H_{26}F_6N_2O_6$: 510.1, found: 511.2[M+ H]$^+$; $^1$H NMR (300 MHz, DMSO-$d_6$) δ 7.80-7.93 (m, 4H), 7.65-7.75 (m, 2H), 7.25-7.40 (m, 2H), 7.01-7.13 (m, 2H), 6.90-7.00 (m, 2H), 4.22-4.37 (m, 1H), 4.12 (s, 2H), 3.77 (d, J=3.0 Hz, 3H), 2.56-3.05 (m, 4H), 2.12-2.25 (m, 1H), 1.77-1.93 (m, 1H); $^{19}$F NMR (282 MHz, DMSO-$d_6$) δ −68.1, −74.0.

BIOLOGY EXAMPLES

Example B1: EP2 Potency Assay

Compounds of the present disclosure are EP2 antagonists with half-max inhibitory concentration ($IC_{50}$) values below 25 μM. Compound potency was measured using a cAMP TR-FRET assay.

CHO-K1 cells (ATCC) were seeded at a density of 9.75×10$^5$ in 6 cm plates, and then on the following day cell media was changed to Opti-Mem I reduced serum media (Gibco), and transfected with a plasmid for expression of the EP2 receptor (the target receptor of interest), using the FuGENE 6 Transfection reagent (Promega). After 6 hours incubation, the cell media was replaced with F12 medium supplemented with 10% FBS and 100 U/ml Pen-Strep. 24 hours after transfection, cells were harvested and seeded at a density of 3000 cells/well in a 384 well plate to perform the cAMP assay, using the LANCE Ultra cAMP assay kit (PerkinElmer).

For each test compound of interest, 10 nl/well of serially diluted test compound was added to each well, resulting in a range of 10 serially diluted compound concentrations from 10000 nM to 0.038 nM, with duplicate wells for each concentration. Plates were then centrifuged at 1000 rpm for 1 min, agitated at 600 rpm at R.T. for 2 min, and incubated at 25° C. for 5 min. The reference agonist, prostaglandin E2 (MCE), was added to each well at the appropriate concentration to reach its EC80 value. Plates were then centrifuged at 1000 rpm for 1 min, agitated at 600 rpm at R.T. for 2 min, and incubated at 25° C. for 30 min.

To measure levels of cAMP, 5 μl/well of Eu-cAMP working solution and 5 μl/well of Ulight-anti-cAMP working solution were added to each well, and plate was centrifuged at 1000 rpm for 1 min, agitated at 600 rpm at R.T. for 2 min, and incubated at 25° C. for 15 min. Levels of TR-FRET fluorescence were measured in each well using an EnVision microplate reader (excitation wavelength=337 nm and emission wavelength=615 and 665 nm). A dose-response curve was prepared by plotting percent inhibition for each compound concentration, and then IC50 was calculated by fitting a curve to the plotted values and extrapolating the IC50 concentration.

The potency for compounds disclosed herein are as shown in Table B1. Potency data is grouped into categories of AA ($IC_{50}$<100 nM); A ($IC_{50}$=100 to 500 nM); B ($IC_{50}$=500 nM to 1 μM); C ($IC_{50}$=1 μM to 5 μM); and D ($IC_{50}$>5 μM).

TABLE B1

| EP2 Potency | |
|---|---|
| ID No. | Potency |
| 4-21 | C |
| 4-20 | D |
| 4-13 | C |
| 4-23 | D |
| 4-22 | C |
| 4-19 | AA |
| 4-24 | A |
| 4-25 | B |
| 4-26 | C |
| 4-27 | A |
| 4-28 | B |
| 4-29 | D |
| 4-30 | C |
| 4-31 | D |
| 2-2 | B |
| 4-16 | D |
| 4-1 | D |
| 4-34 | D |

Example B2: Stability Assays (a) Human Liver Microsome Stability

The tested compound was incubated in duplicate with human liver microsomes (0.5 mg/mL) at 37° C. These incubations were carried out at a final test article concentration of 2 μM over a total incubation period of 60 minutes.

Samples were taken at 0, 15, 30, 45 and 60 min and the reaction terminated by addition of 4 volumes of acetonitrile containing internal standard (100 nM alprazolam, 200 nM imipramine, 200 nM labetalol and 2 μM ketoprofen). Diclofenac was used as a positive control in this study. The samples were analyzed by UPLC-MS/MS to determine the concentration of the test compound and the percent remaining, intrinsic clearance (in vitro $CL_{int}$) and half-life ($t_{1/2}$) values were calculated.

Chromatographic analyses were performed on a Shimadzu UPLC apparatus (Kyoto, Japan) consisting of a gradient pump (model LC-30AD), an automatic injector (model HTC PAL System) and an on-line degasser (model DGU-20A5R). Detection was a triple quadrupole tandem mass spectrometer equipped with a turbo ion spray interface (API 4000/Triple Quad 4500/Triple Quad 5500/Triple Quad 6500). Data acquisition and integration were carried out with LC-MS software (Analyst 1.6) linked directly to the LC-MS/MS system. Chromatographic separations were achieved on a XSelect Hss T3 2.5μ (2.1×30 mm) Column. The mobile phase was 0.1% formic acid in water (A) and 0.1% formic acid in acetonitrile (B). The flow rate was 1.0 mL/min and column was maintained at 40° C.

(b) Human Hepatocyte Stability

The tested compound was incubated in duplicate with incubation media (Williams' Medium E with 1× GlutaMAX) containing human hepatocytes (0.5×10⁶ cells/mL). These incubations were carried out at a final test concentration of 1 μM over a total incubation period of 120 minutes. Samples were taken at 0, 15, 30, 60, 90 and 120 min and the reaction was terminated by addition of acetonitrile containing internal standard (100 nM alprazolam, 200 nM labetalol, 200 nM caffeine and 200 nM diclofenac). Verapamil was used as the positive control in this study. The samples were analyzed by UPLC-MS/MS to determine the concentration of the tested compound and the percentage remaining, intrinsic clearance (in vitro $CL_{int}$) and half-life (t1/2) values were calculated.

Chromatographic analyses were performed on a Shimadzu UPLC apparatus (Kyoto, Japan) consisting of a gradient pump (model LC-30AD), an automatic injector (model HTC PAL System) and an on-line degasser (model DGU-20A5R). Detection was a triple quadrupole tandem mass spectrometer equipped with a turbo ion spray interface (API 4000/Triple Quad 4500/Triple Quad 5500/Triple Quad 6500). Data acquisition and integration were carried out with LC-MS software (Analyst 1.6) linked directly to the LC-MS/MS system. Chromatographic separations were achieved on a XSelect Hss T3 2.5μ (2.1×30 mm) Column. The mobile phase was 0.1% formic acid in water (A) and 0.1% formic acid in acetonitrile (B). The flow rate was 1.0 mL/min and column was maintained at 40° C.

The stability data for compounds disclosed herein are as shown in Table B2.

Half-life ($T_{1/2}$) data is measured in minutes, and in Table B2, in both microsomal and hepatic assays, the data is grouped into categories of:

A $T_{1/2}$=1000+

B $T_{1/2}$=500 to 1000

C $T_{1/2}$=100 to 500

D $T_{1/2}$<100

In vitro clearance ($CL_{int}$) data is measured in μL/min/mg prot, and in Table B2, in both microsomal and hepatic assays, the data is grouped into categories of:

A $CL_{int}$<1

B $CL_{int}$=1 to 10

C $CL_{int}$=10 to 20

D $CL_{int}$=20+

TABLE B2

| | Microsomal and hepatic stability | | | |
|---|---|---|---|---|
| ID No. | $T_{1/2}$ (microsomal) | in vitro $CL_{int}$ (microsomal) | $T_{1/2}$ (hepatic) | in vitro $CL_{int}$ (hepatic) |
| 1-2 | C | B | — | — |
| 1-3 | D | D | — | — |
| 2-2 | B | B | — | — |
| 2-3 | D | D | — | — |
| 4-19 | A | A | A | A |
| 4-24 | C | B | B | B |
| Ref | B | B | C | B |

The reference compound ("Ref") of Table B2 is PF-04852946, which has the structure:

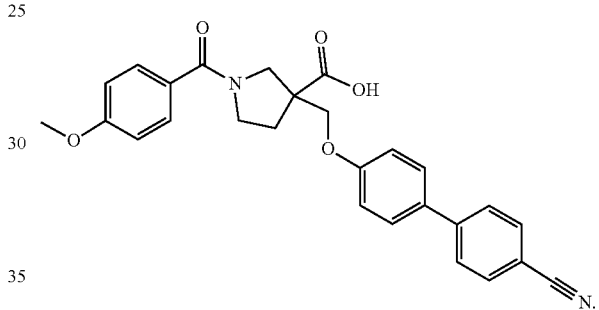

COMPOSITION EXAMPLES

Example C1: Parenteral Pharmaceutical Composition

To prepare a parenteral pharmaceutical composition suitable for administration by injection (subcutaneous, intravenous, and the like), 100 mg of a water-soluble salt of a compound disclosed herein, or a pharmaceutically acceptable salt or solvate thereof, is dissolved in sterile water and then mixed with 10 mL of 0.9% sterile saline. The mixture is incorporated into a dosage unit form suitable for administration by injection Example C2: Oral Pharmaceutical Composition To prepare a pharmaceutical composition for oral delivery, 100 mg of a compound disclosed herein, or a pharmaceutically acceptable salt or solvate thereof, is mixed with 750 mg of starch. The mixture is incorporated into an oral dosage unit for, such as a hard gelatin capsule, which is suitable for oral administration.

Example C3: Topical Gel Pharmaceutical Composition

To prepare a pharmaceutical topical gel composition, 100 mg of a compound disclosed herein, or a pharmaceutically acceptable salt or solvate thereof, is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example C4: Ophthalmic Solution

To prepare a pharmaceutical opthalmic solution composition, 100 mg of a compound disclosed herein, or a pharmaceutically acceptable salt or solvate thereof, is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and various modifications or changes suggested to persons skilled in the art are to be included within the spirit and purview of this application and scope of the appended claims.

What is claimed is:

1. A compound having the structure of Formula (I):

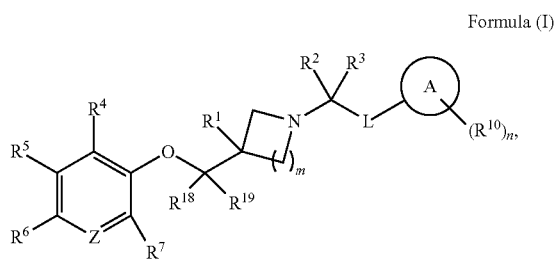

Formula (I)

or a pharmaceutically acceptable salt, or solvate thereof; wherein:
  $R^1$ is —C(O)NR$^d$R$^e$;
  $R^d$ is —CN, $C_1$-$C_6$ alkyl, $C_1$-$C_6$ deuteroalkyl, $C_1$-$C_6$ fluoroalkyl, $C_{1-6}$ alkoxy, substituted or unsubstituted $C_3$-$C_6$ cycloalkyl, substituted or unsubstituted $C_2$-$C_6$ heterocycloalkyl, —OH, OR$^{1d}$, —SOR$^{1d}$, or —SO$_2$R$^{1d}$; wherein R$^{1d}$ is substituted or unsubstituted $C_1$-$C_6$ alkyl, substituted or unsubstituted $C_3$-$C_6$ cycloalkyl, substituted or unsubstituted 3- to 6-membered heterocycloalkyl, substituted or unsubstituted phenyl, or substituted or unsubstituted 5- to 6-membered heteroaryl; wherein if R$^{1d}$ is substituted then it is substituted with one or more R$^{14}$;
  $R^e$ is hydrogen, $C_1$-$C_6$ alkyl, $C_1$-$C_6$ deuteroalkyl, $C_1$-$C_6$ fluoroalkyl, $C_{1-6}$ alkoxy, substituted or unsubstituted $C_3$-$C_6$ cycloalkyl, or substituted or unsubstituted $C_2$-$C_6$ heterocycloalkyl;
  or $R^d$ and $R^e$ are taken together with the N atom to which they are attached to form a substituted or unsubstituted $C_2$-$C_6$ heterocycloalkyl;
  $R^2$ is hydrogen, $C_1$-$C_6$ alkyl, $C_1$-$C_6$ deuteroalkyl, or $C_1$-$C_6$fluoroalkyl;
  $R^3$ is hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, or substituted or unsubstituted $C_2$-$C_6$ heterocycloalkyl;
  or $R^2$ and $R^3$ are taken together with the carbon atom to which they are attached to form a carbonyl (C=O) or thiocarbonyl (C=S);
  or $R^2$ and $R^3$ are taken together with the carbon atom to which they are attached to form a ring B that is a substituted or unsubstituted $C_3$-$C_6$ cycloalkyl, or substituted or unsubstituted $C_2$-$C_6$ heterocycloalkyl, wherein if the ring B is substituted then it is substituted with one or more R$^{12}$;
  Z is N or CR$^8$;
  L is absent or —NH—;
  $R^4$, $R^5$, $R^7$, and $R^8$ are each independently hydrogen, halogen, —CN, $C_1$-$C_6$ alkyl, $C_1$-$C_6$ deuteroalkyl, $C_1$-$C_6$ fluoroalkyl, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$;
  $R^6$ is hydrogen, halogen, —CN, $C_1$-$C_6$ alkyl, $C_1$-$C_6$ deuteroalkyl, $C_1$-$C_6$ fluoroalkyl, —OR$^{16}$, —C(=O)R$^{16}$, —CO$_2$R$^{16}$, —C(=O)N(R$^{16}$)$_2$, —N(R$^{16}$)$_2$, —NR$^{16}$C(=O)R$^{16}$, substituted or unsubstituted $C_3$-$C_6$ cycloalkyl, substituted or unsubstituted $C_2$-$C_6$heterocycloalkyl, substituted or unsubstituted phenyl, or substituted or unsubstituted heteroaryl; wherein if $R^6$ is substituted then it is substituted with one or more R$^{13}$;
  ring A is a substituted or unsubstituted phenyl, or substituted or unsubstituted heteroaryl;
  each $R^9$, $R^{10}$, $R^{11}$, $R^{12}$, $R^{13}$, and $R^{14}$ is independently hydrogen, deuterium, halogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, —CN, —OR$^{16}$, —C(=O)R$^{16}$, —CO$_2$R$^{16}$, —C(=O)N(R$^{16}$)$_2$, —N(R$^{16}$)$_2$, or —NR$^{16}$C(=O)R$^{16}$;
  each $R^{16}$ is independently hydrogen, $C_1$-$C_6$ alkyl, $C_1$-$C_6$ deuteroalkyl, $C_1$-$C_6$ fluoroalkyl, substituted or unsubstituted $C_3$-$C_6$ cycloalkyl, substituted or unsubstituted $C_2$-$C_6$ heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted $C_3$-$C_6$cycloalkyl), -alkyl-(substituted or unsubstituted $C_2$-$C_6$ heterocycloalkyl);
  or both $R^{16}$ are taken together with the N atom to which they are attached to form a substituted or unsubstituted $C_2$-$C_6$ heterocycloalkyl;
  $R^{18}$ and $R^{19}$ are each independently hydrogen, deuterium, $C_1$-$C_6$ alkyl, $C_1$-$C_6$ deuteroalkyl, or $C_1$-$C_6$fluoroalkyl;
  or $R^{18}$ and $R^{19}$ are taken together with the carbon atom to which they are attached to form a ring E that is a $C_3$-$C_6$cycloalky, or $C_2$-$C_6$ heterocycloalkyl;
  m is 1 or 2; and
  n is 0, 1, 2, 3, or 4.

2. The compound of claim 1, or a pharmaceutically acceptable salt, or solvate thereof, wherein ring A is an unsubstituted or substituted phenyl, unsubstituted or substituted pyridinyl, unsubstituted or substituted pyrimidinyl, unsubstituted or substituted pyrazinyl, unsubstituted or substituted pyridazinyl, or unsubstituted or substituted triazinyl.

3. The compound of claim 1, or a pharmaceutically acceptable salt, or solvate thereof, wherein ring A is an unsubstituted or substituted phenyl, or unsubstituted or substituted pyridinyl.

4. The compound of claim 1, or a pharmaceutically acceptable salt, or solvate thereof, wherein:

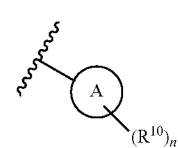

is

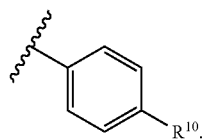

5. The compound of claim 1, or a pharmaceutically acceptable salt, or solvate thereof, having the structure of Formula (II):

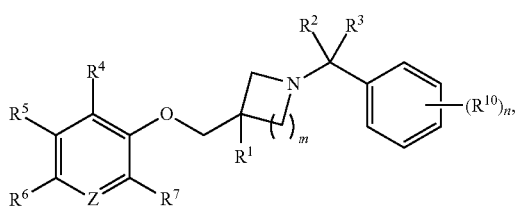

Formula (II)

or a pharmaceutically acceptable salt or solvate thereof.

6. The compound of claim 1, or a pharmaceutically acceptable salt, or solvate thereof, having the structure of Formula (III):

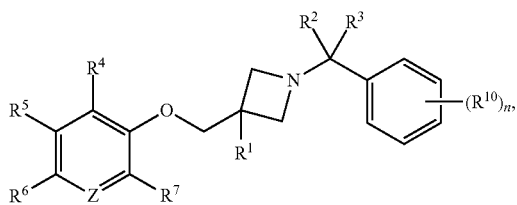

Formula (III)

or a pharmaceutically acceptable salt or solvate thereof.

7. The compound of claim 1, or a pharmaceutically acceptable salt, or solvate thereof, having the structure of Formula (IV):

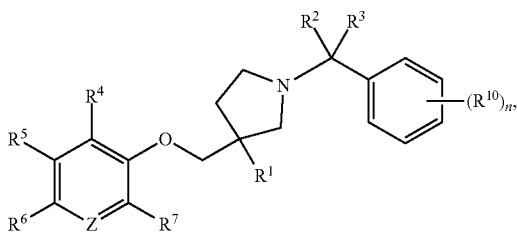

Formula (IV)

or a pharmaceutically acceptable salt or solvate thereof.

8. The compound of claim 1, or a pharmaceutically acceptable salt, or solvate thereof, wherein:
each $R^{10}$ is independently hydrogen, deuterium, substituted or unsubstituted $C_3$-$C_6$ cycloalkyl, F, Cl, Br, —CN, —CH$_3$, —CH$_2$CH$_3$, —(CH$_2$)$_2$CH$_3$, —(CH$_2$)$_3$CH$_3$, —CH(CH$_3$)$_2$, —C(CH$_3$)$_3$, —CH$_2$F, —CHF$_2$, —CF$_3$, —CH$_2$CF$_3$, —CH$_2$D, —CHD$_2$, —CD$_3$, —OH, —OCH$_3$, —OCH$_2$CH$_3$, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, or —N(CH$_3$)$_2$.

9. The compound of claim 1, or a pharmaceutically acceptable salt, or solvate thereof, wherein:

$R^1$ is —C(O)NR$^d$R$^e$;

$R^d$ is —CN, $C_1$-$C_6$ alkyl, $C_1$-$C_6$ fluoroalkyl, —OH, —OCH$_3$, or —SO$_2$R$^{1d}$; and $R^e$ is hydrogen or —CH$_3$.

10. The compound of claim 1, or a pharmaceutically acceptable salt, or solvate thereof, wherein:

$R^1$ is —C(O)NHSO$_2$R$^{1d}$; and $R^{1d}$ is substituted or unsubstituted $C_1$-$C_6$ alkyl, substituted or unsubstituted $C_3$-$C_6$ cycloalkyl, substituted or unsubstituted 3- to 6-membered heterocycloalkyl, substituted or unsubstituted phenyl, or substituted or unsubstituted 5- to 6-membered heteroaryl; wherein if $R^{1d}$ is substituted then it is substituted with one or more $R^{14}$.

11. The compound of claim 10, or a pharmaceutically acceptable salt, or solvate thereof, wherein $R^{1d}$ is substituted or unsubstituted $C_1$-$C_6$ alkyl.

12. The compound of claim 10, or a pharmaceutically acceptable salt, or solvate thereof, wherein $R^{1d}$ is substituted or unsubstituted $C_1$-$C_6$ alkyl, substituted or unsubstituted cyclopropyl, or substituted or unsubstituted phenyl.

13. The compound of claim 1, having the structure:

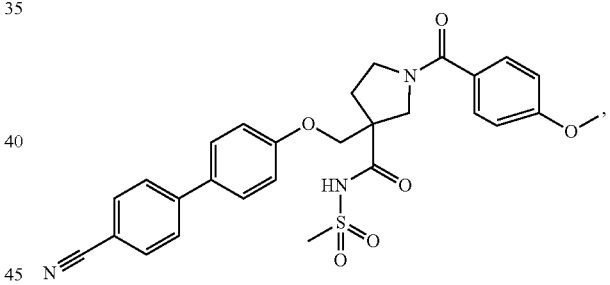

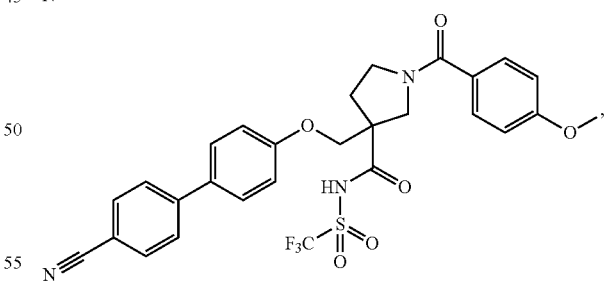

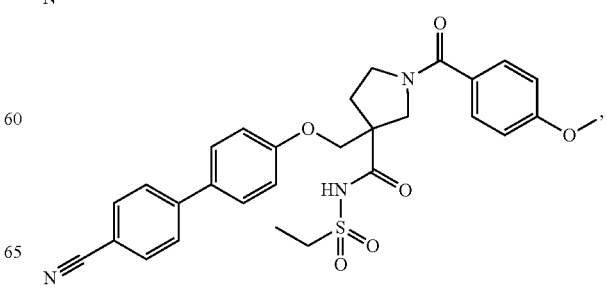

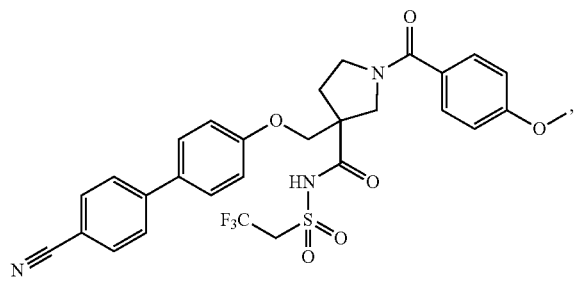

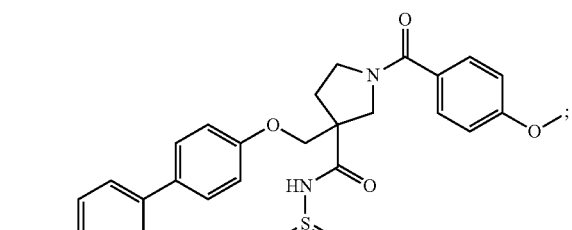

or a pharmaceutically acceptable salt, or solvate thereof.

14. The compound of claim 1, or a pharmaceutically acceptable salt, or solvate thereof, wherein:

$R^2$ is hydrogen, —CH$_3$, —CH$_2$CH$_3$, -CD$_3$, —CH$_2$CD$_3$, —CF$_3$, or —CH$_2$CF$_3$;

$R^3$ is hydrogen, —CH$_3$, —CH$_2$CH$_3$, -CD$_3$, —CH$_2$CD$_3$, —CF$_3$, or —CH$_2$CF$_3$; or or $R^2$ and $R^3$ are taken together with the carbon atom to which they are attached to form a carbonyl (C=O).

15. The compound of claim 1, or a pharmaceutically acceptable salt, or solvate thereof, wherein:

Z is CH;

each of $R^4$, $R^5$, and $R^7$ is hydrogen;

$R^6$ is halogen or substituted phenyl; and $R^{13}$ is halogen, —CN, —OH, or —OCH$_3$.

16. The compound of claim 1, or a pharmaceutically acceptable salt, or solvate thereof, having the structure of Formula (VI):

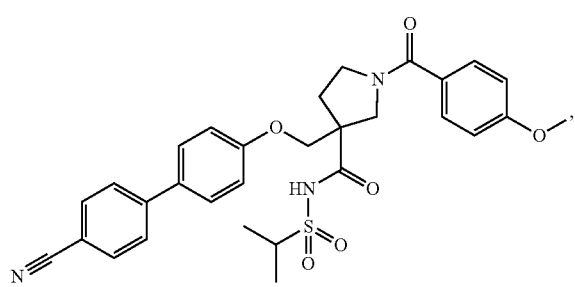

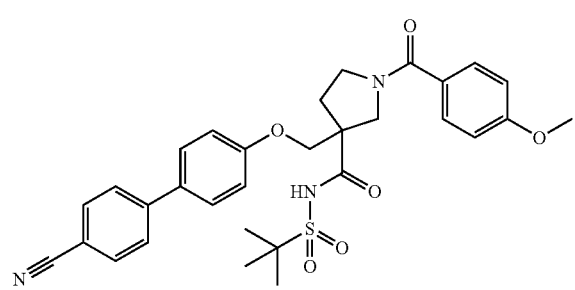

Formula (VI)

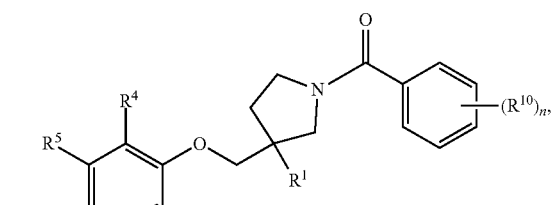

or a pharmaceutically acceptable salt or solvate thereof.

17. The compound of claim 1, or a pharmaceutically acceptable salt, or solvate thereof, wherein the compound has the structure of Formula (VI-A):
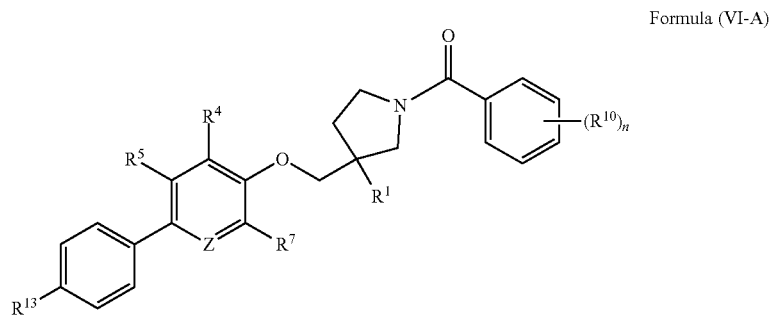
Formula (VI-A)
or a pharmaceutically acceptable salt, or solvate thereof.
* * * * *